United States Patent
Collett et al.

(10) Patent No.: US 11,234,939 B2
(45) Date of Patent: Feb. 1, 2022

(54) DOSAGE FORMS COMPRISING A PLASMA KALLIKREIN INHIBITOR

(71) Applicant: KALVISTA PHARMACEUTICALS LIMITED, Wiltshire (GB)

(72) Inventors: John Herman Collett, Flintshire (GB); Gary Paul Cook, Westford, MA (US); Jamie Joseph Farrar, Flintshire (GB); Michael John Frodsham, Flintshire (GB); Michael Bryan Roe, Wiltshire (GB); Richard Simon Todd, Wiltshire (GB); Robert Neil Ward, Flintshire (GB)

(73) Assignee: KalVista Pharmaceuticals Limited, Porton Down (GB)

( * ) Notice: Subject to any disclaimer, the term of this patent is extended or adjusted under 35 U.S.C. 154(b) by 59 days.

(21) Appl. No.: 16/767,803

(22) PCT Filed: Nov. 28, 2018

(86) PCT No.: PCT/GB2018/053443
§ 371 (c)(1),
(2) Date: May 28, 2020

(87) PCT Pub. No.: WO2019/106361
PCT Pub. Date: Jun. 6, 2019

(65) Prior Publication Data
US 2020/0345647 A1 Nov. 5, 2020

Related U.S. Application Data

(60) Provisional application No. 62/592,242, filed on Nov. 29, 2017.

(30) Foreign Application Priority Data

Dec. 21, 2017 (GB) .................................. 1721515

(51) Int. Cl.
A61K 9/48 (2006.01)
A61K 9/16 (2006.01)
(Continued)

(52) U.S. Cl.
CPC .......... *A61K 9/4858* (2013.01); *A61K 9/1652* (2013.01); *A61K 9/2054* (2013.01);
(Continued)

(58) Field of Classification Search
CPC ...... A61K 9/1652; A61K 9/4891; A61K 9/16; A61K 9/4858; A61K 9/2853; A61K 9/48;
(Continued)

(56) References Cited

U.S. PATENT DOCUMENTS 5,187,157 A 2/1993 Kettner et al.
5,786,328 A 7/1998 Dennis et al.
(Continued)

FOREIGN PATENT DOCUMENTS

CA 2730078 A1 1/2010
EA 201200917 12/2012
(Continued)

OTHER PUBLICATIONS

PubChem Compound 55438190 Jan. 25, 2012.
(Continued)

*Primary Examiner* — Blessing M Fubara
(74) *Attorney, Agent, or Firm* — BakerHostetler

(57) ABSTRACT

The present invention relates to oral solid dosage forms comprising a plasma kallikrein inhibitor, in particular a solid form (Form 1) of the compound of Formula A. Also provided are methods of preparing oral solid dosage forms comprising the compound of Formula A using Form 1 of the compound of Formula A.

53 Claims, 15 Drawing Sheets

(51) Int. Cl.
*A61K 9/20* (2006.01)
*A61K 9/28* (2006.01)
*C07D 401/14* (2006.01)
*A61K 9/00* (2006.01)
*A61K 45/06* (2006.01)

(52) U.S. Cl.
CPC .......... *A61K 9/2853* (2013.01); *A61K 9/4891* (2013.01); *C07D 401/14* (2013.01); *A61K 9/0053* (2013.01); *A61K 45/06* (2013.01); *C07B 2200/13* (2013.01)

(58) Field of Classification Search
CPC .......... A61K 9/2054; A61K 9/28; A61K 9/20; A61K 9/2846; A61K 9/0053; A61K 31/00; A61K 31/444; A61K 45/06; C07D 401/14; C07B 2200/13
See application file for complete search history.

(56) References Cited

U.S. PATENT DOCUMENTS

| | | |
|---|---|---|
| 7,101,878 B1 | 9/2006 | Anderson et al. |
| 8,207,378 B2 | 6/2012 | Steinmeizer et al. |
| 9,382,219 B2 | 7/2016 | Das et al. |
| 9,512,065 B2 | 12/2016 | Northen et al. |
| 9,533,987 B2 | 1/2017 | Davie et al. |
| 9,670,157 B2 | 6/2017 | Allan et al. |
| 9,738,641 B2 | 8/2017 | Edwards et al. |
| 10,221,161 B2 | 3/2019 | Edwards et al. |
| 10,364,238 B2 | 7/2019 | Davie et al. |
| 2007/0254894 A1 | 11/2007 | Kane et al. |
| 2008/0038276 A1 | 2/2008 | Sinha et al. |
| 2008/0221091 A1 | 9/2008 | Gege et al. |
| 2009/0163545 A1 | 6/2009 | Goldfarb |
| 2010/0113782 A1 | 5/2010 | Bolin et al. |
| 2011/0152533 A1 | 6/2011 | Sinha et al. |
| 2012/0035168 A1 | 2/2012 | Brandl et al. |
| 2012/0298326 A1 | 11/2012 | Born |
| 2014/0213311 A1 | 7/2014 | Evans et al. |
| 2014/0378474 A1 | 12/2014 | Flohr et al. |
| 2015/0191421 A1 | 7/2015 | Northen et al. |
| 2015/0225450 A1 | 8/2015 | Evans et al. |
| 2015/0315198 A1 | 11/2015 | Li et al. |
| 2016/0039752 A1 | 2/2016 | Allan et al. |
| 2017/0305863 A1 | 10/2017 | Evans et al. |
| 2018/0319782 A1 | 11/2018 | Davie et al. |

FOREIGN PATENT DOCUMENTS

| | | |
|---|---|---|
| EA | 021359 | 5/2015 |
| EP | 1426364 A1 | 6/2004 |
| EP | 1568698 A1 | 8/2005 |
| EP | 2281885 A1 | 2/2011 |
| EP | 2807157 A1 | 12/2014 |
| EP | 3089746 A1 | 11/2016 |
| EP | 3224256 A1 | 10/2017 |
| JP | 2009-545611 A | 12/2009 |
| JP | 2010-520294 A | 6/2010 |
| JP | 2011-157349 A | 8/2011 |
| JP | 2013-532713 A | 8/2013 |
| RU | 2485114 C2 | 6/2013 |
| WO | 92/04371 A1 | 3/1992 |
| WO | 94/29335 A1 | 12/1994 |
| WO | 95/07921 A1 | 3/1995 |
| WO | 03/35076 A1 | 5/2003 |
| WO | 03/37274 A2 | 5/2003 |
| WO | 03/76458 A2 | 9/2003 |
| WO | 03/91226 A1 | 11/2003 |
| WO | 2004/062657 A1 | 7/2004 |
| WO | 2004/069792 A2 | 8/2004 |
| WO | 2005/049578 A1 | 6/2005 |
| WO | 2005/079800 A1 | 9/2005 |
| WO | 2005/123680 A1 | 12/2005 |
| WO | 2006/025714 A1 | 3/2006 |
| WO | 2006/091459 A2 | 8/2006 |
| WO | 2006/114313 A1 | 11/2006 |
| WO | 2007/001139 A1 | 1/2007 |
| WO | 2007/011626 A2 | 1/2007 |
| WO | 2007/113289 A1 | 10/2007 |
| WO | 2008/003697 A1 | 1/2008 |
| WO | 2008/016883 A2 | 2/2008 |
| WO | 2007/130842 A2 | 5/2008 |
| WO | 2008/049595 A1 | 5/2008 |
| WO | 2008/091692 A2 | 7/2008 |
| WO | 2008/119825 A2 | 10/2008 |
| WO | 2008/121670 A1 | 10/2008 |
| WO | 2009/012998 A1 | 1/2009 |
| WO | 2009/026407 A1 | 2/2009 |
| WO | 2009/083553 A1 | 7/2009 |
| WO | 2009/097141 A1 | 8/2009 |
| WO | 2009/106980 A2 | 9/2009 |
| WO | 2009/114677 A1 | 9/2009 |
| WO | 2010/142801 A1 | 12/2010 |
| WO | 2011/075684 A1 | 6/2011 |
| WO | 2011/094496 A2 | 8/2011 |
| WO | 2011/118672 A1 | 9/2011 |
| WO | 2012/004678 A2 | 1/2012 |
| WO | 2012/009009 A2 | 1/2012 |
| WO | 2012/017020 A1 | 2/2012 |
| WO | 2012/142308 A1 | 10/2012 |
| WO | 2012/174362 A1 | 12/2012 |
| WO | 2013/005045 A1 | 1/2013 |
| WO | 2013/048982 A1 | 4/2013 |
| WO | 2013/049096 A1 | 4/2013 |
| WO | 2013/111107 A1 | 8/2013 |
| WO | 2013/111108 A1 | 8/2013 |
| WO | 2013/120104 A2 | 8/2013 |
| WO | 2013/130603 A1 | 9/2013 |
| WO | 2014/006414 A1 | 1/2014 |
| WO | 2014/108406 A1 | 7/2014 |
| WO | 2014/108679 A1 | 7/2014 |
| WO | 2014/108685 A1 | 7/2014 |
| WO | 2014/113712 A1 | 7/2014 |
| WO | 2014/145986 A1 | 9/2014 |
| WO | 2014/188211 A1 | 11/2014 |
| WO | 2015/022546 A1 | 2/2015 |
| WO | 2015/022547 A1 | 2/2015 |
| WO | 2015/103317 A1 | 7/2015 |
| WO | 2015/134998 A1 | 9/2015 |
| WO | 2015/171526 A2 | 11/2015 |
| WO | 2015/171527 A1 | 11/2015 |
| WO | 2016/011209 A1 | 1/2016 |
| WO | 2016/029214 A1 | 2/2016 |
| WO | 2016/044662 A1 | 3/2016 |
| WO | 2016/083816 A1 | 6/2016 |
| WO | 2016/083818 A1 | 6/2016 |
| WO | 2016/083820 A1 | 6/2016 |
| WO | WO-2016083820 A1 * | 6/2016 .............. A61P 43/00 |
| WO | 2016/138532 A1 | 9/2016 |
| WO | 2017/001924 A1 | 1/2017 |
| WO | 2017/001926 A2 | 1/2017 |
| WO | 2017/001936 A2 | 1/2017 |
| WO | 2017/072020 A1 | 5/2017 |
| WO | 2017/072021 A1 | 5/2017 |
| WO | 2017/207983 A1 | 12/2017 |
| WO | 2017/207985 A1 | 12/2017 |
| WO | 2017/207986 A1 | 12/2017 |
| WO | 2017/207989 A1 | 12/2017 |
| WO | 2017/208002 A1 | 12/2017 |
| WO | 2017/208005 A1 | 12/2017 |
| WO | 2018/011628 A1 | 1/2018 |
| WO | 2019/106359 A1 | 6/2019 |
| WO | 2019/106375 A1 | 6/2019 |
| WO | 2019/106377 A1 | 6/2019 |

OTHER PUBLICATIONS

PubChem Compound 55494217 Jan. 25, 2012.
PubChem Compound 55650494 Jan. 25, 2012.
PubChem Compound 60376550 Oct. 18, 2012.
PubChem Compound ID 22830339 Dec. 5, 2007.
PubChem Compound ID 24488625 Feb. 29, 2008.

(56) References Cited

OTHER PUBLICATIONS

PubChem Compound ID 38284485 May 29, 2009.
PubChem Compound ID 38284487 May 29, 2009.
PubChem Compound ID 46438580 Jul. 23, 2010.
Registry No. 1015534-45-8, Chemical Library—FCG Group, Apr. 18, 2008, 1 page.
Registry No. 1027627-81-1, Chemical Library—FCG Group, Jun. 12, 2008, 1 page.
Registry No. 1028093-96-0, Chemical Library—FCG Group, Jun. 13, 2008, 1 page.
Registry No. 1028094-50-9, Chemical Library—FCG Group, Jun. 13, 2008, 1 page.
Registry No. 1028096-34-5, Chemical Library—FCG Group, Jun. 13, 2008, 1 page.
Registry No. 1028361-95-6, Chemical Library—FCG Group, Jun. 16, 2008, 1 page.
Registry No. 1061709-51-0, Chemical Library—FCG Group, Oct. 15, 2008, 1 page.
Registry No. 1062408-24-5, Chemical Library—FCG Group, Oct. 17, 2008, 1 page.
Registry No. 1086603-37-3, Chemical Library—AKos Consulting and Solutions GmbH, CHEMCATS, dated Dec. 18, 2008, 1 page.
Registry No. 1086603-42-0, Chemical Library—AKos Consulting and Solutions GmbH, CHEMCATS, dated Dec. 18, 2008, 1 page.
Registry No. 1086603-52-2, Chemical Library—AKos Consulting and Solutions GmbH, CHEMCATS, dated Dec. 18, 2008, 1 page.
Registry No. 1094996-93-6, Chemical Library—AKos Consulting and Solutions GmbH, CHEMCATS, dated Jan. 22, 2009, 1 page.
Registry No. 1103271-51-7, Chemical Library—FCG Group, Feb. 9, 2009, 1 page.
Registry No. 1170030-40-6, Chemical Library—FCG Group, Jul. 29, 2009, 1 page.
Registry No. 1171669-07-0, Chemical Library—FCG Group, Aug. 2, 2009, 1 page.
Registry No. 1171693-25-6, Chemical Library—Ambinter, CHEMCATS, dated Aug. 2, 2017, 1 page.
Registry No. 1278351-92-0, Chemical Library—FCG Group, Apr. 11, 2011, 1 page.
Registry No. 1280842-43-4, Chemical Library—FCG Group, Apr. 18, 2011, 1 page.
Registry No. 1317328-27-0, Chemical Library—FCG Group, Aug. 14, 2011, 1 page.
Registry No. 1317855-54-1, Chemical Library—FCG Group, Aug. 15, 2011, 1 page.
Registry No. 1318167-86-0, Chemical Library—FCH Group, CHEMCATS, dated Aug. 15, 2011, 1 page.
Registry No. 1318604-27-1, Chemical Library—FCG Group, Aug. 16, 2011, 1 page.
Registry No. 1320653-15-3, Chemical Library—FCG Group, Aug. 21, 2011, 1 page.
Registry No. 1321195-15-6, Chemical Library—FCG Group, Aug. 21, 2011, 1 page.
Registry No. 1321521-84-9, Chemical Library—FCG Group, Aug. 12, 2011, 1 page.
Registry No. 1386189-59-8, Chemical Library—Ukrorgsyntez Ltd., CHEMCATS, dated Aug. 3, 2012, 1 page.
Registry No. 1390613-03-2, Chemical Library—FCG Group, Aug. 13, 2012, 1 page.
Registry No. 1569406-35-4, Chemical Library—FCG Group, Mar. 18, 2014, 1 page.
Registry No. 1570266-44-2, Chemical Library—FCG Group, Mar. 19, 2014, 1 page.
Registry No. 1572436-72-6, Chemical Library—FCG Group, Mar. 24, 2014, 1 page.
Registry No. 1572946-10-1, Chemical Library—FCG Group, Mar. 25, 2014, 1 page.
Registry No. 1573976-69-8, Chemical Library—FCG Group, Mar. 26, 2014, 1 page.
Registry No. 1575214-30-0, Chemical Library—FCG Group, Mar. 28, 2014, 1 page.
Registry No. 1580327-09-8, Chemical Library—FCH Group, Apr. 4, 2014, 1 page.
Registry No. 1625594-62-8, Chemical Library—FCG Group, Sep. 24, 2014, 1 page.
Registry No. 879195-72-9, Chemical Library—FCG Group, Apr. 4, 2006, 1 page.
Registry No. 879300-81-9, Chemical Library—FCG Group, Apr. 5, 2006, 1 page.
Registry No. 955867-36-4, Chemical Library—FCG Group, Nov. 23, 2007, 1 page.
Registry No. 955899-78-2, Chemical Library—FCG Group, Nov. 25, 2007, 1 page.
Registry No. 956190-38-8, Chemical Library—FCG Group, Nov. 28, 2007, 1 page.
Registry No. 956290-77-0, Chemical Library—FCG Group, Nov. 29, 2007, 1 page.
Elman et al., "Randomized Trial Evaluating Ranibizumab Plus Prompt or Deferred Laser or Triamcinolone Plus Prompt Laser for Diabetic Macular Edema", Ophthalmology, Jun. 2010, 117(6), e35, pp. 1064-1077.
Enamine website on Jul. 25, 2013 from the Internet Archive Way Back Machine {https://web.archive.org/web/20130725053127/http://www.enamine.net/index.php?option=com_content&task=view&id=22.
Evans et al., "Selective Inhibitors of Plasma Kallikrein", Immunopharmacology, May 1996, 32(1-3), pp. 115-116.
Feener et al.; "Role of plasma kallikrein in diabetes and metabolism"; Thrombosis and Haemostasis; Sep. 2013; vol. 110(3); p. 434-441.
Garrett et al. "Peptide Aldehyde Inhibitors of the Kallikreins: an Investigation of Subsite Interactions with Tripeptides Containing Structural Variations at the Amino Terminus", J. Peptide Research, Jul. 1998, 52(1), 60-71.
Greisbacher et al.; "Involvement of tissue kallikrein but not plasma kallikrein in the development of symptoms mediated by endogenous kinins in acute pancreatitis in rats"; British Journal of Pharmacology; Nov. 2002; vol. 137(5); p. 692-700.
Hilfiker et al., "Polymorphism: In the Pharmaceutical Industry", 2006, 1-19.
Ikeda et al.; "Host Stromal Bradykinin B2 Receptor Signaling Facilities Tumor-Associated Angiogenesis and Tumor Growth"; Cancer Research; Aug. 2004; vol. 64; p. 5178-5185.
International Patent Application No. PCT/GB2015/053613: International Search Report dated Jun. 2, 2016, 5 pages.
International Patent Application No. PCT/GB2015/053613: Written Opinion dated Jun. 2, 2016, 9 pages.
International Search Report for PCT/GB2014/051592 completed Jul. 23, 2014.
Jaffa et al., "Plasma Prekallikrein a Risk Marker for Hypertension and Nephropathy in Type 1 Diabetes", Diabetes, May 2003, vol. 52, 1215-1221.
Jaffa et al.; "A Risk Marker for Hypertension and Nephropathy in Type 1 Diabetes"; Diabetes; May 2003; vol. 52; p. 1215-1221.
Johansen et al., "Assay of Kallikrein Inhibitors and Levels of Acetone-Activated Kallikrein in Plasma Specimens From Reactors to Dextran or to Contrast Media", Bioscience Ed, Int. J. Tiss. Reac., 1986, 185-192.
Katsuura et al., "Effects of a Highly Selective Synthetic Inhibitor of Plasma Kallikrein on Disseminated Intravascular Coagulation in Rats", Thrombosis Research, 1996, vol. 82, No. 4, 361-368.
Kenniston, J Bio Chem, "Inhibition of Plasma Kallikrein by a Highly Specific Active Site Blocking Antibody", vol. 289 (34), 2014, 23596-23608.
Kolte et al., "Biochemical Characterization of a Novel High-Affinity and Specific Kallikrein Inhibitor", British Journal of Pharmacology, Apr. 2011, 162(7), pp. 1639-1649.
Lehmann, "Ecallantide (DX-88), a Plasma Kallikrein Inhibitor for the Treatment of Hereditary Angioedema and the Prevention of Blood Loss in on-Pump Cardiothoracic Surgery", Expert Opinion Biol. Ther., Jul. 2008, 8(8), pp. 1187-1199.
Leinweber et al, "Possible Physiological Roles of Carboxylic Ester Hydrolases", Drug Metabolism Reviews, Jan. 1987, 18(4), pp. 379-439.

(56) References Cited

OTHER PUBLICATIONS

Liang et al., "Fast Dissolving Intraoral Drug Delivery Systems", Expert Opinion in Therapeutic Patents, Jun. 2001, 11(6), 981-986.
Lieberman et al. Pharmaceutical Dosage Forms: Tablets, Second Edition, vol. 2, 1989, XP008099925; 15 pages (front page and list of contents included), 145-157.
Lieberman et al., Pharmaceutical Dosage Forms: Tablets, vol. 1, 1980, pp. 145-157.
Liu et al.; "Hyperglycemia Induced Cerebral Hematoma Expansion is Mediated by Plasma Kallikrein"; Nat. Med.; Feb. 2011; vol. 17(2); p. 206-210.
Lussis et al.; "A single synthetic small molecule that generates force against a load"; Nature Nanotechnology; vol. 6; 2011; p. 553-557.
Lussis et al.; "A single synthetic small molecule that generates force against a load"; Nature Nanotechnology; vol. 6; 2011; p. S1-525 (Supplemental Information).
Luthin et al., "The Discovery of Novel Small Molecule Non-peptide Gonadotropin Releasing Hormone (GnRH) Receptor Antagonists" Bioorg Med Chem Lett, 12, 2002, pp. 3467-3470.
Marceau et al., "Bradykinin receptor ligands: therapeutic perspectives", Nature Review, Drug Discovery 2004, Oct. 2004, vol. 3, 845-852.
Marra et al, "Solution Formulation Development of a VEGF Inhibitor for Intravitreal Injection", 2011, 12(1), 362-370.
Maurice, "Review: Practical Issues in Intravitreal Drug Delivery", Journal of Ocular Pharmacology and Therapeutics, 2001, 17(4), 393-401.
MedicineNet (2004) Web:<http://www.medterms.com>.
Obach, "Prediction of human clearance of twenty-nine drugs from hepatic microsomal intrinsicclearance data: An examination of in vitro half-life approach and nonspecific binding tomicrosomes", Drug Metabolism and Disposition, 1999, 27(11), 1350-13592.
Okada et al., "Development of Potent and Selective Plasmin and Plasma Kallikrein Inhibitors and Studies on the Structure-Activity Relationship", Chem. Pharm. Bull., Sep. 2000, 48, pp. 1964-1972.
Pace, et al., "4-Hydroxy-5-pynolinone-3-carboxamide HIV-1 integrase inhibitors", Bioorganic & Medicinal Chemistry Letters., 18, Jun. 2008, pp. 3865-3869.
Patel, "Combination Therapy for Age-Related Macular Degeneration", Retina, Jun. 2009, 29(6), S45-S48.
Prassas, "Unleashing the therapeutic potential of human kallikrein-relatedserine proteases", Nature Reviews Drug Discovery, vol. 14, 183-202, 2015.
PubChem Compound 40150888 May 30, 2009.
PubChem Compound 51143945 May 3, 2011.
PubChem Compound 52011740 May 20, 2011.
PubChem Compound 52011741 May 20, 2001.
PubChem Compound 52011742 May 20, 2011.
PubChem Compound 52011935 May 20, 2011.
PubChem Compound 52011936 May 20, 2011.
PubChem Compound 52011937 May 20, 2011.
PubChem Compound 52011938 May 20, 2011.
PubChem Compound 55389827 Jan. 25, 2012.
PubChem Compound 55408484 Jan. 25, 2012.
PubChem Compound 55408530 Jan. 25, 2012.
PubChem Compound 55408677 Jan. 25, 2012.
PubChem Compound 55408742 Jan. 25, 2012.
PubChem Compound 55408894 Jan. 25, 2012.
Registry No. 1572751-33-7, Chemical Library—FCH Group, dated Mar. 24, 2014.
Rodriguez-Spong, et al: General principles of pharmaceutical solid polymorphism: a supramolecular perspective; 56, 2004, 241-274.
Ambinter Sari: "1 H-Pyrazole-4-carboxamides" In: Chemical Catalog, 11; Sep. 2011 (Sep. 11, 2011), Ambinter SARL, XP055601375.
Aulton's pharmaceutics the design and manufacture of medicines, 3rd Ed, Churchill LivingstoneElsevier, Hungary, 2007, p. 356.
Babu et al., "A Simple, Sensitive and Selective Fluorogenic Assay to Monitor Plasma Kallikrein Inhibitory Activity of BCX4161 in Activated Plasma", Journal of Allergy and Clinical Immunology, Feb. 2014, 133(2 Supp), Abstract AB40, p. 1.
Babu, "Drug Discovery at BioCryst Pharmaceuticals Inc.", Presentation, http://files.shareholder.com/downloads/BCRX/0x0x403076/97a18d6e-1621-4fc6--8f5fd0828bddab4f/, Sep. 16, 2010, 18 pages.
Baeriswyl et al., "A Synthetic Factor XIIa Inhibitor Blocks Selectively Intrinsic Coagulation Initiation", ACS Chem. Biol., 2015, 10(8), 1861-1870.
Bernstein et al., "Polymorphism in Molecular Crystals", 2002, pp. 1-8.
Bhoola et al., "Bioregulation of Kinins: Kallikreins, Kininogens and Kininases", Pharmacological Rev., Mar. 1992, 44(1), pp. 1-80.
Bhoola et al., "Kallikrein-Kinin Cascade" Encyclopedia of Respiratory Medicine, 2006, pp. 483-493.
Bird et al.; Effects of plasma kallikrein deficiency on haemostasis and thrombosis in mice: Murine Ortholog of the Fletcher Trait Thrombosis and Haemostasis; Mar. 8, 2012; vol. 107; p. 1141-50.
Bjorkqvist et al., "Plasma kallikrein: the bradykinin-producing enzyme", Thrombosis and Haemotasis, 2013, 110, 399-407.
Bouckaert et al., "Synthesis, evaluation and structure-activity relationship of new 3-carboxamide coumarins as FXIIa inhibitors", European Journal of Medicinal Chemistry, 2016, 110, 181-194.
Bryant et al., "Human Plasma Kallikrein-Kinin System: Physiological and Biochemical Parameters", Cardiovascular and Haematological Agents in Medicinal Chemistry, Jul. 2009, pp. 234-250.
Caddick et al., "Convenient Synthesis of Protected Primary Amines from Nitriles", Tetrahedron Letters, Apr. 29, 2000, 41(18), 3513-3516.
Calderone et al., "1,2,3-Triazol-Carboxanilides and 1,2,3-Triazol-(N-Benzyl)-Carboxamides as BK-Potassium Channel Activators. XII" European Journal of Medicinal Chemistry 43, 2008, pp. 2618-2626.
Campbell, "Towards Understanding the Kallikrein-Kinin System: Insights from the Measurement of Kinin Peptides", Brazilian Journal of Medical and Biological Research, Jun. 2000, 33(6), 665-677.
Cannon, Chapter Nineteen in Burger's Medicinal Chemistry and Drug Discovery, Fifth Edition, vol. I: Principles and Practice, Wiley-Interscience 1995, pp. 783-802.
CAS abstract accession No. 1990:515202, corresponding to Ried et al. Liebigs Annalen der Chemie, 1990, 8, 2 pages.
CAS abstract accession No. 2013:1177162, corresponding to Ye et al. Chemical Science, 2013, 4(9), 4 pages.
CAS abstract accession No. 2013:1592386, corresponding to FR2989085 A1 (Commissariat Energie Atomique), 3 pages.
CAS abstract accession Nos. 2009:769551 and 2009:846114, corresponding to U.S. Publication 2009-0163545A1, 5 pages.
CAS extract for Compound 1180236-10-5; Sep. 4, 2009.
CAS extract for Compound 1180808-34-7; Sep. 6, 2009.
CAS Extract for Compound 1197490-19-9, dated Dec. 16, 2009, 1 page.
CAS Extract for Compound 120842-43-4, dated Apr. 18, 2011, 1 page.
CAS extract for Compound 1288265-35-9; May 1, 2011.
CAS extract for Compound 1288488-40-3; May 1, 2011.
CAS extract for Compound 1288531-53-2; May 1, 2011.
CAS extract for Compound 1293757-54-6; May 12, 2011.
CAS extract for Compound 1297493-36-7; May 19, 2011.
CAS Extract for Compound 1386962-55-5, dated Aug. 6, 2012, 1 page.
CAS Extract for Compound 1388550-15-9, dated Aug. 9, 2012, 1 page.
CAS Extract for Compound 1626023-22-0, dated Sep. 25, 2014, 1 page.
CAS Structures cited in WO201683818 Written Opinion dated Jun. 2, 2016, 290 pages.
Chemical & Engineering News, Feb. 24, 2003, pp. 32-35.
Chemical Abstract Service, CHEMCATS, RN 1424383-07-2, Mar. 15, 2013.
Chemical Abstracts Registry No. 1147797-44-1, indexed in the Registry file on STN CAS Online May 20, 2009.
Chemical Abstracts Registry No. 1217027-87-6, indexed in the Registry file on STN CAS Online Apr. 5, 2010.
Chemical Abstracts Registry No. 1241137-33-6, indexed in the Registry file on STN CAS Online Sep. 15, 2010.

(56) References Cited

OTHER PUBLICATIONS

Chemical Abstracts Registry No. 1295467-87-6, indexed in the Registry file on STN CAS Online May 16, 2011.
Chemical Abstracts Registry No. 1296846-83-7, indexed in the Registry file on STN CAS Online May 18, 2011.
Chemical Abstracts Registry No. 1297526-11-4, indexed in the Registry file on STN CAS Online May 19, 2011.
Chemical Abstracts Registry No. 1389653-06-8, indexed in the Registry file on STN CAS Online Aug. 12, 2012.
Chemical Abstracts Registry No. 1575116-26-5, indexed in the Registry file on STN CAS Online Mar. 28, 2014.
Chemical Abstracts Registry No. 942731-43-3, indexed in the Registry file on STN CAS Online Jul. 19, 2007.
Chilcote et al., "ASP-634: An Oral Drug Candidate for Diabetic MacularEdema", ARVO 2012 May 6-May 9, 2012, Fort Lauderdale, Florida, (Presentation 2240), 1 page.
Clermont et al., "Plasma Kallikrein Mediates Retinal Vascular Dysfunction and Induces Retinal Thickening in Diabetic Rats", Diabetes, May 2011, 60(5), pp. 1590-1598.
Collis et al., "BCX4161, An Oral Kallikrein Inhibitor: Safety and Pharmacokinetic Results of a Phase 1 Study in Healthy Volunteers", Journal of Allergy and Clinical Immunology, vol. 133, Issue 2, Supplement, Feb. 2014, p. AB39.
Colman et al.; "Plasma and tissue kallikrein in arthritis and inflammatory bowel disease" Immunopharmacology; Sep. 1999; vol. 43; p. 103-108.
Davis III et al.; "Biological activities of C1 inhibitor"; Molecular Immunology; Oct. 2008; vol. 45; p. 4057-4063.
Durairaj et al., "Prediction of Vitreal Half-Life Based on Drug Physiochemical Properties: Quantitative Structure-Pharmacokinetic Relationships (QSPKR)", Pharmaceutical Research, 2009, 26(5), 1236-1260.
Registry No. 956444-80-7, Chemical Library—FCG Group, Dec. 2, 2007, 1 page.
Registry No. 956521-49-6, Chemical Library—FCG Group, Dec. 3, 2007, 1 page.
Registry No. 956529-72-9, Chemical Library—FCG Group, Dec. 3, 2007, 1 page.
Registry No. 956747-39-0, Chemical Library—FCG Group, Dec. 5, 2007, 1 page.
Remington's Pharmaceutical Sciences, 19.sup.th Edition, Gennaro, Mack Publishing Company, 1995, 5 pages.
Revenko et al.; "Selective depletion of plasma prekallikrein or coagulation factor XII inhibits thrombosis in mice without increased risk of bleeding"; Blood; Aug. 5, 2011; 118; p. 5302-5311.
Shori et al., "New Specific Assays for Tonin and Tissue Kallikrein Activities in Rat Submandibular Glands: Assays Reveal Differences in the Effects of Sympathetic and Parasympathetic Stimulation on Proteinases in Saliva", Biochemical Pharmacology, Mar. 17, 1992, 43(6), pp. 1209-1217.
Siebeck et al.; "Inhibition of Plasma Kallikrein With Aprotinin in Porcine Endotoxin Shock"; Journal of Trauma; Feb. 1993; vol. 34 No. 2; p. 193-198.
Stahl et al., "Handbook of Pharmaceutical Salts: Properties, Selection and Use", Wiley-VCH, Weinheim, Germany, 2002, 1 page.
STN Registry, "5-Pyrimidinecarboxamide, 1,6-dihydro-N-[1-(6-methyl-1 H-benzimidazol-2-yl)ethyl]-2-oxo-2-(1 H-1,2,4—triazol-1-ylmethyl)", CAS No. 1422635-37-7, Mar. 8, 2013.
STN Registry, "5-Pyrimidinecarboxamide, N-[1-(1 H-benzimidazol-2-yl)ethyl]-1,6-dihydro-6-oxo-2-(phenoxymethyl)", CAS No. 1434334-41-4, Jun. 5, 2013.
Sturzbecher et al., "Novel plasma kallikrein inhibitors of the benzamidine type", Brazilian J. med. Biol. Res., 1994, 27, 1929-1934.
Sturzebecher et al., "Inhibition of Human Mast Cell Tryptase by Benzamidine Derivatives", Biological Chemistry Hoppe-Seyler, Oct. 1992, 373(2), 1025-1030.
Tanaka et al., Thrombosis Research 2004, "Evaluation of a novel kallikrein inhibitor on hemostatic activation in vitro"; 113, 333-339.
Tang et al., "Expression, Crystallization, and Three-Dimensional Structure of the Catalytic Domain of Human Plasma Kallikrein" The Journal of Biological Chemistry vol. 280, No. 49, Dec. 2005, pp. 41077-41089.
Teno et al., "Development of Active Center-Directed Plasmin and Plasma Kallikrein Inhibitors and Studies on the Structure-Inhibitory Activity Relationship", Chem. Pharm. Bull., Jun. 1993, 41, 1079-1090.
Tombran-Tink et al., "Opthamology Research", Visual Dysfunction in Diabetes the Science of Patient Impairment and Health Care, 2012, 4 pages.
Tombran-Tink et al.; "Visual Dysfunction in Diabetes: The Science of Patient Impairment and Health Care"; Humana Press; 2012; p. 34.
Ulven et al.; "6-Acylamino-2-amino-4-methylquinolines as potent melanin-concentrating hormone 1 receptor antagonists: Structure-activity exploration of eastern and western parts"; Bioorganic & Medicinal Chemistry Letters; vol. 16 Issue 4; Feb. 2006; p. 1070-1075.
Wang et al., "Determination of In Vitro Permeability of Drug Candidates through a Caco-2 Cell Monolayer by Liquid Chromatography/Tandem Mass Spectrometry" J. Mass Spectrom 35(1); 71-76, 2000.
Wermuth et al., Handbook of Pharmaceutical Salts: Properties, Selection and Use, 2002 vol. 24, No. 3, p. 20.
Wermuth, "The Practice of Medicinal Chemistry", 2003, 2nd Ed., pp. 561-585.
Young et al., "Small Molecule Inhibitors of Plasma Kallikrein", Bioorg. Med. Chem. Letts., Apr. 2006, 16(7), pp. 2034-2036.
Zhang et al. "Discovery of Highly Potent Small Molecule Kallikrein Inhibitors" Medicinal Chemistry, 2006, 2, pp. 545-553.
Brittain et al., "Polymorphism in Pharmaceutical Solids", 1999, 234-239.
Byrn et al., "Solid-State Chemistry of Drugs", 1999, 1-17, 233-247.
DeNinno, M. P. et al., "1,5-Substituted nipecotic amides: Selective PDE8 inhibitors displaying diastereomer-dependent microsomal stability", Bioorganic & Medicinal Chemistry Letters, 2011, vol. 21, 3095-3098.
Golub, et al., "Molecular Classification of Cancer: Class Discovery and Class Prediction by Gene Expression Monitoring", Science, Oct. 15, 1999, vol. 286, 531-537.
Lala, et al., "Role of nitric oxide in tumor progression: Lessons from experimental tumors", Cancer and Metastasis Reviews, 1998, 17: 91-106.
Cicardi, DX-88 a recombinant inhibitor of human plasma kallikrein. Efficacy and safety in hereditary and acquired angioedema, Abstracts/ Molecular Immunology, 40, 2003, pp. 197-198, Abstract 55.
Clermont, et al: IOVS, Plasma Kallikrein Mediates Vascular Endothelial Growth Factor-Induced Retinal Dysfunction and Thickening, May 2016, vol. 57, No. 6, 2391-2399.
Patel, et al: Allery and Asthma Proceedings; Ecallantide for treatment of acute attacks of acquired C1 esterase inhibitor deficiency; Jan.-Feb. 2013, vol. 34, No. 1, 72-77.
Van den Elzen, et al: Clinic Rev Allerg Immunol; Efficacy of Treatment of Non-hereditary Angioedema; 2018, 54, 412-431.

* cited by examiner

PM0059_16

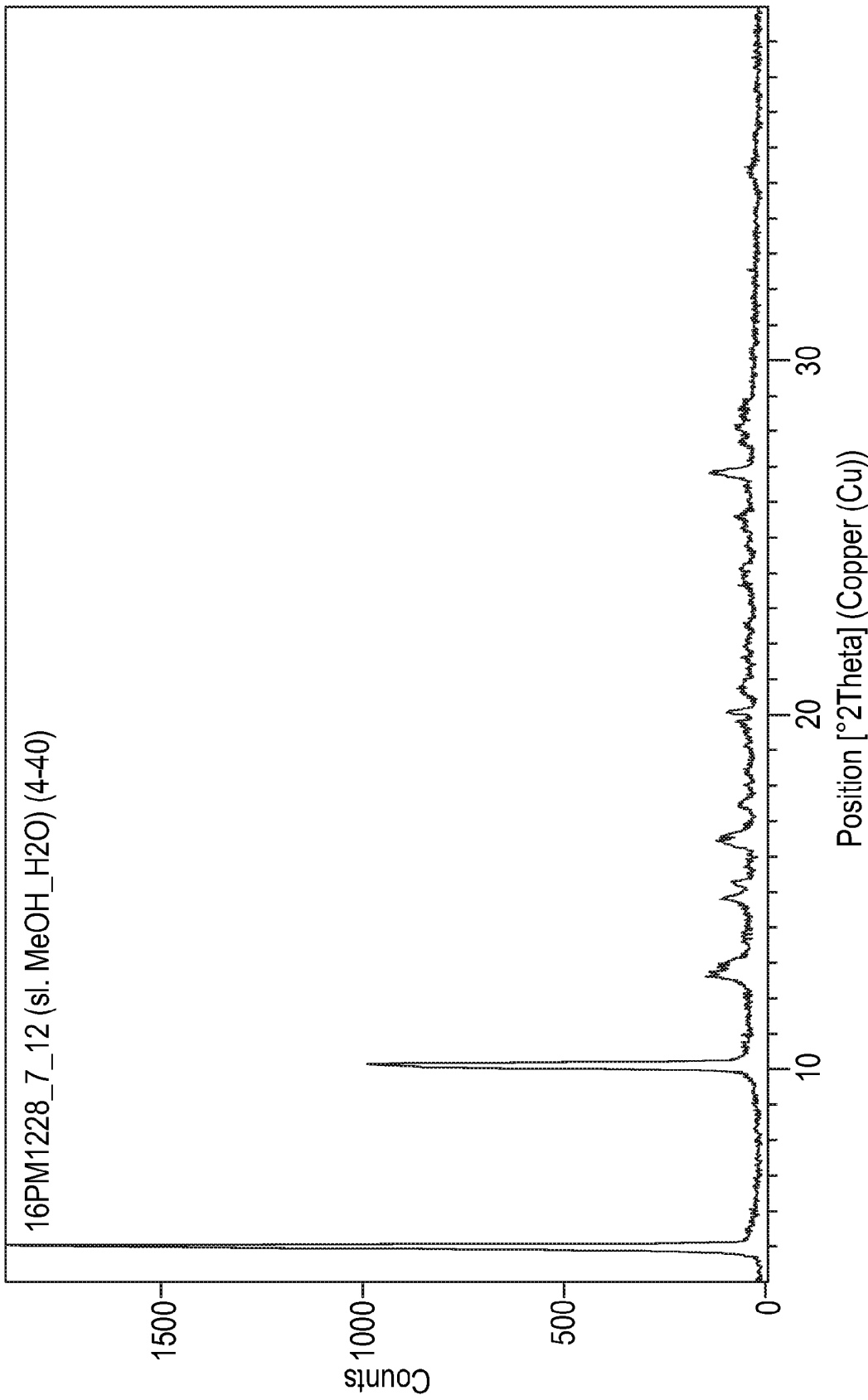

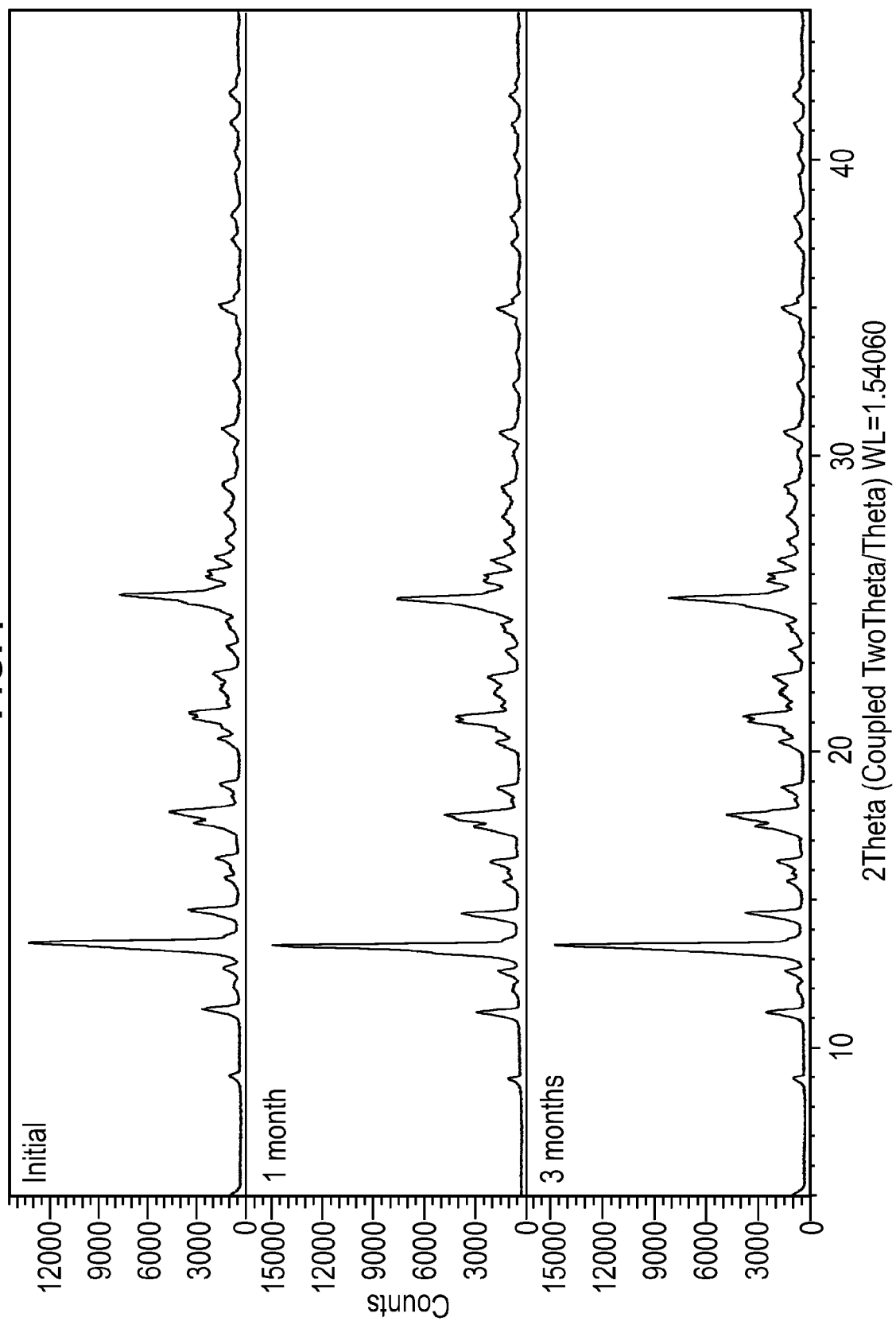

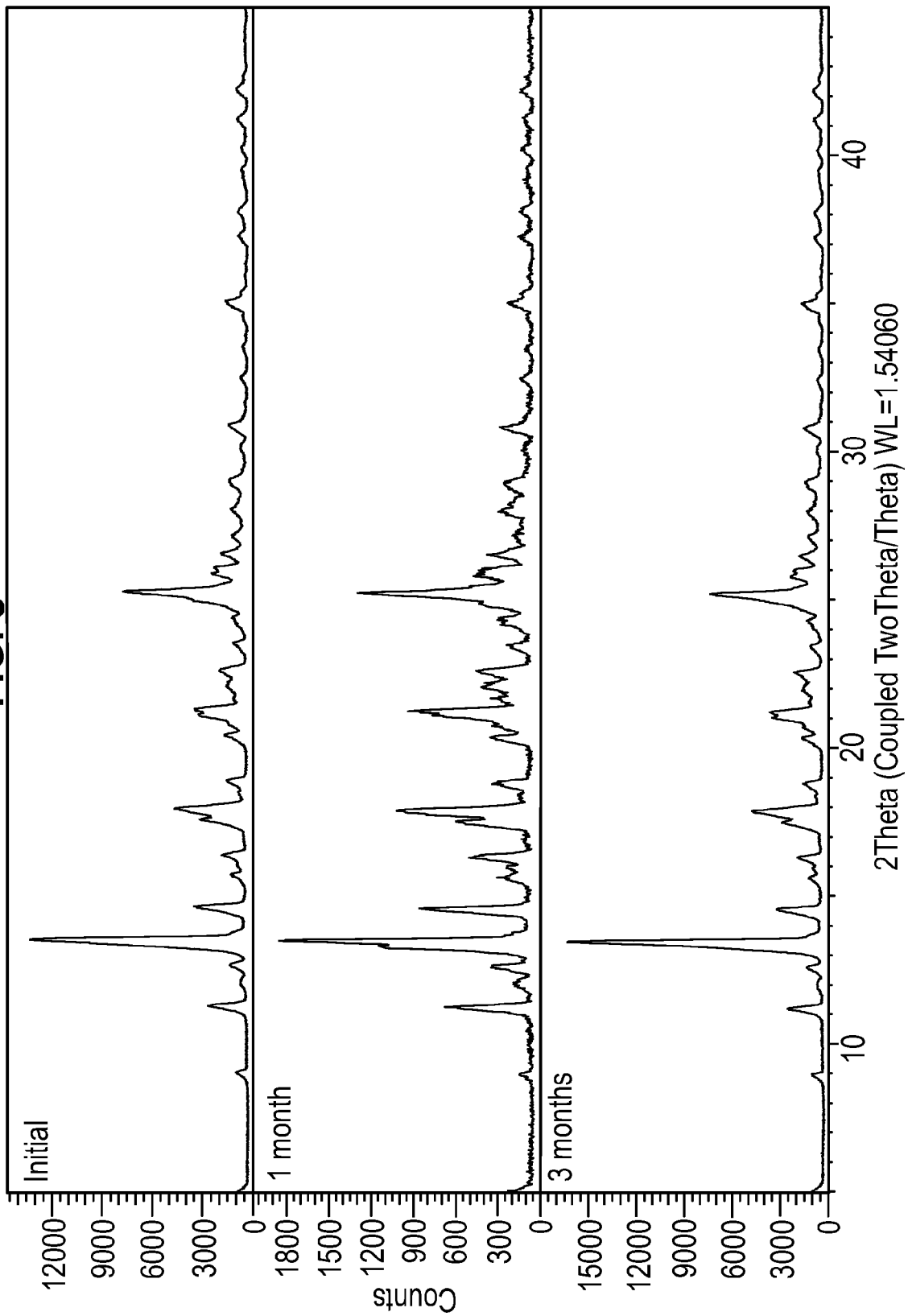

DOSAGE FORMS COMPRISING A PLASMA KALLIKREIN INHIBITOR

CROSS-REFERENCE TO RELATED APPLICATIONS

This application is the National Stage of International Patent Application No. PCT/GB2018/053443 filed Nov. 28, 2018, which claims priority from U.S. Patent Application No. 62/592,242 filed Nov. 29, 2017 and Great Britain Patent Application No. 1721515.3 filed Dec. 21, 2017, the disclosures of each of which are incorporated herein by reference in their entireties for any and all purposes.

FIELD OF THE INVENTION

The present invention relates to oral solid dosage forms comprising a plasma kallikrein inhibitor, in particular a solid form (Form 1) of the compound of Formula A. Also provided are methods of preparing oral solid dosage forms comprising the compound of Formula A using Form 1 of the compound of Formula A.

BACKGROUND TO THE INVENTION

Inhibitors of plasma kallikrein have a number of therapeutic applications, particularly in the treatment of retinal vascular permeability associated with diabetic retinopathy, diabetic macular edema and hereditary angioedema.

Plasma kallikrein is a trypsin-like serine protease that can liberate kinins from kininogens (see K. D. Bhoola et al., "Kallikrein-Kinin Cascade", *Encyclopedia of Respiratory Medicine*, p 483-493; J. W. Bryant et al., "Human plasma kallikrein-kinin system: physiological and biochemical parameters" *Cardiovascular and haematological agents in medicinal chemistry*, 7, p 234-250, 2009; K. D. Bhoola et al., *Pharmacological Rev.*, 1992, 44, 1; and D. J. Campbell, "Towards understanding the kallikrein-kinin system: insights from the measurement of kinin peptides", *Brazilian Journal of Medical and Biological Research* 2000, 33, 665-677). It is an essential member of the intrinsic blood coagulation cascade although its role in this cascade does not involve the release of bradykinin or enzymatic cleavage. Plasma prekallikrein is encoded by a single gene and synthesized in the liver. It is secreted by hepatocytes as an inactive plasma prekallikrein that circulates in plasma as a heterodimer complex bound to high molecular weight kininogen which is activated to give the active plasma kallikrein. Kinins are potent mediators of inflammation that act through G protein-coupled receptors and antagonists of kinins (such as bradykinin antagonists) have previously been investigated as potential therapeutic agents for the treatment of a number of disorders (F. Marceau and D. Regoli, Nature Rev., Drug Discovery, 2004, 3, 845-852).

Plasma kallikrein is thought to play a role in a number of inflammatory disorders. The major inhibitor of plasma kallikrein is the serpin C1 esterase inhibitor. Patients who present with a genetic deficiency in C1 esterase inhibitor suffer from hereditary angioedema (HAE) which results in intermittent swelling of face, hands, throat, gastro-intestinal tract and genitals. Blisters formed during acute episodes contain high levels of plasma kallikrein which cleaves high molecular weight kininogen liberating bradykinin leading to increased vascular permeability. Treatment with a large protein plasma kallikrein inhibitor has been shown to effectively treat HAE by preventing the release of bradykinin which causes increased vascular permeability (A. Lehmann "Ecallantide (DX-88), a plasma kallikrein inhibitor for the treatment of hereditary angioedema and the prevention of blood loss in on-pump cardiothoracic surgery" *Expert Opin. Biol. Ther.* 8, p 1187-99).

The plasma kallikrein-kinin system is abnormally abundant in patients with advanced diabetic macular edema. It has been recently published that plasma kallikrein contributes to retinal vascular dysfunctions in diabetic rats (A. Clermont et al. "Plasma kallikrein mediates retinal vascular dysfunction and induces retinal thickening in diabetic rats" *Diabetes*, 2011, 60, p 1590-98). Furthermore, administration of the plasma kallikrein inhibitor ASP-440 ameliorated both retinal vascular permeability and retinal blood flow abnormalities in diabetic rats. Therefore a plasma kallikrein inhibitor should have utility as a treatment to reduce retinal vascular permeability associated with diabetic retinopathy and diabetic macular edema.

Plasma kallikrein also plays a role in blood coagulation. The intrinsic coagulation cascade may be activated by factor XII (FXII). Once FXII is activated (to FXIIa), FXIIa triggers fibrin formation through the activation of factor XI (FXI) thus resulting in blood coagulation. Plasma kallikrein is a key component in the intrinsic coagulation cascade because it activates FXII to FXIIa, thus resulting in the activation of the intrinsic coagulation pathway. Furthermore, FXIIa also activates further plasma prekallikrein resulting in plasma kallikrein. This results in positive feedback amplification of the plasma kallikrein system and the intrinsic coagulation pathway (Tanaka et al. (*Thrombosis Research* 2004, 113, 333-339); Bird et al. (*Thrombosis and Haemostasis*, 2012, 107, 1141-50).

Contact of FXII in the blood with negatively charged surfaces (such as the surfaces of external pipes or the membrane of the oxygenator that the blood passes during cardiopulmonary bypass surgery) induces a conformational change in zymogen FXII resulting in a small amount of active FXII (FXIIa). The formation of FXIIa triggers the formation of plasma kallikrein resulting in blood coagulation, as described above. Activation of FXII to FXIIa can also occur in the body by contact with negatively charged surfaces on various sources (e.g. bacteria during sepsis, RNA from degrading cells), thus resulting in disseminated intravascular coagulation (Tanaka et al. (*Thrombosis Research* 2004, 113, 333-339)).

Therefore, inhibition of plasma kallikrein would inhibit the blood coagulation cascade described above, and so would be useful in the treatment of disseminated intravascular coagulation and blood coagulation during cardiopulmonary bypass surgery where blood coagulation is not desired. For example, Katsuura et al. (*Thrombosis Research*, 1996, 82, 361-368) showed that administration of a plasma kallikrein inhibitor, PKSI-527, for LPS-induced disseminated intravascular coagulation significantly suppressed the decrease in platelet count and fibrinogen level as well as the increase in FDP level which usually occur in disseminated intravascular coagulation. Bird et al. (*Thrombosis and Haemostasis*, 2012, 107, 1141-50) showed that clotting time increased, and thrombosis was significantly reduced in plasma kallikrein-deficient mice. Revenko et al. (*Blood*, 2011, 118, 5302-5311) showed that the reduction of plasma prekallikrein levels in mice using antisense oligonucleotide treatment resulted in antithrombotic effects. Tanaka et al. (*Thrombosis Research* 2004, 113, 333-339) showed that contacting blood with DX-88 (a plasma kallikrein inhibitor) resulted in an increase in activated clotting time (ACT). Lehmann et al. (*Expert Opin. Biol. Ther.* 2008, 1187-99) showed that Ecallantide (a plasma kallikrein inhibitor) was found to delay contact activated induced coagulation. Lehmann et al. conclude that Ecallantide "had in vitro anticoagulant effects as it inhibited the intrinsic pathway of coagulation by inhibiting plasma kallikrein".

Plasma kallikrein also plays a role in the inhibition of platelet activation, and therefore the cessation of bleeding. Platelet activation is one of the earliest steps in hemostasis, which leads to platelet plug formation and the rapid cessation of bleeding following damage to blood vessels. At the site of vascular injury, the interaction between the exposed collagen and platelets is critical for the retention and activation of platelets, and the subsequent cessation of bleeding. Once activated, plasma kallikrein binds to collagen and thereby interferes with collagen-mediated activation of platelets mediated by GPVI receptors (Liu et al. (*Nat Med.*, 2011, 17, 206-210)). As discussed above, plasma kallikrein inhibitors reduce plasma prekallikrein activation by inhibiting plasma kallikrein-mediated activation of factor XII and thereby reducing the positive feedback amplification of the kallikrein system by the contact activation system.

Therefore, inhibition of plasma kallikrein reduces the binding of plasma kallikrein to collagen, thus reducing the interference of plasma kallikrein in the cessation of bleeding. Therefore plasma kallikrein inhibitors would be useful in the treatment of treating cerebral haemorrhage and bleeding from post operative surgery. For example, Liu et al. (*Nat Med.*, 2011, 17, 206-210) demonstrated that systemic administration of a small molecule PK inhibitor, ASP-440, reduced hematoma expansion in rats. Cerebral hematoma may occur following intracerebral haemorrhage and is caused by bleeding from blood vessels into the surrounding brain tissue as a result of vascular injury. Bleeding in the cerebral haemorrhage model reported by Liu et al. was induced by surgical intervention involving an incision in the brain parenchyma that damaged blood vessels. These data demonstrate that plasma kallikrein inhibition reduced bleeding and hematoma volume from post operative surgery. Björkqvist et al. (*Thrombosis and Haemostasis*, 2013, 110, 399-407) demonstrated that aprotinin (a protein that inhibits serine proteases including plasma kallikrein) may be used to decrease postoperative bleeding.

Other complications of diabetes such as cerebral haemorrhage, nephropathy, cardiomyopathy and neuropathy, all of which have associations with plasma kallikrein may also be considered as targets for a plasma kallikrein inhibitor.

Synthetic and small molecule plasma kallikrein inhibitors have been described previously, for example by Garrett et al. ("Peptide aldehyde . . . ." *J. Peptide Res.* 52, p 62-71 (1998)), T. Griesbacher et al. ("Involvement of tissue kallikrein but not plasma kallikrein in the development of symptoms mediated by endogenous kinins in acute pancreatitis in rats" British Journal of Pharmacology 137, p 692-700 (2002)), Evans ("Selective dipeptide inhibitors of kallikrein" WO03/076458), Szelke et al. ("Kininogenase inhibitors" WO92/04371), D. M. Evans et al. (Immunolpharmacology, 32, p 115-116 (1996)), Szelke et al. ("Kininogen inhibitors" WO95/07921), Antonsson et al. ("New peptides derivatives" WO94/29335), J. Corte et al. ("Six membered heterocycles useful as serine protease inhibitors" WO2005/123680), J. Stürzbecher et al. (Brazilian J. Med. Biol. Res 27, p 1929-34 (1994)), Kettner et al. (U.S. Pat. No. 5,187,157), N. Teno et al. (Chem. Pharm. Bull. 41, p 1079-1090 (1993)), W. B. Young et al. ("Small molecule inhibitors of plasma kallikrein" Bioorg. Med. Chem. Letts. 16, p 2034-2036 (2006)), Okada et al. ("Development of potent and selective plasmin and plasma kallikrein inhibitors and studies on the structure-activity relationship" Chem. Pharm. Bull. 48, p 1964-72 (2000)), Steinmetzer et al. ("Trypsin-like serine protease inhibitors and their preparation and use" WO08/049595), Zhang et al. ("Discovery of highly potent small molecule kallikrein inhibitors" Medicinal Chemistry 2, p 545-553 (2006)), Sinha et al. ("Inhibitors of plasma kallikrein" WO08/016883), Shigenaga et al. ("Plasma Kallikrein Inhibitors" WO2011/118672), and Kolte et al. ("Biochemical characterization of a novel high-affinity and specific kallikrein inhibitor", British Journal of Pharmacology (2011), 162(7), 1639-1649). Also, Steinmetzer et al. ("Serine protease inhibitors" WO2012/004678) describes cyclized peptide analogs which are inhibitors of human plasmin and plasma kallikrein.

To date, the only selective plasma kallikrein inhibitor approved for medical use is Ecallantide. Ecallantide is formulated as a solution for injection. It is a large protein plasma kallikrein inhibitor that presents a risk of anaphylactic reactions. Other plasma kallikrein inhibitors known in the art are generally small molecules, some of which include highly polar and ionisable functional groups, such as guanidines or amidines. Recently, plasma kallikrein inhibitors that do not feature guanidine or amidine functionalities have been reported. For example Brandi et al. ("N-((6-aminopyridin-3-yl)methyl)-heteroaryl-carboxamides as inhibitors of plasma kallikrein" WO2012/017020), Evans et al. ("Benzylamine derivatives as inhibitors of plasma kallikrein" WO2013/005045), Allan et al. ("Benzylamine derivatives" WO2014/108679), Davie et al. ("Heterocyclic derivates" WO2014/188211), and Davie et al. ("N-((het)arylmethyl)-heteroaryl-carboxamides compounds as plasma kallikrein inhibitors" WO2016/083820).

In the manufacture of pharmaceutical formulations, it is important that the active compound be in a form in which it can be conveniently handled and processed in order to obtain a commercially viable manufacturing process. Accordingly, the chemical stability and the physical stability of the active compound are important factors. The active compound, and formulations containing it, must be capable of being effectively stored over appreciable periods of time, without exhibiting any significant change in the physico-chemical characteristics (e.g. chemical composition, density, hygroscopicity and solubility) of the active compound.

It is known that manufacturing a particular solid-state form of a pharmaceutical ingredient can affect many aspects of its solid state properties and offer advantages in aspects of solubility, dissolution rate, chemical stability, mechanical properties, technical feasibility, processability, pharmacokinetics and bioavailability. Some of these are described in "Handbook of Pharmaceutical Salts; Properties, Selection and Use", P. Heinrich Stahl, Camille G. Wermuth (Eds.) (Verlag Helvetica Chimica Acta, Zurich). Methods of manufacturing solid-state forms are also described in "Practical Process Research and Development", Neal G. Anderson (Academic Press, San Diego) and "Polymorphism: In the Pharmaceutical Industry", Rolf Hilfiker (Ed) (Wiley VCH). Polymorphism in pharmaceutical crystals is described in Byrn (Byrn, S. R., Pfeiffer, R. R., Stowell, J. G., "Solid-State Chemistry of Drugs", SSCI Inc., West Lafayette, Ind., 1999), Brittain, H. G., "Polymorphism in Pharmaceutical Solids", Marcel Dekker, Inc., New York, Basel, 1999) or Bernstein (Bernstein, J., "Polymorphism in Molecular Crystals", Oxford University Press, 2002).

The applicant has developed a novel series of compounds that are inhibitors of plasma kallikrein, which are disclosed in WO2016/083820 (PCT/GB2015/053615). These compounds demonstrate good selectivity for plasma kallikrein and are potentially useful in the treatment of diabetic retinopathy, macular edema and hereditary angioedema. One such compound is N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide. The name N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide denotes the structure depicted in Formula A.

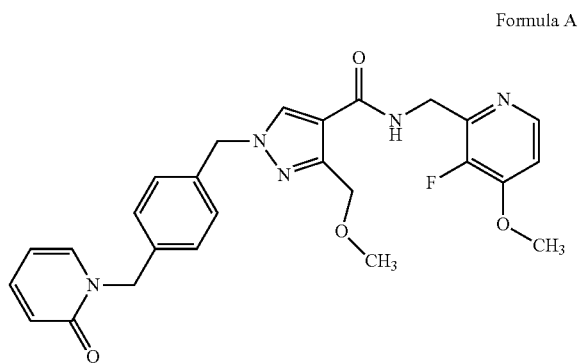 [SMILES: COCc1nn(Cc2ccc(Cn3ccccc3=O)cc2)cc1C(=O)NCc1nccc(OC)c1F]

Formula A

Initial attempts to prepare the compound of Formula A were performed by evaporation of the 1% ammonia-methanol/DCM solvent used during chromatography to yield a foam with XRPD data that shows mainly amorphous content. The applicant developed a novel solid form of this compound (herein referred to as 'Form 1') which has advantageous physico-chemical properties that render it suitable for development. Form 1 is disclosed in PCT/GB2017/051579 as Form 1. The applicant also developed a novel solid form of this compound (herein referred to as 'Form 3') which has advantageous physico-chemical properties that render it suitable for development. Form 3 is disclosed in PCT/GB2017/051579 as Form 3.

Four solid forms of the compound of Formula A have been isolated and characterised to date, which are disclosed in PCT/GB2017/051579. These solid forms are referred to as 'Form 1', 'Form 2', 'Form 3', and 'Form 4' in PCT/GB2017/051579.

It is an object of the present invention to provide an oral solid dosage form comprising Form 1 of the compound of Formula A. The invention is also concerned with providing methods of preparing oral solid dosage forms comprising the compound of Formula A using Form 1 of the compound of Formula A.

It is a further object of the present invention to provide an oral solid dosage form comprising Form 3 of the compound of Formula A. The invention is also concerned with providing methods of preparing oral solid dosage forms comprising the compound of Formula A using Form 3 of the compound of Formula A.

BRIEF DESCRIPTION OF THE DRAWINGS

FIG. 6a: X-ray powder diffraction pattern of Form 3 of the compound of Formula A (Example 4a).

FIG. 7: X-ray powder diffraction patterns of Form 1 of the compound of Formula A during a 25° C./60% RH stability study at 0 days (top), 1 month (middle) and 3 months (bottom).

FIG. 8: X-ray powder diffraction patterns of Form 1 of the compound of Formula A during a 40° C./75% RH stability study at 0 days (top), 1 month (middle) and 3 months (bottom).

DESCRIPTION OF THE INVENTION

Thus, in accordance with an aspect of the present invention, there is provided an oral solid dosage form comprising a solid form of the compound of Formula A, wherein the solid form of the compound of Formula A exhibits at least the following characteristic X-ray powder diffraction peaks (Cu Kα radiation, expressed in degrees 2θ) at approximately 11.2, 12.5, 13.2, 14.5 and 16.3. In the present application this solid form may be referred to as 'Form 1'.

Figure 4:
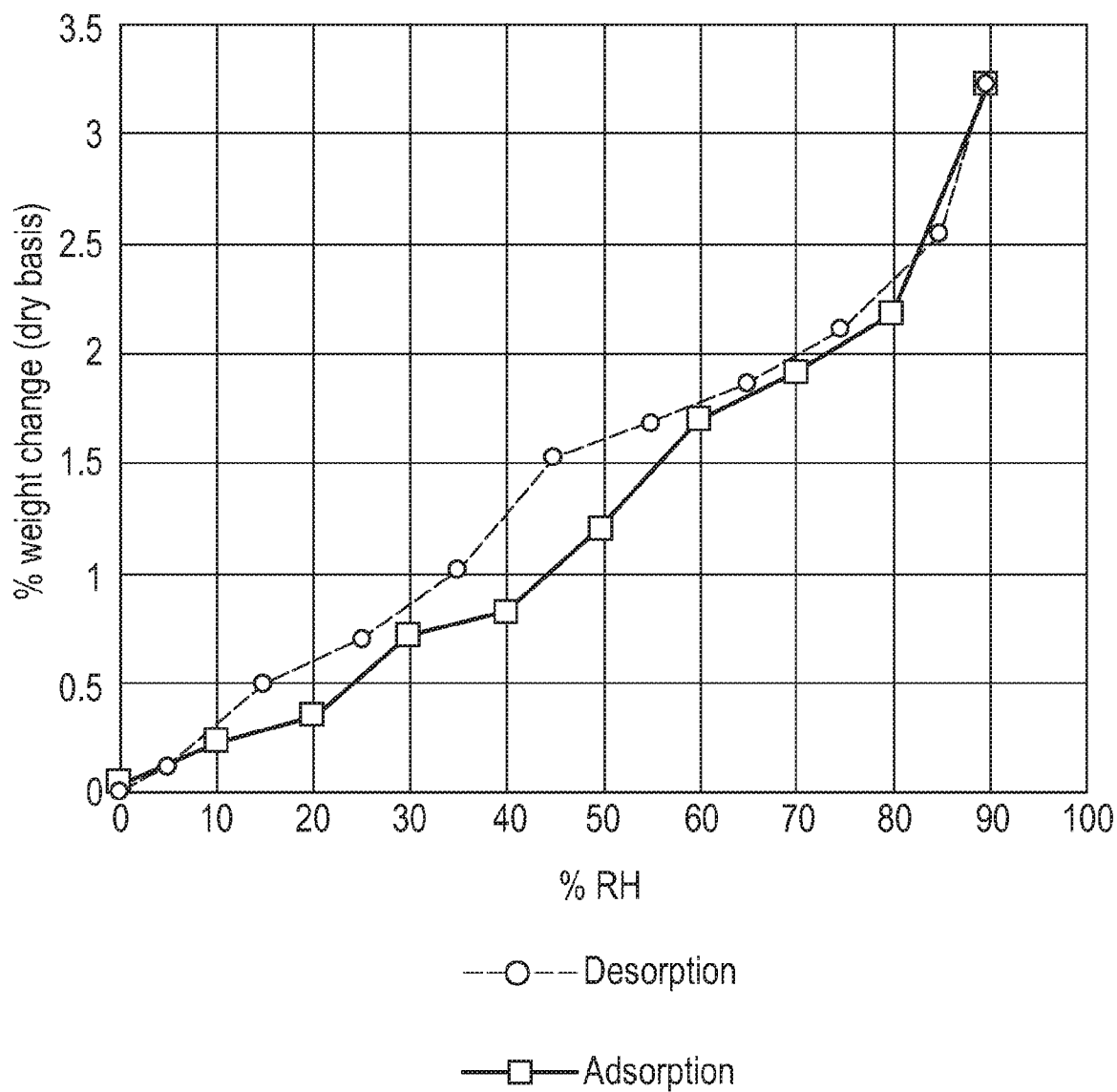
FIG. 4: Gravimetric vapour sorption isotherms (adsorption and desorption) of Form 1 of the compound of Formula A (Example 1).

Form 1 of the compound of Formula A has advantageous physico-chemical properties that render it suitable for development. For example, Gravimetric Vapour Sorption (GVS) data for Form 1 of the compound of Formula A, FIG. 4, shows that, under normal conditions (for example, up to 70% relative humidity) there is only a relatively gradual increase in water content. This is consistent with the absence of significant hygroscopicity. In contrast, amorphous materials are typically significantly hygroscopic, or even deliquescent, often rendering the material into an unworkable gum. Furthermore, the absence of weight loss before melt of the sample of Form 1 (see STA data, FIG. 2) indicates that Form 1 is not hydrated or solvated. Stable hydrates may be unsuitable for pharmaceutical development because they may induce an undesirable transformation of the administered anhydrous form of the drug once the drug meets the aqueous environment of the human body. Another advantage of Form 1 of the compound of Formula A is that it is more easily processable. That is, its preparation by crystallisation (see Examples) is a common and easily scalable procedure to remove undesirable impurities.

Further evidence of the suitability of Form 1 of the compound of Formula A for pharmaceutical development is provided by the stability data disclosed herein. Two samples of Form 1 of the compound of Formula A were stored at 25° C./60% RH and 40° C./75% RH packed in double polyethylene bags and sealed in a HDPE bottle. At the initial timepoint, XRPD showed the sample to be crystalline and consistent with Form 1. Under the storage conditions of 25° C./60% RH and 40° C./75% RH, XRPD showed no change after 1 month and after 3 months (FIGS. 7 and 8).

In the present specification, X-ray powder diffraction peaks (expressed in degrees 2θ) are measured using Cu Kα radiation.

The present invention provides an oral solid dosage form comprising a solid form (Form 1) of the compound of Formula A, wherein the solid form of the compound of Formula A exhibits at least the following characteristic X-ray powder diffraction peaks (Cu Kα radiation, expressed in degrees 2θ) at approximately:
(1) 11.2, 12.5, 13.2, 14.5 and 16.3; or
(2) 11.2, 12.5, 13.2, 14.5, 16.3, 17.4 and 17.9; or
(3) 11.2, 12.5, 13.2, 14.5, 16.3, 17.4, 17.9, 21.2 and 22.0.

The term "approximately" means in this context that there is an uncertainty in the measurements of the degrees 2θ of ±0.3 (expressed in degrees 2θ), preferably ±0.2 (expressed in degrees 2θ).

The present invention also provides an oral solid dosage form comprising a solid form of the compound of Formula A, wherein the solid form of the compound of Formula A has an X ray powder diffraction pattern comprising characteristic peaks (expressed in degrees 2θ) at approximately 4.4, 11.2, 12.5, 13.2, 14.5, 16.3, 17.4, 17.9, 21.2, 22.0 and 22.6.

Figure 1A:
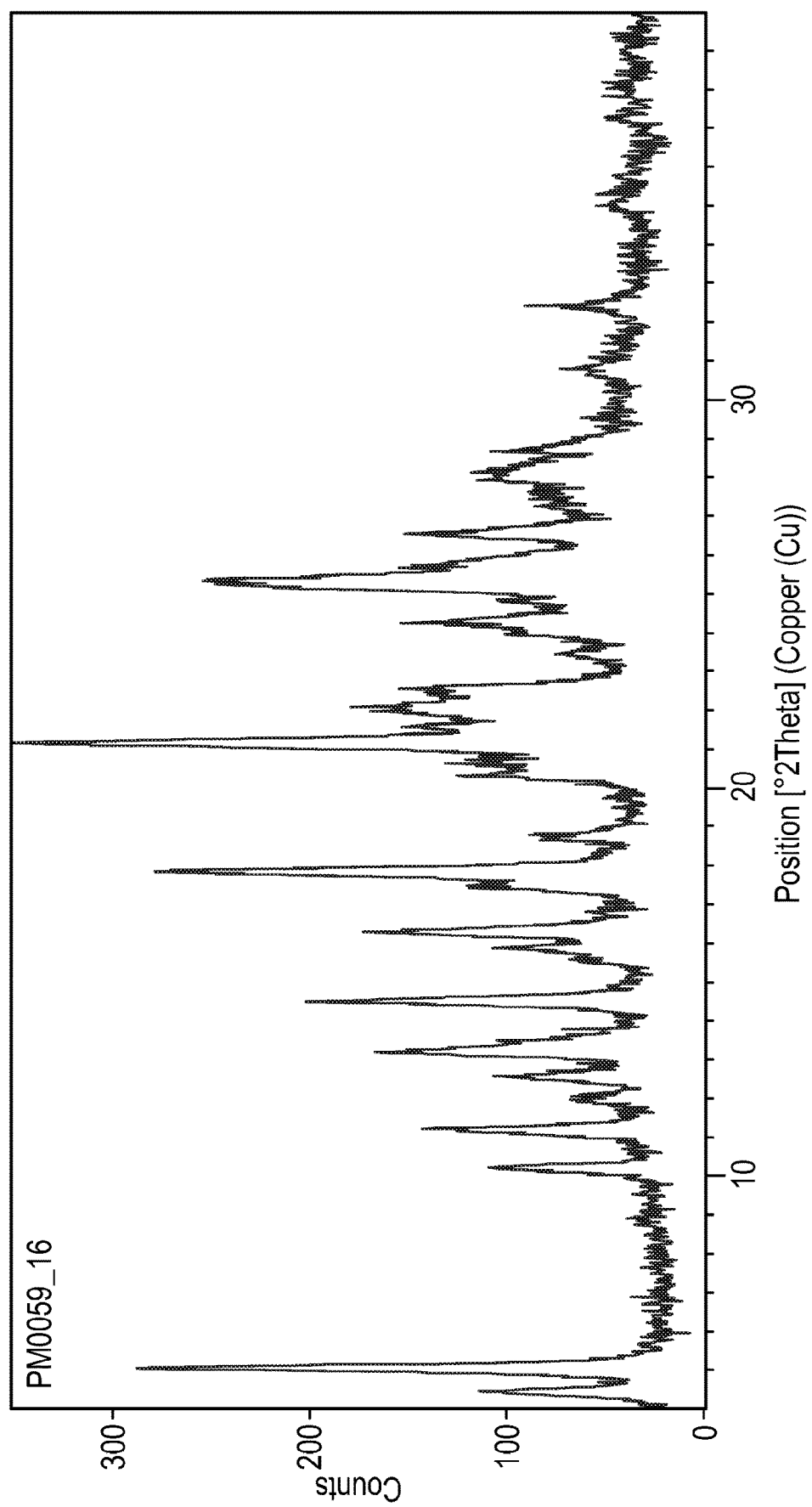
FIG. 1a: X-ray powder diffraction pattern of Form 1 of the compound of Formula A (Example 1).

The present invention also provides an oral solid dosage form comprising a solid form of the compound of Formula A, wherein the solid form of the compound of Formula A has an X-ray powder diffraction pattern substantially the same as that shown in FIG. 1a.

The X-ray powder diffraction pattern of a solid form may be described herein as "substantially" the same as that depicted in a Figure. It will be appreciated that the peaks in X-ray powder diffraction patterns may be slightly shifted in their positions and relative intensities due to various factors known to the skilled person. For example, shifts in peak positions or the relative intensities of the peaks of a pattern can occur because of the equipment used, method of sample preparation, preferred packing and orientations, the radiation source, and method and length of data collection. However, the skilled person will be able to compare the X-ray powder diffraction patterns shown in the figures herein with those of an unknown solid form to confirm the identity of the solid form.

The skilled person is familiar with techniques for measuring XRPD patterns. In particular, the X-ray powder diffraction pattern of the sample of compound may be recorded using a Philips X-Pert MPD diffractometer with the following experimental conditions:
Tube anode: Cu;
Generator tension: 40 kV;
Tube current: 40 mA;
Wavelength alpha1: 1.5406 Å;
Wavelength alpha2: 1.5444 Å;
Sample: 2 mg of sample under analysis gently compressed on the XRPD zero back ground single obliquely cut silica sample holder.

The present invention provides an oral solid dosage form comprising a solid form of the compound of Formula A, wherein the solid form of the compound of Formula A exhibits an endothermic peak in its DSC thermograph at 151±3° C., preferably 151±2° C., more preferably 151±1° C.

Figure 3:
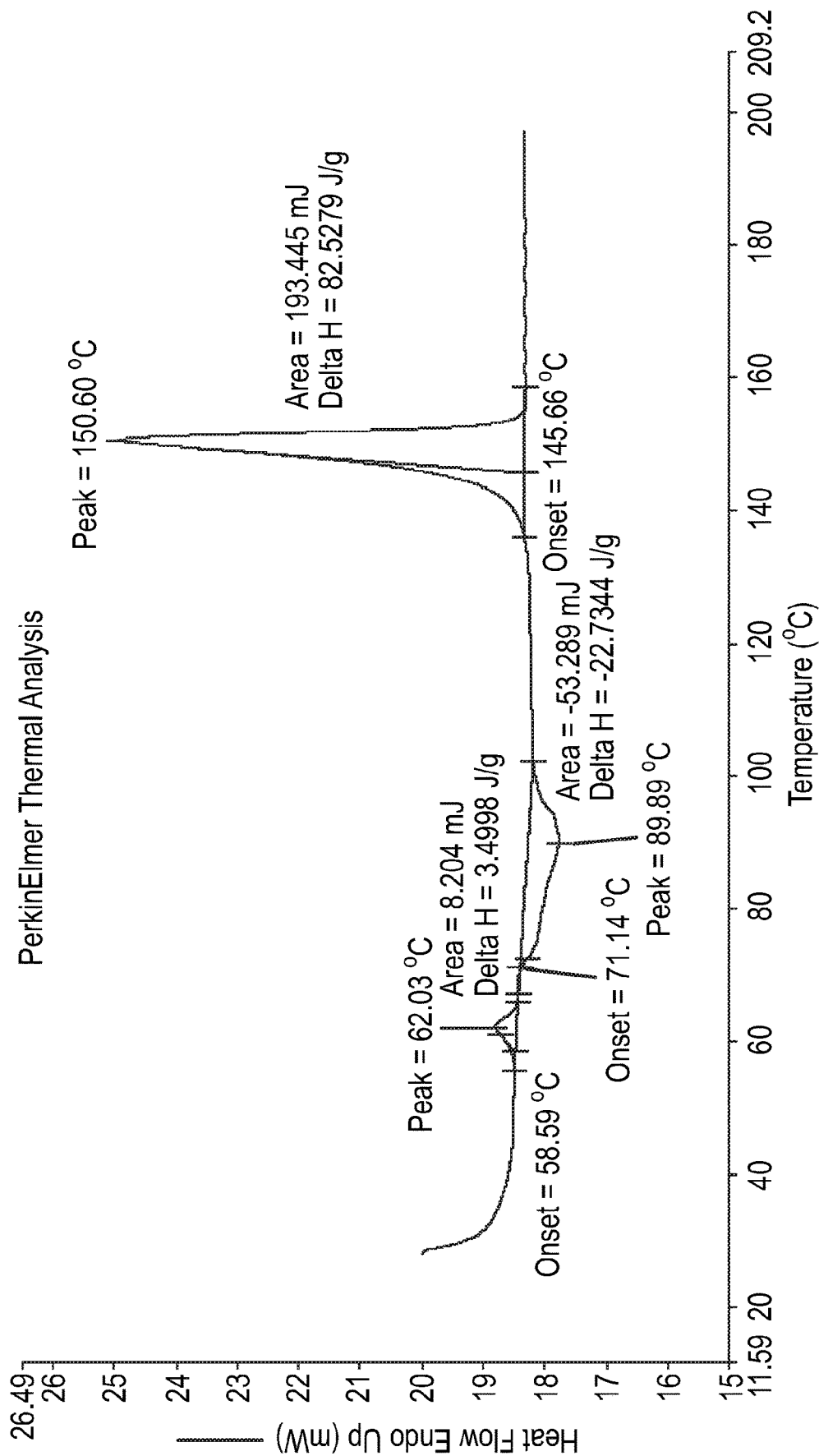
FIG. 3: DSC thermograph of Form 1 of the compound of Formula A (Example 1).

The present invention provides an oral solid dosage form comprising a solid form of the compound of Formula A, wherein the solid form of the compound of Formula A has a DSC thermograph substantially the same as that shown in FIG. 3.

The skilled person is familiar with techniques for measuring DSC thermographs. In particular, the DSC thermograph of the sample of compound may be recorded by
(a) weighing 5 mg of the sample into an aluminium DSC pan and sealing non-hermetically with an aluminium lid;
(b) loading the sample into a Perkin-Elmer Jade DSC and holding the sample at 30° C. until a stable heat-flow response is obtained while using a 20 cm$^3$/min helium purge;
(c) heating the sample to a temperature of between 200 and 300° C. at a scan rate of 10° C./min and monitoring the resulting heat flow response while using a 20 cm$^3$/min helium purge.

The present invention provides an oral solid dosage form comprising a solid form of the compound of Formula A, wherein the solid form of the compound of Formula A has an X-ray powder diffraction pattern as described above, and a DSC thermograph as described above.

The present invention also provides an oral solid dosage form comprising a solid form of the compound of Formula A, wherein the solid form of the compound of Formula A has an X-ray powder diffraction pattern substantially the same as that shown in FIG. 6a.

A reference to a particular compound also includes all isotopic variants.

The term "solid forms" described herein includes crystalline forms. Optionally, the solid forms of the invention are crystalline forms.

In an embodiment, the amount of the solid form of the compound of Formula A in the solid oral dosage form is between about 0.1 mg and about 1,000 mg, optionally between about 1 mg and about 1,000 mg, between about 5 mg and about 500 mg, between about 8 mg and about 200 mg, or between about 10 mg and about 100 mg.

The solid form of the compound of Formula A may be present in an amount of between about 1 wt % and about 70 wt %, optionally between about 5 wt % and about 60 wt %, or between about 5 wt % and about 50 wt % based on the total weight of the oral solid dosage form.

The oral solid dosage form may comprise a binder. Where present, the binder may comprise one or more of: methylcellulose, hydroxypropyl cellulose, hydroxypropyl methylcellulose, povidone, copovidone, gelatin, gum arabic, ethyl cellulose, polyvinyl alcohol, starch, pregelatinized starch, agar, tragacanth and sodium alginate. Preferably, the binder is povidone. Optionally, the binder is Kollidon K25 (a povidone formulation available from BASF Corporation).

The weight ratio of the compound of Formula A to the binder may be between about 1:0.01 and about 1:1, optionally between about 1:0.03 and about 1:0.5 or between about 1:0.05 and about 1:0.3.

The binder may be present in an amount of between about 0.1 wt % and about 30 wt %, optionally between about 0.5 wt % and about 10 wt %, or between about 1 wt % and about 5 wt % based on the total weight of the oral solid dosage form.

Alternatively or in addition, the oral solid dosage form may comprise a diluent. The diluent may comprise one or more of: calcium carbonate, calcium phosphate-dibasic, calcium phosphate-tribasic, calcium sulfate, microcrystalline cellulose, powdered cellulose, dextrates, dextrins, dextrose excipients, fructose, kaolin, lactitol, lactose, lactose monohydrate, mannitol, sorbitol, maltitol, starch, pregelatinized starch and sucrose. Preferably, the diluent is microcrystalline cellulose. Optionally, the diluent is Avicel PH 101 and/or Avicel PH 102 (which are both microcrystalline cellulose excipients available from FMC Corporation).

The weight ratio of the solid form of the compound of Formula A to the diluent may be between about 1:0.1 and about 1:500, optionally between about 1:0.2 and about 1:100, between about 1:0.5 and about 1:50, between about 1:0.75 and about 1:20, or between about 1:1 and about 1:5.

The diluent may be present in an amount of between about 1 wt % and about 99 wt %, optionally between about 10 wt % and about 70 wt %, or about 20 wt % and about 60 wt %, or about 40 wt % and about 60 wt % based on the total weight of the oral solid dosage form.

Alternatively or in addition, the oral solid dosage form may comprise a disintegrant. The disintegrant may comprise one or more of: carboxymethylcellulose calcium, carboxymethylcellulose sodium, croscarmellose sodium, cross-linked polyvinyl pyrrolidone, sodium starch glycolate, magnesium aluminum silicate, powdered cellulose, microcrystalline cellulose, low-substituted hydroxypropyl cellulose, polacrilin potassium, starch, pregelatinized starch, alginic acid and sodium alginate. Preferably, the disintegrant is croscarmellose sodium. Optionally, the disintegrant is AcDiSol (a croscarmellose sodium formulation available from FMC Corporation).

The weight ratio of the solid form of the compound of Formula A to the disintegrant may be between about 1:0.01 and about 1:1, optionally between about 1:0.03 and about 1:0.5, between about 1:0.05 and about 1:0.3 or between about 1:0.08 and about 1:0.16.

The disintegrant may be present in an amount of between about 0.1 wt % or about 50 wt %, optionally between about 0.5 wt % and about 30 wt %, or between about 1 wt % and about 20 wt %, or between about 1 wt % and about 10 wt % based on the total weight of the oral solid dosage form.

Alternatively or in addition, the oral solid dosage form may comprise a lubricant. The lubricant may comprise one or more of: magnesium stearate, calcium stearate, glyceryl monostearate, glycerylpalmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate. Preferably, the lubricant is magnesium stearate.

The weight ratio of the solid form of the compound of Formula A to the lubricant may be between about 1:0.001 and about 1:1, optionally between about 1:0.005 and about 1:0.5, between about 1:0.0075 and about 1:0.2 or between about 1:0.01 and about 1:0.1.

The lubricant may be present in an amount of between about 0.1 wt % and about 10 wt %, optionally between about 0.2 wt % and about 5 wt %, or between about 0.5 wt % and about 2 wt % based on the total weight of the oral solid dosage form.

Alternatively or in addition, the oral solid dosage form may comprise a glidant. The glidant may comprise one or more of: talc, colloidal silicon dioxide, magnesium trisilicate, powdered cellulose, starch and tribasic calcium phosphate.

The weight ratio of the solid form of the compound of Formula A to the glidant may be between about 1:0.01 and about 1:1.

The glidant may be present in an amount of between about 0.1 wt % and about 10 wt %, optionally between about 0.2 wt % and about 5 wt %, or between about 0.5 wt % and about 2 wt % based on the total weight of the oral solid dosage form.

Alternatively or in addition, the oral solid dosage form may comprise an acid. The acid may comprise one or more of: tartaric acid, maleic acid, succinic acid and citric acid. Preferably the acid is tartaric acid. Alternatively, the acid may be maleic acid.

The weight ratio of the solid form of the compound of Formula A to the acid may be between about 1:0.1 and about 1:2, optionally between about 1:0.2 and about 1:1.

The acid may be present in an amount of between about 1 wt % and about 40 wt %, optionally between about 2 wt % and about 30 wt %, or about 5 wt % and about 20 wt % based on the total weight of the oral solid dosage form.

Alternatively or in addition, the oral solid dosage form may comprise a surfactant. The surfactant may be an ionic surfactant or a non-ionic surfactant. The surfactant may comprise one or more of: sodium lauryl sulfate, polysorbate 20, polysorbate 40 and polysorbate 80. Optionally, the surfactant is selected from sodium lauryl sulfate and polysorbate 80. Optionally, the surfactant is sodium lauryl sulfate. Alternatively, the surfactant may be polysorbate 80.

The weight ratio of the solid form of the compound of Formula A to the surfactant may be between about 1:0.01 and about 1:1, optionally between about 1:0.03 and about 1:0.5 or between about 1:0.05 and about 1:0.3.

The surfactant may be present in an amount of between about 1 wt % and about 20 wt %, optionally between about 0.5 wt % and about 10 wt %, or between about 1 wt % and about 5 wt % based on the total weight of the oral solid dosage form.

The oral solid dosage form may comprise a lipid excipient. The lipid excipient may comprise one or more of: sucrose fatty acid esters, such as sucrose stearate, sucrose palmitate, sucrose laurate, sucrose behenate, sucrose oleate, sucrose erucate, and the like, and mixtures thereof; phospholipid derivatives, phosphatidyl derivatives, glycosylceramides derivatives, fatty acid derivatives, nonionic surfactants, vitamin E tocopheryl succinate polyethylene glycol derivatives (including D-α-Tocopherol polyethylene glycol succinate (TPGS)), glyceryl monooleate, Gelucire® series surfactants (which include, for example, Gelucire 44/14, Gelucire 33/01, and Gelucire 50/13), and glyceride derivatives. Optionally, the lipid excipient is Gelucire 44/14 and/or D-α-Tocopherol polyethylene glycol succinate (TPGS). Preferably, the lipid excipient is D-α-Tocopherol polyethylene glycol succinate (TPGS). Alternatively, the lipid excipient is Gelucire 44/14.

The melting point of the lipid excipient may be greater than about 25° C., greater than about 30° C., greater than about 35° C. or greater than about 40° C. Optionally, the melting point of the lipid excipient may be greater than about 35° C.

The melting point of the lipid excipient may be less than about 100° C., less than about 70° C., less than about 60° C. or less than about 50° C. Optionally, the melting point of the lipid excipient may be less than about 50° C.

The weight ratio of the solid form of the compound of Formula A to the lipid excipient may be between about 1:0.1 and about 1:100, optionally between about 1:0.5 and about 1:50, between about 1:1 and about 1:50, or between about 1:1 and about 1:20.

The lipid excipient may be present in an amount of between about 10 wt % and about 99 wt %, optionally between about 50 wt % and about 95 wt %, or between about 60 wt % and about 90 wt % based on the total weight of the oral solid dosage form.

The oral solid dosage form of the present invention may be in the form of a capsule. The capsule shell may be made from gelatin, hydroxypropyl methylcellulose or starch. Optionally, the capsule shell is made from gelatin. Optionally, the capsule shell is made from hydroxypropyl methylcellulose.

Alternatively, the oral solid dosage form of the present invention may be in the form of a tablet.

The oral solid dosage form of the present invention may comprise a coating, which may be in the form of a film. The coating may be an enteric coating. An enteric coating is insoluble at the strongly acid pH of the stomach, but soluble in the less acidic conditions in the small intestine. The coating may have mass/area of between about 1 mg/cm$^2$ and about 10 mg/cm$^2$, optionally between about 2 mg/cm$^2$ and about 8 mg/cm$^2$, or between about 3 mg/cm$^2$ and about 7 mg/cm$^2$.

The coating may have a mass of between about 10 mg and about 100 mg, optionally between about 20 mg and about 80 mg, or between about 30 mg and about 70 mg.

The mass of the coating per surface area of a size 0 dosage form, optionally in the form of a capsule, may be between about 10 mg and about 100 mg, optionally between about 20 mg and about 80 mg, or between about 30 mg and about 70 mg.

The enteric coating may comprise an enteric polymer which may comprise one or more of: shellac, cellulose acetate, cellulose acetate phthalate, hydroxypropyl methycellulose phthalate, trimellitate, polyvinyl acetate phthalate, or methacrylate-based polymers such as Eudragit L, Eudragit L100, Eudragit S, Eudragit S100, Eudragit L30D, and Eudragit L30-D55. Preferably, the enteric coating is Eudragit L30-D55.

The enteric coating may also comprise a plasticiser. The plasticiser may comprise one or more of: triethyl citrate, dibutyl phthalate, polyethylene glycols, propylene glycol, diethylphthalate, acetyl triethyl citrate. Preferably, the plasticiser is triethyl citrate.

The oral solid dosage form of the present invention may comprise a film wrapped around the core of the dosage form. Example of suitable film materials include HPMC, gelatin and Eudragit polymers. Preferably, the film material is HPMC.

The oral solid dosage form of the present invention may comprise one or more further active ingredients.

The present invention also provides a method of preparing an oral solid dosage form comprising a compound of Formula A, comprising the steps of
(a) mixing a solid form of the compound of Formula A which exhibits at least the following characteristic X-ray powder diffraction peaks (Cu Kα radiation, expressed in degrees 2θ) at approximately 11.2, 12.5, 13.2, 14.5 and 16.3 with a granulation fluid comprising a binder, and optionally a diluent, a disintegrant, and/or a surfactant;
(b) granulating the dispersion of step (a) to form granules;
(c) drying the granules;
(d) optionally blending the granules of step (b) or (c) with a diluent, an acid, a surfactant, and/or a lubricant to form blended granules; and
(e) compressing or filling the granules or blended granules into a solid oral dosage form.

The granulation fluid may further comprise water.

The drying in step (c) may be performed at a temperature greater than about 45° C., preferably greater than about 55° C. The drying in step (c) may be performed at a temperature of between about 45° C. and about 90° C., preferably between about 50° C. and about 80° C.

In step (e), the granules or blended granules may be compressed into a solid oral dosage form in the form of a tablet.

The present invention also provides a method of preparing an oral solid dosage form comprising a compound of Formula A, comprising the steps of
(a) dispersing a crystalline form of the compound of Formula A which exhibits at least the following characteristic X-ray powder diffraction peaks (Cu Kα radiation, expressed in degrees 2θ) at approximately 11.2, 12.5, 13.2, 14.5 and 16.3 in molten lipid excipient; and
(b) loading the molten dispersion into a capsule.

The present invention also provides a method of preparing an oral solid dosage form comprising a compound of Formula A, comprising loading a capsule with a crystalline form of the compound of Formula A which exhibits at least the following characteristic X-ray powder diffraction peaks (Cu Kα radiation, expressed in degrees 2θ) at approximately 11.2, 12.5, 13.2, 14.5 and 16.3.

It is to be understood that the components used in the methods of the present invention (e.g. binder, diluent, disintegrant, surfactant, acid, and lipid excipient) are the same components as described for the oral solid dosage forms of the present invention, and any definitions and/or limitations described for these components may apply equally to the components used in the methods of the present invention.

The present invention also provides an oral solid dosage form obtainable by any one of the methods of the present invention.

The oral solid dosage form of the present invention has a number of therapeutic applications, particularly in the treatment of diseases or conditions mediated by plasma kallikrein.

Accordingly, the present invention provides an oral solid dosage form comprising Form 1 of the compound of Formula A, for use in therapy.

The present invention also provides an oral solid dosage form as described herein for use in a method of treatment of a disease or condition mediated by plasma kallikrein.

The present invention also provides a method of treatment of a disease or condition mediated by plasma kallikrein, said method comprising administering to a mammal in need of such treatment an oral solid dosage form as described herein.

The present invention also provides a use of an oral solid dosage form as described herein in the manufacture of a medicament for the treatment of a disease or condition mediated by plasma kallikrein.

In an aspect, the disease or condition mediated by plasma kallikrein is selected from impaired visual acuity, diabetic retinopathy, retinal vascular permeability associated with diabetic retinopathy, diabetic macular edema, hereditary angioedema, retinal vein occlusion, diabetes, pancreatitis, cerebral haemorrhage, nephropathy, cardiomyopathy, neuropathy, inflammatory bowel disease, arthritis, inflammation, septic shock, hypotension, cancer, adult respiratory distress syndrome, disseminated intravascular coagulation, blood coagulation during cardiopulmonary bypass surgery, and bleeding from post-operative surgery. In a preferred embodiment, the disease or condition mediated by plasma kallikrein is diabetic macular edema. In another preferred embodiment, the disease or condition mediated by plasma kallikrein is hereditary angioedema.

Alternatively, the disease or condition mediated by plasma kallikrein may be selected from retinal vascular permeability associated with diabetic retinopathy, diabetic macular edema and hereditary angioedema. Alternatively, the disease or condition mediated by plasma kallikrein may be retinal vascular permeability associated with diabetic retinopathy or diabetic macular edema.

In the context of the present invention, references herein to "treatment" include references to curative, palliative and prophylactic treatment, unless there are specific indications to the contrary. The terms "therapy", "therapeutic" and "therapeutically" should be construed in the same way.

The oral solid dosage form of the present invention may be administered alone or in combination with one or more other pharmaceutical actives. In this regard, the oral solid dosage form may further comprise another pharmaceutical active ingredient. Alternatively, the oral dosage form of the invention may be co-administered (concurrently, consecutively or sequentially) with one or more further separate dosage forms incorporating the other pharmaceutical active(s).

In another aspect, the oral solid dosage form of the present invention may be administered in combination with laser treatment of the retina.

For administration to human patients, the total daily dose of the compound of Formula A is typically in the range about 0.1 mg and about 10,000 mg, or between about 1 mg and about 5000 mg, or between about 10 mg and about 1000 mg depending, of course, on the mode of administration.

The total daily dose may be administered in single or divided doses and may, at the physician's discretion, fall outside of the typical range given herein. These dosages are based on an average human subject having a weight of about 60 kg to 70 kg. The physician will readily be able to determine doses for subjects whose weight falls outside this range, such as infants and the elderly.

The oral solid dosage form of the present invention is intended to be administered orally. Oral administration may involve swallowing, so that the compound enters the gastrointestinal tract, and/or buccal, lingual, or sublingual administration by which the compound enters the blood stream directly from the mouth.

The invention will now be illustrated by the following non-limiting examples.

GENERAL EXPERIMENTAL DETAILS

In the following examples, the following abbreviations and definitions are used:

| | |
|---|---|
| Aq | Aqueous solution |
| DCM | Dichloromethane |
| DMF | N,N-Dimethylformamide |
| DMSO | Dimethyl sulfoxide |
| DSC | Differential Scanning Calorimetry |
| EtOAc | Ethyl Acetate |
| HATU | 2-(3H-[1,2,3]triazolo[4,5-b]pyridin-3-yl)-1,1,3,3-tetramethylisouronium hexafluorophosphate(V) |
| Hrs | Hours |
| HOBt | Hydroxybenzotriazole |
| IPA | 2-Propanol/Propan-2-ol/Iso-propanol |
| LCMS | Liquid chromatography mass spectrometry |
| Me | Methyl |
| MeCN | Acetonitrile |
| MeOH | Methanol |
| Min | Minutes |
| MS | Mass spectrum |
| NMR | Nuclear magnetic resonance spectrum-NMR spectra were recorded at a frequency of 400 MHz unless otherwise indicated |
| Pet. Ether | Petroleum ether fraction boiling at 60-80° C. |
| Ph | Phenyl |
| STA | Simultaneous Thermal Analysis |
| SWFI | Sterile water for injection |
| Rt | room temperature |
| THF | Tetrahydrofuran |
| TFA | Trifluoroacetic acid |
| XRPD | X-ray powder diffraction |

All reactions were carried out under an atmosphere of nitrogen unless specified otherwise.

$^1$H NMR spectra were recorded on a Bruker (400 MHz) or on a JEOL (400 MHz) spectrometer with reference to deuterium solvent and at rt.

Molecular ions were obtained using LCMS which was carried out using a Chromolith Speedrod RP-18e column, 50×4.6 mm, with a linear gradient 10% to 90% 0.1% $HCO_2H/MeCN$ into 0.1% $HCO_2H/H_2O$ over 13 min, flow rate 1.5 mL/min, or using Agilent, X-Select, acidic, 5-95% MeCN/water over 4 min. Data was collected using a Thermofinnigan Surveyor MSQ mass spectrometer with electrospray ionisation in conjunction with a Thermofinnigan Surveyor LC system.

Alternatively, molecular ions were obtained using LCMS which was carried out using an Agilent Poroshell 120 EC-C18 (2.7 µm, 3.0×50 mm) column with 0.1% v/v Formic acid in water [eluent A]; MeCN [eluent B]; Flow rate 0.8 mL/min and 1.5 minutes equilibration time between samples, gradient shown below.

Mass detection was afforded with API 2000 mass spectrometer (electrospray).

Gradient:

| Time (min) | Eluent A (%) | Eluent B (%) |
|---|---|---|
| 0.00 | 95 | 5 |
| 0.20 | 95 | 5 |
| 2.00 | 5 | 95 |
| 3.00 | 5 | 95 |
| 3.25 | 95 | 5 |
| 3.50 | 95 | 5 |

Where products were purified by flash chromatography, 'silica' refers to silica gel for chromatography, 0.035 to 0.070 mm (220 to 440 mesh) (e.g. Merck silica gel 60), and an applied pressure of nitrogen up to 10 p.s.i accelerated column elution. Reverse phase preparative HPLC purifications were carried out using a Waters 2525 binary gradient pumping system at flow rates of typically 20 mL/min using a Waters 2996 photodiode array detector.

All solvents and commercial reagents were used as received.

Chemical names were generated using automated software such as the Autonom software provided as part of the ISIS Draw package from MDL Information Systems or the Chemaxon software provided as a component of MarvinSketch or as a component of the IDBS E-WorkBook.

X-Ray Powder Diffraction patterns were collected on a Philips X-Pert MPD diffractometer and analysed using the following experimental conditions (Method A), unless otherwise specified:

Tube anode: Cu
Generator tension: 40 kV
Tube current: 40 mA
Wavelength alpha1: 1.5406 Å
Wavelength alpha2: 1.5444 Å

Start angle [2θ]: 4
End angle [2θ]: 40
Continuous scan

Approximately 2 mg of sample under analysis was gently compressed on the XRPD zero back ground single obliquely cut silica sample holder. The sample was then loaded into the diffractometer for analysis.

Where specified, X-Ray Powder Diffraction patterns were collected using the following method (Method B):

X-ray powder diffraction studies were performed using a Bruker AXS D2 PHASER (D2-205355) in Bragg-Brentano configuration, equipment #2353. A Cu anode at 30 kV, 10 mA, sample stage standard rotating (5/min) with beam stop and monochromatisation by a Kβ-filter (0.59% Ni) are used. The slits that are used are fixed divergence slits 1.0 mm) (=0.61°, primary axial Soller slit 2.5° and secondary axial Soller slit 2.5°. The detector is a linear detector LYNXEYE with receiving slit 5° detector opening. The standard sample holder (0.1 mm cavity in (510) silicon wafer) has a minimal contribution to the background signal. The measurement conditions: scan range 5-45° 2θ, sample rotation 5 rpm, 0.5 s/step, 0.010°/step, 3.0 mm detector slit; and all measuring conditions are logged in the instrument control file. The software used for data collection is Diffrac.Commander v4.0. Data analysis is performed using Diffrac.Eva V4.1 evaluation software. No background correction or smoothing is applied to the patterns.

DSC data were collected using the following method: Approximately 5 mg of each sample was weighed into an aluminium DSC pan and sealed non-hermetically with an aluminium lid. The sample was then loaded into a Perkin-Elmer Jade DSC and held at 30° C. Once a stable heat-flow response was obtained, the sample was then heated to a temperature between 200 and 300° C. at a scan rate of 10° C./min and the resulting heat flow response was monitored. A 20 cm³/min helium purge was used. Prior to analysis, the instrument was temperature and heat flow verified using an indium standard.

Gravimetric Vapour Sorption (GVS) data were collected using the following method: Approximately 10 mg of sample was placed into a wire-mesh vapour sorption balance pan and loaded into an 'IgaSorp' vapour sorption balance (Hiden Analytical Instruments). The sample was then dried by maintaining a 0% humidity environment until no further weight change was recorded. Subsequently, the sample was then subjected to a ramping profile from 0-90% RH at 10% RH increments, maintaining the sample at each step until equilibrium had been attained (99% step completion). Upon reaching equilibrium, the % RH within the apparatus was ramped to the next step and the equilibration procedure repeated. After completion of the sorption cycle, the sample was then dried using the same procedure. The weight change during the sorption/desorption cycles were then monitored, allowing for the hygroscopic nature of the sample to be determined.

Simultaneous Thermal Analysis (STA) data were collected using the following method: Approximately 5 mg of sample was accurately weighed into a ceramic crucible and it was placed into the chamber of Perkin-Elmer STA 600 TGA/DTA analyzer at ambient temperature. The sample was then heated at a rate of 10° C./min, typically from 25° C. to 300° C., during which time the change in weight was monitored as well as DTA signal. The purge gas used was nitrogen at a flow rate of 20 cm³/min.

I. Preparation of Form 1 of the Compound of Formula A

A. 1-(4-Hydroxymethyl-benzyl)-1H-pyridin-2-one 4-(Chloromethyl)benzylalcohol (5.0 g, 31.93 mmol) was dissolved in acetone (150 mL). 2-hydroxypyridine (3.64 g, 38.3 mmol) and potassium carbonate (13.24 g, 95.78 mmol) were added and the reaction mixture was stirred at 50° C. for 3 hrs after which time the solvent was removed in vacuo and the residue taken up in chloroform (100 mL). This solution was washed with water (30 mL), brine (30 mL), dried (Na$_2$SO$_4$) and evaporated in vacuo. The residue was purified by flash chromatography (silica), eluent 3% MeOH/97% CHCl$_3$, to give a white solid identified as 1-(4-hydroxymethyl-benzyl)-1H-pyridin-2-one (5.30 g, 24.62 mmol, 77% yield).

[M+Na]$^+$=238

B. 1-(4-Chloromethyl-benzyl)-1H-pyridin-2-one 1-(4-Hydroxymethyl-benzyl)-1H-pyridin-2-one (8.45 g, 39.3 mmol), dry DCM (80 mL) and triethylamine (7.66 ml, 55.0 mmol) were cooled in an ice bath. Methanesulfonyl chloride (3.95 ml, 51.0 mmol) was added and stirred in ice bath for 15 min. The ice bath was removed and stirring continued at rt temperature overnight. The reaction mixture was partitioned between DCM (100 mL) and saturated aqueous NH$_4$Cl solution (100 mL). The aqueous layer was extracted with further DCM (2×50 mL) and the combined organics washed with brine (50 mL), dried over Na$_2$SO$_4$, filtered and concentrated to give 1-(4-chloromethyl-benzyl)-1H-pyridin-2-one (8.65 g, 36.6 mmol, 93% yield) as a pale yellow solid.

[MH]$^+$=234.1

C. Methyl 3-(methoxymethyl)-1-(4-((2-oxopyridin-1 (2H)-yl)methyl)benzyl)-1H-pyrazole-4-carboxylate Potassium carbonate (519 mg, 3.76 mmol) was added to a solution of methyl 3-(methoxymethyl)-1H-pyrazole-4-carboxylate (320 mg, 1.88 mmol; CAS no. 318496-66-1 (synthesised according to the method described in WO 2012/009009)) and 1-(4-(chloromethyl)benzyl)pyridin-2(1H)-one (527 mg, 2.26 mmol) in DMF (5 mL) and heated at 60° C. overnight. The reaction mixture was diluted with EtOAc (50 mL) and washed with brine (2×100 mL), dried over magnesium sulfate, filtered and reduced in vacuo. The crude product was purified by flash chromatography (40 g column, 0-100% EtOAc in isohexanes) to afford two regioisomers. The second isomer off the column was collected to afford methyl 3-(methoxymethyl)-1-(4-((2-oxopyridin-1(2H)-yl) methyl)benzyl)-1H-pyrazole-4-carboxylate (378 mg, 1.01 mmol, 53.7% yield) as a colourless gum.

[MH]$^+$=368.2

D. 3-(Methoxymethyl)-1-(4-((2-oxopyridin-1(2H)-yl)methyl)benzyl)-1H-pyrazole-4-carboxylic Acid To methyl 3-(methoxymethyl)-1-(4-((2-oxopyridin-1 (2H)-yl)methyl)benzyl)-1H-pyrazole-4-carboxylate (3.77 g, 10.26 mmol) in THF (5 mL) and MeOH (5 mL) was added 2M NaOH solution (15.39 ml, 30.8 mmol) and stirred at rt overnight. 1M HCl (50 mL) was added and extracted with EtOAc (50 mL). The organic layer was washed with brine (50 mL), dried over magnesium sulfate, filtered and reduced in vacuo to give 3-(methoxymethyl)-1-(4-((2-oxopyridin-1

(2H)-yl)methyl)benzyl)-1H-pyrazole-4-carboxylic acid (1.22 g, 3.45 mmol, 33.6% yield) as a white powder.
[MH]$^+$=354.2

E. 3-Fluoro-4-methoxy-pyridine-2-carbonitrile

To a large microwave vial, copper (I) cyanide (1.304 g, 14.56 mmol) was added to a solution of 2-bromo-3-fluoro-4-methoxypyridine (1 g, 4.85 mmol) in DMF (5 mL). The reaction vial was sealed and heated to 100° C. for 16 hrs. The reaction mixture was diluted with water (20 mL) and EtOAc (20 mL). The thick suspension was sonicated and required additional water (40 mL) and EtOAc (2×50 mL) with sonication to break-up the solid precipitated. The combined layers were filtered through a plug of celite and the organic layer isolated, washed with brine (50 mL), dried over magnesium sulfate, filtered and the solvent removed under reduced pressure to give a pale green solid identified as the desired compound 3-fluoro-4-methoxy-pyridine-2-carbonitrile (100 mg, 0.578 mmol, 12% yield)

F. (3-Fluoro-4-methoxy-pyridin-2-ylmethyl)-carbamic Acid Tert-Butyl Ester

3-Fluoro-4-methoxy-pyridine-2-carbonitrile (100 mg, 0.578 mmol) was dissolved in anhydrous methanol (10 mL, 247 mmol) and nickel chloride hexahydrate (14 mg, 0.058 mmol) was added followed by di-tert-butyl dicarbonate (255 mg, 1.157 mmol). The resulting pale green solution was cooled in an ice-salt bath to −5° C. and then sodium borohydride (153 mg, 4.05 mmol) was added portionwise maintaining the reaction temperature ~0° C. The deep brown solution was left to stir at 0° C. and slowly allowed to warm to rt and then left to stir at rt for 3 hrs. The reaction mixture was evaporated to dryness at 40° C. to afford a black residue which was diluted with DCM (10 mL) and washed with sodium hydrogen carbonate (10 mL). An emulsion formed so the organics were separated via a phase separating cartridge and concentrated. The crude liquid was purified by chromatography eluting with EtOAc/iso-Hexane to afford the title compound, (3-fluoro-4-methoxy-pyridin-2-ylmethyl)-carbamic acid tert-butyl ester as a clear yellow oil (108 mg, 62% yield)
[MH]$^+$=257

G. C-(3-Fluoro-4-methoxy-pyridin-2-yl)-methylamine hydrochloride Salt (3-Fluoro-4-methoxy-pyridin-2-ylmethyl)-carbamic acid tert-butyl ester (108 mg, 0.358 mmol) was taken up in iso-propyl alcohol (1 mL) and then HCl (6N in iso-propyl alcohol) (1 mL, 0.578 mmol) was added at rt and left to stir at 40° C. for 2 hrs. The reaction mixture was concentrated under reduced pressure and then triturated with ether, sonicated and then decanted to give a cream coloured solid (75 mg, 55% yield) identified as C-(3-fluoro-4-methoxy-pyridin-2-yl)-methylamine hydrochloride salt.
[MH]$^+$=157

Example 1—N-[(3-Fluoro-4-methoxypyridin-2-yl)methyl]-3-(methoxymethyl)-1-({4-[(2-oxopyridin-1-yl)methyl]phenyl}methyl)pyrazole-4-carboxamide (Form 1)

3-(Methoxymethyl)-1-(4-((2-oxopyridin-1(2H)-yl) methyl)benzyl)-1H-pyrazole-4-carboxylic acid (825 mg, 2.34 mmol) and C-(3-fluoro-4-methoxy-pyridin-2-yl)-methylamine hydrochloride salt (450 mg, 2.34 mmol) were dissolved in DCM while cooling to 0° C. 1-Ethyl-3-(3-dimethylaminopropyl)carbodiimide hydrochloride (627.0 mg, 3.27 mmol), HOBt (378.8 mg, 2.80 mmol) and triethylamine (1.63 mL, 1182 mmol) were added while stirring, the mixture allowed to warm to rt and stirring continued for 20 hrs. Chloroform (50 mL) was added, the mixture was washed with saturated NaHCO$_3$(aq) and reduced in vacuo. The crude material was purified by chromatography eluting with methanol/DCM. The solvent was removed in vacuo and the resulting solid triturated with diethyl ether. The resulting solids were collected by filtration to afford the title compound.
[MH]$^+$=492.0

NMR (CD$_3$OD) δ: 3.41 (3H, s), 4.03 (3H, s), 4.65 (2H, s), 4.72 (2H, d, J=2.3 Hz), 5.24 (2H, s), 5.37 (2H, s), 6.44 (1H, td, J=1.4, 6.8 Hz), 6.62 (1H, d, J=9.0 Hz), 7.18-7.22 (1H, m), 7.31-7.38 (4H, m), 7.56-7.60 (1H, m), 7.75 (1H, dd, J=1.9, 7.1 Hz), 8.18 (1H, s), 8.27 (1H, d, J=5.6 Hz) ppm.

An XRPD diffractogram of the compound of Formula A (Form 1) is shown in FIG. 1a.

Peak position table:

| No. | Pos. [°2Th.] | Rel. Int. [%] |
| --- | --- | --- |
| 1 | 4.436 | 32.36 |
| 2 | 5.0471 | 58.74 |
| 3 | 10.2255 | 43.07 |
| 4 | 11.2061 | 48.44 |
| 5 | 12.0101 | 16.4 |
| 6 | 12.5494 | 37.17 |
| 7 | 13.165 | 67.26 |
| 8 | 14.4984 | 38.94 |
| 9 | 15.8919 | 23.54 |
| 10 | 16.2983 | 34.56 |
| 11 | 17.4492 | 36.63 |
| 12 | 17.8564 | 71.49 |
| 13 | 18.6888 | 21.9 |
| 14 | 20.285 | 26.12 |
| 15 | 21.1598 | 100 |
| 16 | 22.04 | 87.76 |
| 17 | 22.5857 | 36.38 |
| 18 | 23.4408 | 14.33 |
| 19 | 24.3045 | 31.11 |
| 20 | 25.1655 | 78.97 |
| 21 | 25.3728 | 93.91 |
| 22 | 26.4946 | 56.79 |
| 23 | 27.991 | 76.91 |
| 24 | 28.7495 | 22.99 |
| 25 | 30.7611 | 13.4 |
| 26 | 32.413 | 17.2 |
| 27 | 37.2144 | 14.13 |
| 28 | 38.1171 | 14.14 |

Figure 2:
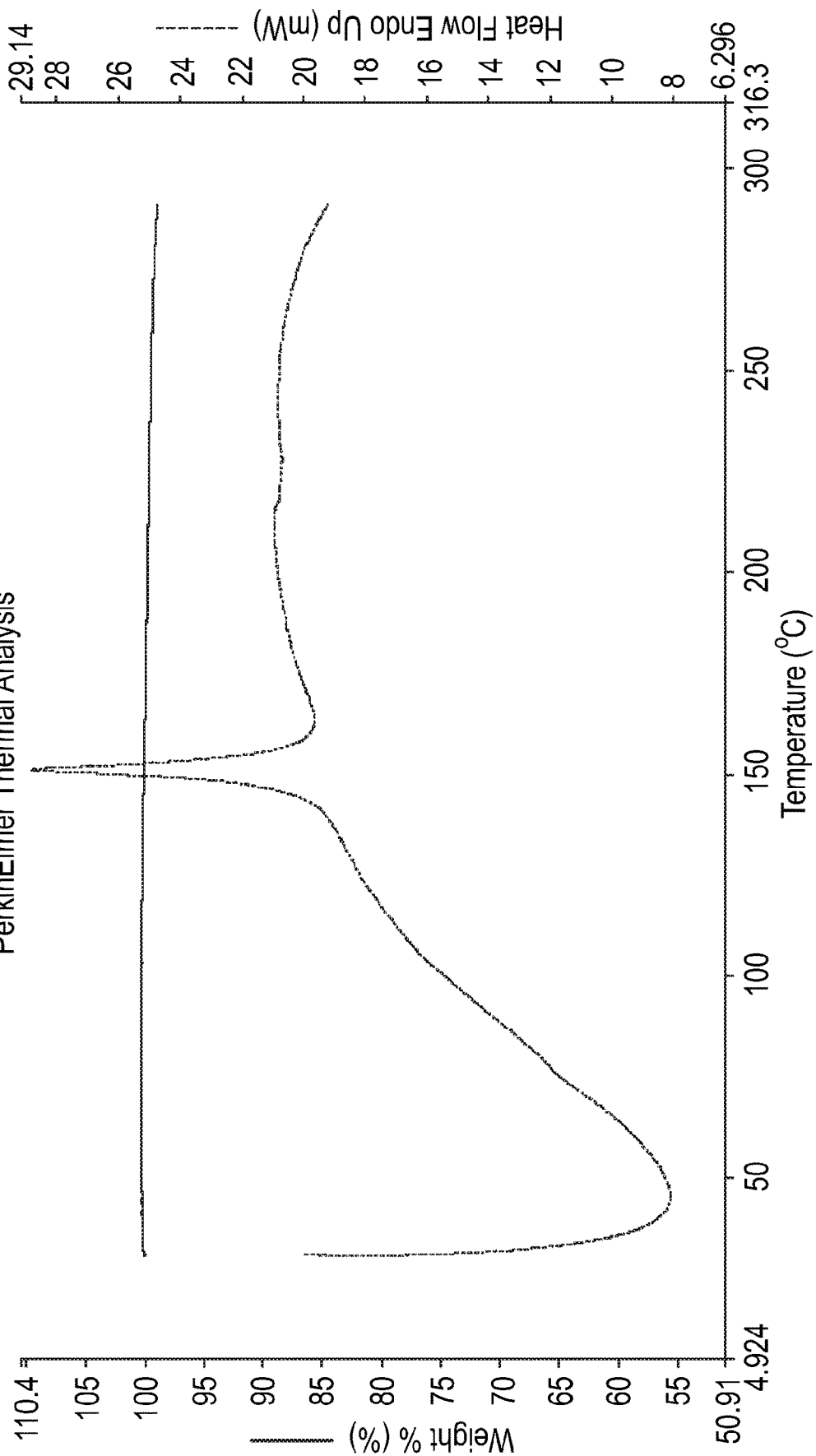
FIG. 2: STA of Form 1 of the compound of Formula A (Example 1).

Simultaneous Thermal Analysis (STA)
The STA data for Form 1 are shown in FIG. 2.
Differential Scanning Calorimetry (DSC)
The DSC data for Form 1 are shown in FIG. 3.
Gravimetric Vapour Sorption (GVS)
The GVS data for Form 1 are listed in the table below and shown in FIG. 4.

| %-RH | %-Wt(dry basis) |
| --- | --- |
| 0.0335 | 0.047222 |
| 9.9791 | 0.229954 |
| 20.0169 | 0.354118 |
| 30.0091 | 0.712554 |
| 39.9998 | 0.825004 |
| 49.991 | 1.206867 |

-continued

| %-RH | %-Wt(dry basis) |
|---|---|
| 59.9808 | 1.698837 |
| 70.0195 | 1.912025 |
| 80.0136 | 2.186122 |
| 90.0039 | 3.226288 |
| 85.0063 | 2.546901 |
| 75.0151 | 2.115841 |
| 64.9759 | 1.86517 |
| 54.9837 | 1.684781 |
| 44.9954 | 1.525476 |
| 35.0052 | 1.017107 |
| 25.0135 | 0.70084 |
| 15.0203 | 0.501709 |
| 4.9801 | 0.126875 |
| 0.0335 | 0.000368 |

Slurry Studies

Figure 5:
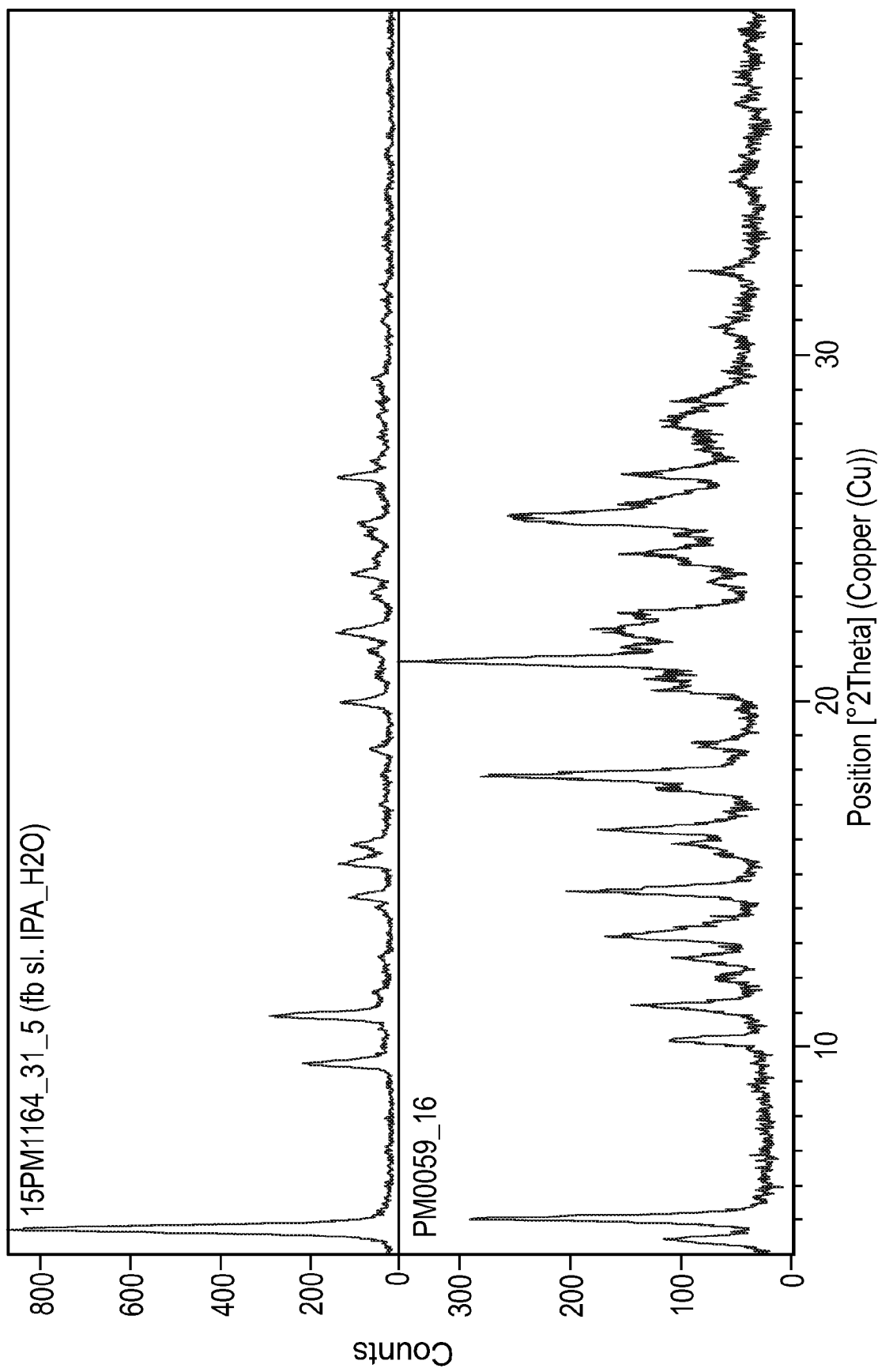
FIG. 5: X-ray powder diffraction pattern (top) of the compound of Formula A following slurry of Form 1 with 90:10 IPA:water. The bottom X-ray powder diffraction pattern is of Form 1 as a reference (Example 1).

Form 1 (20 mg) was suspended in 90/10 IPA/water (2004 or 3004) and shaken at ambient temperature for 72 hrs. The supernatant was evaporated rather than filtered due to the small volume and the resulting solid was examined by XRPD (FIG. 5). The resulting XRPD (FIG. 5) was different to that of FIG. 1a which indicated that the free base probably has a tendency to form hydrate(s).

Visual Aqueous Solubility

Form 1 (10 mg) was weighed into a glass vial and water was added in 1004 portions up to 3 mL then 1 mL portions thereafter. Solubility was assessed visually following a brief period of equilibration.

Form 1 did not give any indication it was dissolving at all in 20 mL water (<<0.5 mg/mL).

Example 2—N-[(3-Fluoro-4-methoxypyridin-2-yl)methyl]-3-(methoxymethyl)-1-({4-[(2-oxopyridin-1-yl)methyl]phenyl}methyl)pyrazole-4-carboxamide (Form 1)

3-(Methoxymethyl)-1-(4-((2-oxopyridin-1(2H)-yl)methyl)benzyl)-1H-pyrazole-4-carboxylic acid (825 mg, 2.34 mmol) and C-(3-fluoro-4-methoxy-pyridin-2-yl)-methylamine hydrochloride salt (450 mg, 2.34 mmol) were dissolved in DCM while cooling to 0° C. 1-Ethyl-3-(3-dimethylaminopropyl)carbodiimide hydrochloride (627.0 mg, 3.27 mmol), HOBt (378.8 mg, 2.80 mmol) and triethylamine (1.63 mL, 1182 mmol) were added while stirring, the mixture allowed to warm to rt and stirring continued for 20 hrs. Chloroform (50 mL) was added, the mixture was washed with saturated NaHCO$_3$(aq) and reduced in vacuo. The crude material was purified by chromatography eluting with methanol/DCM. The resulting solid was dissolved in hot MeCN, allowed to cool and precipitate, and the resulting solids were collected by filtration to afford the title compound as a white solid (130 mg, 11% yield).

Figure 1B:
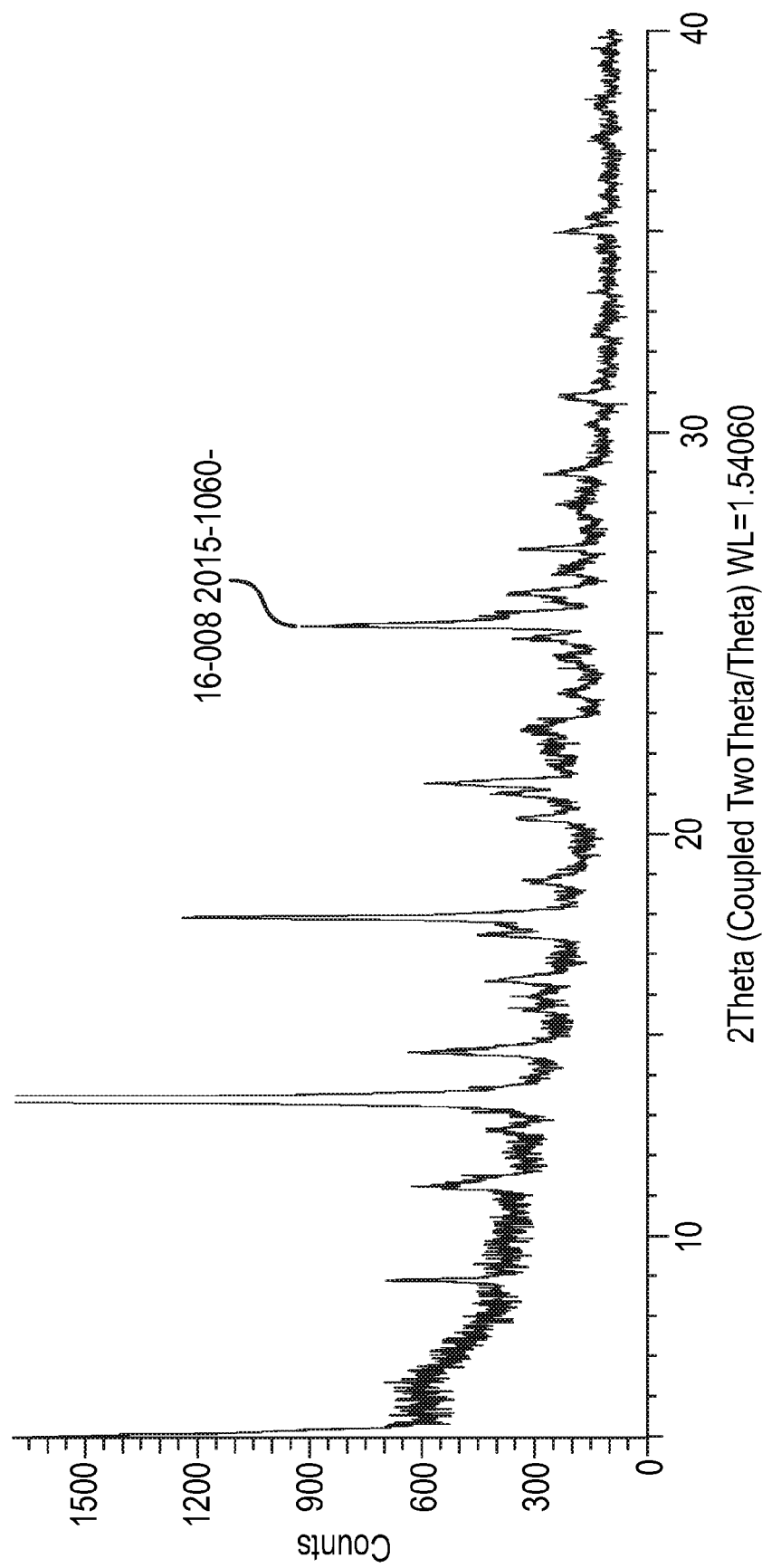
FIG. 1b: X-ray powder diffraction pattern of Form 1 of the compound of Formula A (Example 2).

An XRPD diffractogram (recorded using Method B) of the compound of Formula A (Form 1) is shown in FIG. 1b. The XRPD diffractogram (FIG. 1b) of the isolated solids confirmed that they were of the same solid form as Form 1 (Example 1) (FIG. 1a).

Peak position table:

| No. | Pos. [°2Th.] | Rel. Int. [%] |
|---|---|---|
| 1 | 4.3928 | 34.22 |
| 2 | 11.108 | 43.43 |
| 3 | 12.4938 | 29.35 |
| 4 | 13.1205 | 36.63 |
| 5 | 13.3366 | 100 |
| 6 | 14.4197 | 49.36 |
| 7 | 15.5175 | 14.68 |
| 8 | 15.8379 | 17.4 |
| 9 | 16.2139 | 51.86 |
| 10 | 17.3752 | 44.76 |
| 11 | 17.7813 | 72.85 |
| 12 | 18.6993 | 39.41 |
| 13 | 20.2369 | 23.49 |
| 14 | 21.126 | 95.26 |
| 15 | 22.012 | 39.31 |
| 16 | 22.5384 | 38.64 |
| 17 | 23.3774 | 25.27 |
| 18 | 24.2866 | 80.45 |
| 19 | 24.7288 | 52.68 |
| 20 | 25.0623 | 70.87 |
| 21 | 25.9156 | 37.33 |
| 22 | 26.5143 | 48.56 |
| 23 | 27.9517 | 49.02 |
| 24 | 28.7252 | 17.67 |
| 25 | 30.7541 | 34.12 |
| 26 | 34.8799 | 20.8 |
| 27 | 37.1548 | 15.95 |
| 28 | 38.1305 | 28 |

Example 3—N-[(3-Fluoro-4-methoxypyridin-2-yl)methyl]-3-(methoxymethyl)-1-({4-[(2-oxopyridin-1-yl)methyl]phenyl}methyl)pyrazole-4-carboxamide (Form 1)

3-(Methoxymethyl)-1-(4-((2-oxopyridin-1(2H)-yl)methyl)benzyl)-1H-pyrazole-4-carboxylic acid (61 g, 0.173 mol) was dissolved in DMF (400 mL) and 1,1'-carbonyldiimidazole (27.99 g, 0.173 mol) was added portion wise. Once the addition was complete, the reaction was heated to 50° C. for 2 hrs. C-(3-fluoro-4-methoxy-pyridin-2-yl)-methylamine (26.95 g, 0.17 3 mol) was added to the reaction mixture portion wise. The reaction was heated to 50° C. overnight. The reaction was cooled to rt and added dropwise to a 3:1 mixture of water and saturated NaHCO$_3$(aq) (4000 mL). The resulting suspension was stirred for 30 min before isolating the solids by filtration. The solids were washed with water (2×500 mL) before drying in a vacuum oven to give 119 g of the crude product. The crude product was combined with two other separate batches (starting with 0.173 mol and 0.0874 mol of the acid starting material respectively) and slurried together in IPA (1400 mL) and heated to reflux. Additional portions of IPA were added until all of the material had dissolved at reflux (total of 2000 mL IPA added). The solution was held at reflux for 30 min before it was cooled to rt. The mixture was cooled further with an ice/water bath for 30 min before the product was collected by filtration. The solids were washed with IPA and dried to give 167.2 g of the title product (78.5% yield).

[MH]$^+$=491.9

NMR (CD$_3$OD) spectrum conformed to the NMR spectrum of Form A.

Figure 1C:
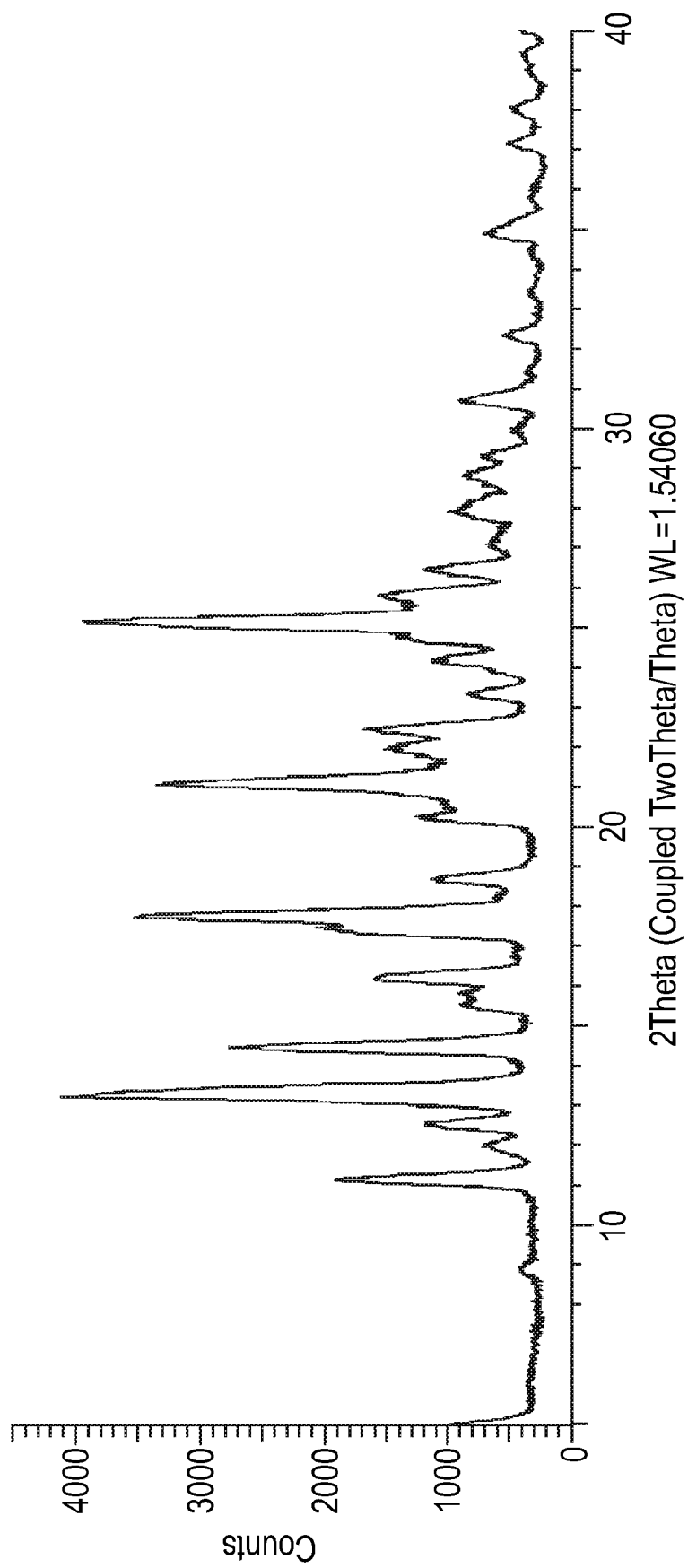
FIG. 1c: X-ray powder diffraction pattern of Form 1 of the compound of Formula A (Example 3).

An XRPD diffractogram (recorded using Method B) of the isolated solids (FIG. 1c) confirmed that they were of the same solid form as Form 1 (Example 1 and Example 2) (FIGS. 1a and 1b).

| No. | Pos. [°2Th.] | Rel. Int. [%] |
|---|---|---|
| 1 | 11.153 | 44.44 |
| 2 | 12.539 | 22.25 |
| 3 | 13.273 | 100.00 |

-continued

| No. | Pos. [°2Th.] | Rel. Int. [%] |
|---|---|---|
| 4 | 14.476 | 66.10 |
| 5 | 15.556 | 14.81 |
| 6 | 15.818 | 14.67 |
| 7 | 16.218 | 34.47 |
| 8 | 17.487 | 48.43 |
| 9 | 17.762 | 88.32 |
| 10 | 18.699 | 20.94 |
| 11 | 20.255 | 22.68 |
| 12 | 21.098 | 83.19 |
| 13 | 21.971 | 29.63 |
| 14 | 22.453 | 35.33 |
| 15 | 23.351 | 12.22 |
| 16 | 24.197 | 19.69 |
| 17 | 24.801 | 25.67 |
| 18 | 25.165 | 99.15 |
| 19 | 25.813 | 31.62 |
| 20 | 26.474 | 20.37 |
| 21 | 27.947 | 14.19 |
| 22 | 28.092 | 13.22 |
| 23 | 28.843 | 12.51 |
| 24 | 30.724 | 15.50 |
| 25 | 34.938 | 11.91 |

Peak position table:

Stability Data

A sample of Form 1 was packed in double polyethylene bags and sealed in a HDPE bottle and stored at conditions of 25° C./60% RH. The sample was reanalysed after 1 month and 3 months by XRPD (using Method B). The data is shown in FIG. 7. No change in the XRPD diffractogram was observed when the sample was stored at 25° C./60% RH after either 1 month or 3 months.

Further tests on the sample of Form 1 stored at 25° C./60% RH were carried out as described in Table 1:

TABLE 1

| | Testing intervals | | |
|---|---|---|---|
| Test | Initial | 1 month | 3 months |
| Appearance | Off-white solid | Off-white solid | Off-white solid |
| Identity by retention ratio | 1.00 | 1.00 | 1.00 |
| Purity by HPLC (area %) | 99.70 | 99.62 | 99.70 |
| Total impurities (area %) | 0.30 | 0.38 | 0.30 |
| Assay by HPLC (on an anhydrous and solvent free basis) (% w/w) | 101.0 | 99.5 | 99.6 |
| HPLC assay (on an "as is" basis) (% w/w) | 100.9 | 99.4 | 995 |
| Water by Karl Fischer analysis (% w/w) | <0.1 | <0.1 | <0.1 |
| Solid form of compound A by XRPD | Conforms to reference standard (Form 1) | Conforms to reference standard (Form 1) | Conforms to reference standard (Form 1) |
| DSC Tpeak (° C.) | 152.9 | 152.4 | 152.2 |
| DSC Tonset (° C.) | 151.3 | 151.1 | 150.8 |

A second sample of Form 1 was packed in double polyethylene bags and sealed in a HDPE bottle and stored under accelerated stability conditions of 40° C./75% RH. The sample was reanalysed after 1 month and 3 months by XRPD (using Method B). The data is shown in FIG. 8. No change in the XRPD diffractogram was observed when the sample was stored at 40° C./75% RH after either 1 month or 3 months.

Further tests on the sample of Form 1 stored at 40° C./75% RH were carried out as described in Table 2:

TABLE 2

| | Testing intervals | | |
|---|---|---|---|
| Test | Initial | 1 month | 3 months |
| Appearance | Off-white solid | Off-white solid | Off-white solid |
| Identity by retention ratio | 1.00 | 1.00 | 1.00 |
| Purity by HPLC (area %) | 99.70 | 99.57 | 99.71 |
| Total impurities (area %) | 0.30 | 0.43 | 0.29 |
| Assay by HPLC (on an anhydrous and solvent free basis) (% w/w) | 101.0 | 99.5 | 100.0 |
| HPLC assay (on an "as is" basis) (% w/w) | 100.9 | 99.4 | 99.9 |
| Water by Karl Fischer analysis (% w/w) | <0.1 | <0.1 | 0.1 |
| Solid form of compound A by XRPD | Conforms to reference standard (Form 1) | Conforms to reference standard (Form 1) | Conforms to reference standard (Form 1) |
| DSC Tpeak (° C.) | 152.9 | 152.3 | 152.5 |
| DSC Tonset (° C.) | 151.3 | 151.1 | 150.6 |

Example 4A—N-[(3-Fluoro-4-methoxypyridin-2-yl)methyl]-3-(methoxymethyl)-1-({4-[(2-oxopyridin-1-yl)methyl]phenyl}methyl)pyrazole-4-carboxamide (Form 3)

A suspension of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide (30 mg) in 50/50 methanol/water (100 µL) was matured by temperature cycling for 2 days. The resulting solids were isolated to afford N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide (Form 3).

An XRPD diffractogram of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide (Form 3) is shown in FIG. 6a.

Peak position table:

| No. | Pos. [°2Th.] | Rel. Int. [%] |
|---|---|---|
| 1 | 5.0236 | 100 |
| 2 | 10.0456 | 33.5 |
| 3 | 10.1526 | 38.94 |
| 4 | 12.6705 | 6.8 |
| 5 | 14.8188 | 2.96 |
| 6 | 15.2588 | 2.89 |
| 7 | 16.3621 | 5.53 |
| 8 | 17.5026 | 3.79 |
| 9 | 19.792 | 2.31 |
| 10 | 20.0456 | 3.56 |
| 11 | 20.6393 | 2.71 |
| 12 | 24.1662 | 2.7 |
| 13 | 25.643/1 | 1.49 |
| 14 | 26.8451 | 8.57 |
| 15 | 27.6821 | 1.13 |
| 16 | 35.3459 | 3.38 |

Example 4B—N-[(3-Fluoro-4-methoxypyridin-2-yl)methyl]-3-(methoxymethyl)-1-({4-[(2-oxopyridin-1-yl)methyl]phenyl}methyl)pyrazole-4-carboxamide (Form 5)

A suspension of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide (500 mg)

in 50/50 methanol/water (2.5 mL) was matured by temperature cycling from 20° C. to 50° C. for 24 hours. The resulting solids were isolated to afford N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide (Form 5).

Example 4C—N-[(3-Fluoro-4-methoxypyridin-2-yl)methyl]-3-(methoxymethyl)-1-({4-[(2-oxopyridin-1-yl)methyl]phenyl}methyl)pyrazole-4-carboxamide (Form 5)

A solution of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide (500 mg) in 50/50 methanol/water (20 mL) was prepared. The solution was allowed to evaporate to dryness under vacuum to afford N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide (Form 5).

Figure 6B:
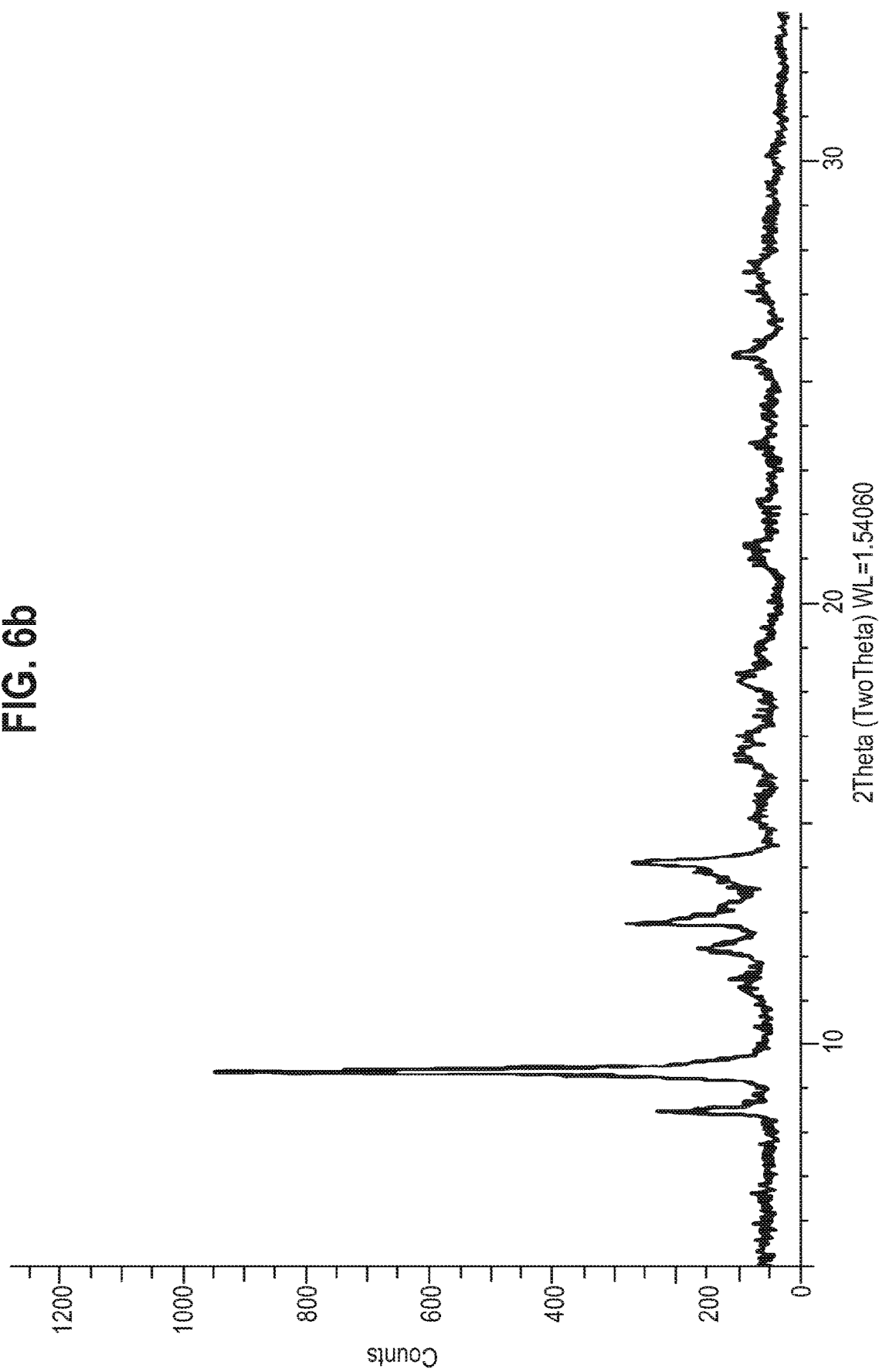
FIG. 6b: X-ray powder diffraction pattern of Form 5 of the compound of Formula A (Example 4c).

An XRPD diffractogram of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide (Form 5) obtained from Example 4C is shown in FIG. 6b. This XRPD diffractogram was obtained using Method B above.

Peak position table of most prominent peaks:

| No. | Pos. [°2Th.] | Rel. Int. [%] |
|---|---|---|
| 1 | 8.53 | 11.56 |
| 2 | 9.38 | 100 |
| 3 | 11.29 | 3.80 |
| 4 | 12.19 | 10.37 |
| 5 | 12.81 | 16.63 |
| 6 | 14.08 | 23.24 |
| 7 | 16.60 | 5.03 |
| 8 | 16.98 | 5.91 |
| 9 | 18.27 | 5.82 |
| 10 | 18.91 | 2.87 |
| 11 | 21.06 | 3.45 |
| 12 | 21.25 | 5.03 |
| 13 | 22.25 | 2.80 |
| 14 | 23.59 | 2.73 |
| 15 | 25.63 | 7.35 |
| 16 | 27.58 | 3.03 |

Form 5 is less stable than Forms 1, 2 or 3 and it converts into polymorph Form 3, over time. Performing an XRPD measurement on Form 5 resulted in Form 3.

Differential Scanning Calorimetry (DSC)

Figure 6C:
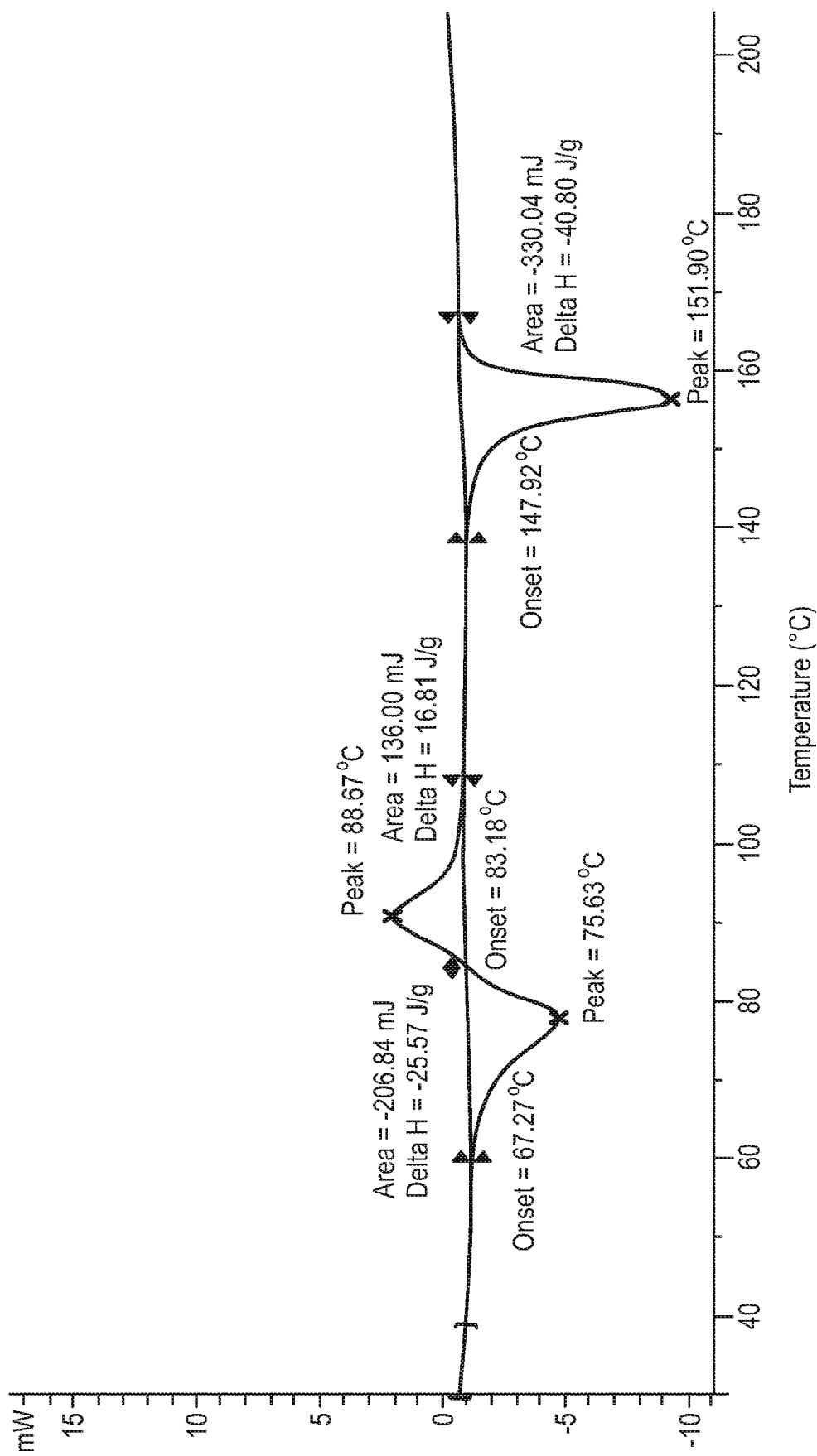
FIG. 6c: DSC thermograph of Form 5 of the compound of Formula A (Example 4c).
Figure 6D:
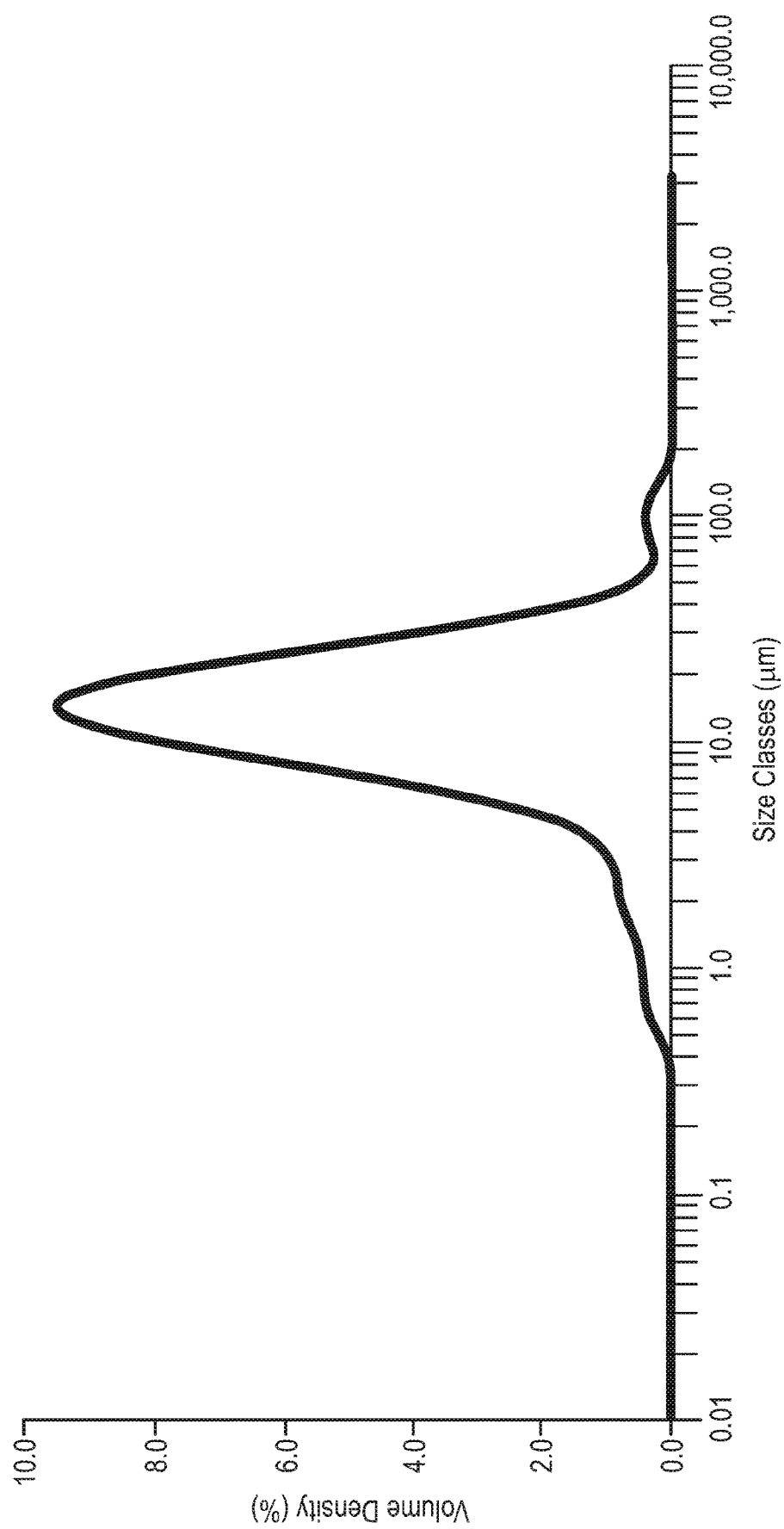
FIG. 6d: Particle size distribution of Form 5 of the compound of Formula A.

TGA/DSC studies were performed using a Mettler Toledo TGA/DSC1 Stare System, equipment #1547, auto-sampler equipped, using pin-holed Al-crucibles of 40 µl. Measurement conditions: 5 min 30.0° C., 30.0-350.0° C. with 10° C./min., N2 flow of 40 ml/min. The software used for instrument control and data analysis is STARe v12.10. The TGA/DSC data for Form 5 are shown in FIG. 6c Particle Size Distribution Particle size distribution studies were performed using a Malvern Instruments Mastersizer, equipment #1712. The Mastersizer used a 300RF lens range of 0.05 µm-900 mm. Polydisperse was used as analysis model. A background measurement was performed before each sample measurement, the background scan time was 12 seconds (12000 snaps). Each sample was dispersed in Multipar G, refractive index of 1.42. The obscuration range on sample dispersion was between 10%-30%. Each sample was measured 6 times at t=0 and t=30 minutes and the measurement scan time was 10 seconds (10000 snaps). The targeted stirring speed of the sample dispersion unit was 2000±10 rpm. Data collection and evaluation was performed using Mastersizer S Version 2.19 software. The resulting particle size distribution analysis of polymorph Form 5 is shown in FIG. 6d.

Gravimetric Vapour Sorption

Figure 6E:
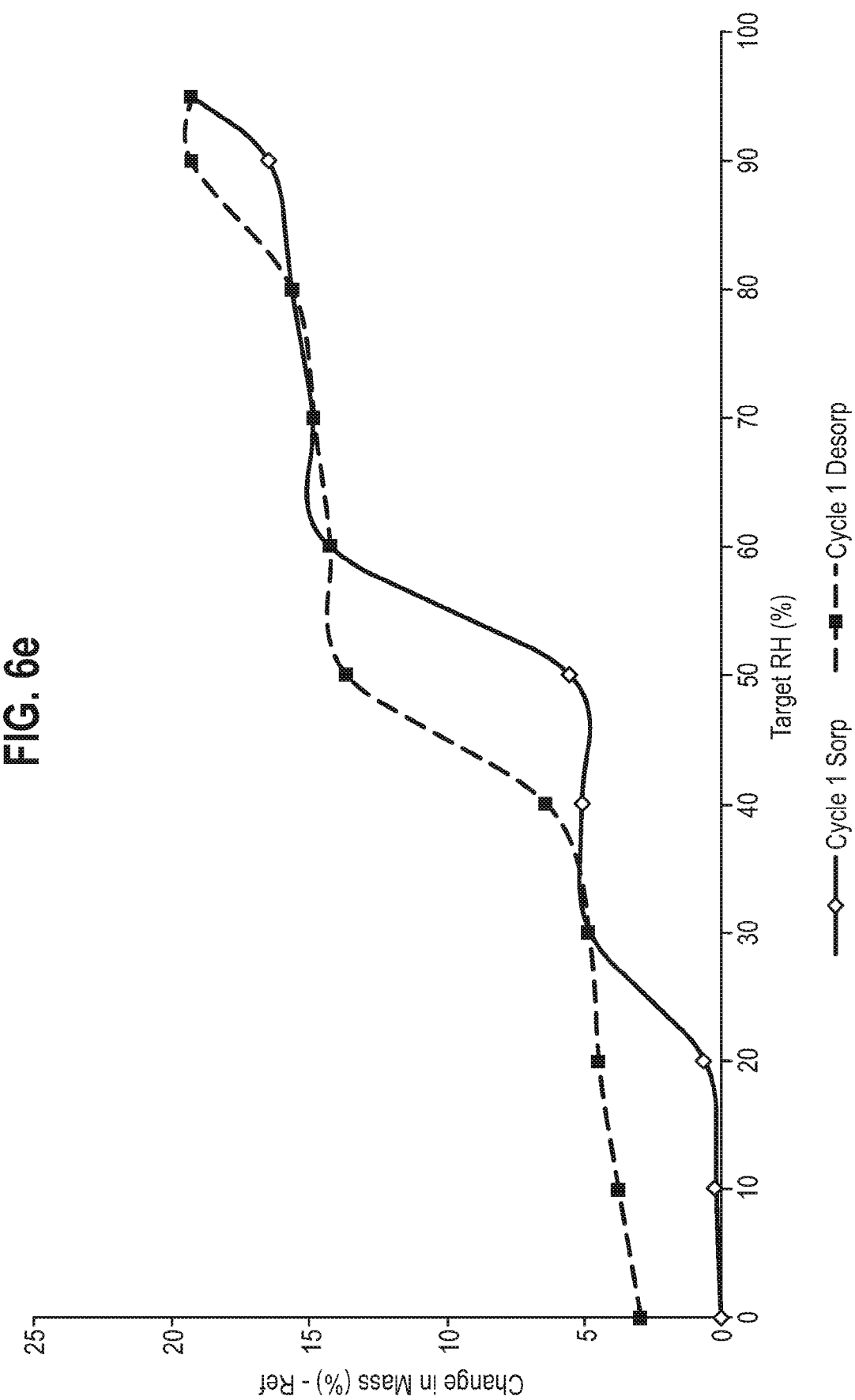
FIG. 6e: Gravimetric vapour sorption isotherms (adsorption and desorption) of Form 5 of the compound of Formula A (Example 4c).

Form 5 is hygroscopic with a mass uptake of 23%, as determined by Gravimetric Vapour Sorption (GVS) studies. The GVS studies were performed using a Surface Measurement Systems Ltd. DVS-1 No Video, equipment #2126. The sample was loaded into a balance pan, typically 20-30 mg, and equilibrated at 0% RH. After the material was dried, the RH was increased with 10% per step for 1 hour per increment, ending at 95% RH. After completion of the sorption cycle, the sample was dried using the same method. The software used for data collection was DVSWin v3.01 No Video. Data analysis was performed using DVS Standard Analysis Suite v6.3.0 (Standard). The resulting GVS is shown in FIG. 6e.

The data for Form 5 is summarised in the following table.

| DSC | | Particle Size Distribution | | | GVS |
|---|---|---|---|---|---|
| (Tpeak °C.) | TGA (mass loss %) | Dv(10) (µm) | Dv(50) (µm) | Dv(90) (µm) | (mass uptake %) |
| 75.6 (melt) | 1.11 (40° C.-80° C.) | 4.38 | 13.3 | 29.4 | 23 |
| 88.7 (recryst) | 0.62 (80° C.-100° C.) | | | | |
| 151.9 (melt) | 0.42 (100° C.-170° C.) | | | | |

II. Preparation of Oral Solid Dosage Forms from Form 1 of the Compound of Formula A Example 5A (Form 1 of the Compound of Formula A in a Capsule)

Form 1 of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide as prepared in Example 3 was passed through a 1.0 mm sieve. 100 mg of the resulting powder was then weighed into a size 0 gelatin capsule, and the capsule closed.

The flow and density characteristics, and particle size distribution of the powder prepared by passing Form 1 of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide as prepared in Example 3 through a 1.0 mm sieve were determined as follows. The range of humidity during the characterisation was 42-65%.

Flow and Density Characterisation of the Form 1 powder

The density (tapped and bulk) of the API was determined in duplicate according to USP [616] 2012 using tapped density apparatus. Carr's Index and Hausner ratio values were calculated from the tapped and bulk density figures recorded in accordance with USP [1174] 2010.

The mean results obtained from the duplicate measurements and calculations of bulk density, tap density, Carr's index and Hausner ratio are summarised in Table 3.

TABLE 3

| Test | Result | | |
|---|---|---|---|
| | Rep 1 | Rep 2 | Mean |
| Bulk Density (g/cm³) | 0.18 | 0.18 | 0.18 |
| Tap Density (g/cm³) | 0.25 | 0.26 | 0.26 |
| Carr's index (%) | 27.5 | 32.4 | 30.0 |
| Hausner ratio | 1.38 | 1.48 | 1.43 |

A Hausner ratio of less than 1.25 and a Carr's index value of between 5 to 15% indicate good/excellent flow properties (M. E. Aulton, Aulton's pharmaceutics the design and manufacture of medicines, 3$^{rd}$ Ed, Churchill Livingstone Elsevier, Hungary, 2007, p 356). The results in Table 3 for Form 1 indicate poor flow characteristics based on the Carr's Index and Hausner ratio.

Determination of powder flow (grams/second) of the powder prepared by passing Form 1 of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide as prepared in Example 3 through a 1.0 mm sieve was performed in duplicate using 'flow through an orifice apparatus' (25 mm and 10 mm in duplicate). The measurements were first performed without agitation of the flow meter. If no flow occurred, the test was repeated with gentle and repetitive tapping of the flow meter with a steel spatula (using a consistent strength each time). The results obtained for powder flow through a 25 mm and 10 mm orifice are shown in Table 4.

TABLE 4

| Test | Result-Without Tapping | | Result-With Tapping | |
|---|---|---|---|---|
| | Rep 1 | Rep 2 | Rep 1 | Rep 2 |
| Flow (25 mm) (g/s) | DNF* | DNF* | 1.33 | 1.84 |
| Flow (10 mm) (g/s) | DNF* | DNF* | DNF* | DNF* |

*DNF = Did not flow

The powder of Form 1 of the compound of Formula A did not flow through either a 25 mm or a 10 mm orifice without tapping and only the former with tapping, confirming the result obtained for the Carr's Index and Hausner ratio (Table 3). The powder of Form 1 of the compound of Formula A stuck to the spatula and sieves even though the humidity was relatively high. This behaviour may be impacted by humidity conditions.

The bulk density value measured for Form 1 of the compound of Formula A is low which means it is difficult to achieve high doses using simple powder blends (either directly encapsulated or compressed into tablets) because there will be limited available volume for the excipients that are needed to ensure adequate flow (within the constraints of suitable dose size).

Particle Size Distribution (PSD)

The particle size distribution of the powder prepared by passing Form 1 of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide as prepared in Example 3 through a 1.0 mm sieve was determined in duplicate by sieve analysis using a sieve shaker set at amplitude of 1 mm for 5 mins. The sieve sizes used were 1 mm, 710 μm, 500 μm, 355 μm, 250 μm, 125 μm, 63 μm and pan.

The results obtained for particle size determination are shown in Table 5.

TABLE 5

| Sieve (μm) | % of particles retained | |
|---|---|---|
| | Rep 1 | Rep 2 |
| 1000 | 8.2 | 5.1 |
| 710 | 6.1 | 4.7 |
| 500 | 4.5 | 7.7 |
| 355 | 12.4 | 15.7 |
| 250 | 20.7 | 24.8 |
| 125 | 39.2 | 42.1 |
| 63 | 8.7 | 2.5 |
| Base Pan | 0.3 | 0.1 |

The material retained in the higher aperture meshes appeared to be soft agglomerates. The fact that material was retained in the 1.0 mm mesh after the powder of Form 1 of the compound of Formula A had already been screened through a 1.0 mm mesh supports this observation and implies that the powder of Form 1 of the compound of Formula A spontaneously agglomerates. The majority of Form 1 was retained on the 125 and 250 μm sieves.

Example 5B (Form 1 of the Compound of Formula a in a Capsule)

Form 1 of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide as prepared in Example 3 was passed through a 1.0 mm sieve. 10 mg of the resulting powder was then weighed into a size 0 gelatin capsule, and the capsule closed.

Example 6—TPGS Formulation of Form 1 of the Compound of Formula A

Form 1 of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide as prepared in Example 3 was passed through a 1.0 mm sieve.

Tocopherol polyethylene glycol succinate (TPGS) (172 g) was heated to 65° C. using a water bath then Form 1 of the compound of Formula A (28 g) added to the molten TPGS with mixing using a Silverson mixer (Form 1 was added over 26 minutes with 4 minutes additional mixing, Silverson mixer set to 5400 RPM). The temperature of the mixture was adjusted to 55° C. for encapsulation. An aliquot of the mixture was drawn up using a Gilson pipette (set to 710 μL), dispensed into a size 0 gelatin capsule and allowed to cool to room temperature.

The drug loading of Form 1 of the compound of Formula A in the TPGS was 14.0% (w/w), and the fill weight of the mixture in the capsule was 719.0 mg. The dose for Form 1 of the compound of Formula A in the capsule was 100.7 mg.

Figure 9:
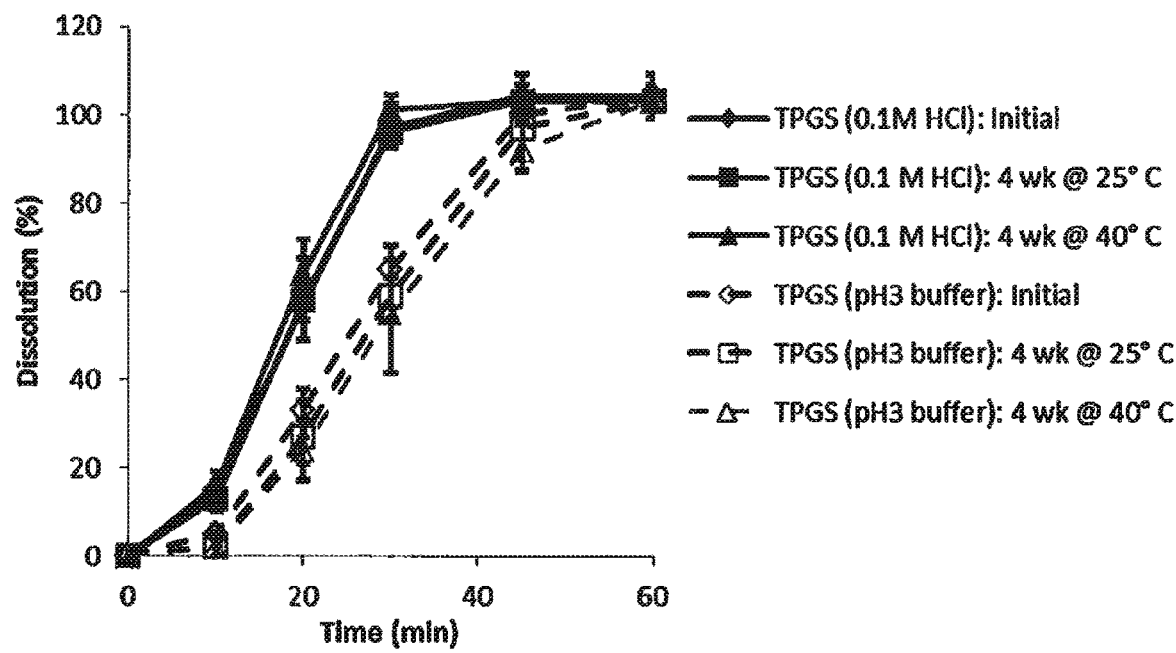
FIG. 9: Dissolution curves of the TPGS filled capsule in 0.1 M HCl and pH 3 buffer, initially and after storage at 25° C. and 40° C.

The results of dissolution testing of the resulting capsule in 0.1 M HCl and pH 3 buffer, initially and after storage at 25° C. and 40° C. are shown in FIG. 9.

The dissolution testing was performed according to Ph. Eur. 2.9.3 using a Distek dissolution apparatus using dissolution media of 0.1 M HCl, or pH 3 citric acid-phosphate buffer. Dissolution is run at 37° C. with paddle speed of 50 rpm. Samples (2 mL) are collected through a 4 μm cannula filter and processed through a 0.2 μm PVDF syringe filter into a UPLC vial for off line analysis. UPLC analysis is performed using 1.5 μL injection of sample on to a Waters

Example 7—Gelucire 44/14 Formulation of Form 1 of the Compound of Formula A

Form 1 of N-[(3-Fluoro-4-methoxypyridin-2-yl)methyl]-3-(methoxymethyl)-1-({4-[(2-oxopyridin-1-yl)methyl]phenyl}methyl)pyrazole-4-carboxamide as prepared in Example 3 was passed through a 1.0 mm sieve.

Gelucire 44/14 (172 g) was heated to 65° C. using a water bath then Form 1 of the compound of Formula A (28 g) added to the molten Gelucire 44/14 with mixing using a Silverson mixer (Form 1 was added over 17 minutes with 5 minutes additional mixing, Silverson mixer set to 5400 RPM). The temperature of the mixture was adjusted to 55° C. for encapsulation. An aliquot of the mixture was drawn up using a Gilson pipette (set to 710 μL), dispensed into a size 0 gelatin capsule and allowed to cool to room temperature.

The drug loading of Form 1 of the compound of Formula A in the Gelucire 44/14 was 14.0% (w/w), and the fill weight of the mixture in the capsule was 713.0 mg. The dose for Form 1 of the compound of Formula A in the capsule was 99.8 mg.

Figure 10:
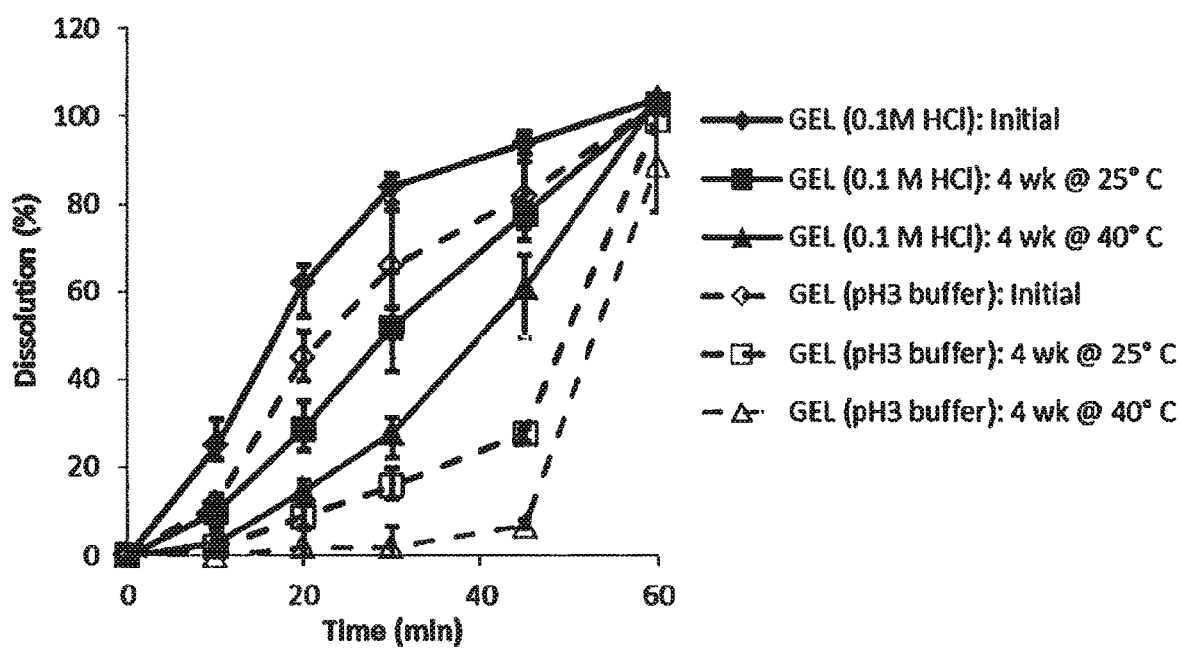
FIG. 10: Dissolution curves of the Gelucire 44/14 filled capsule in 0.1 M HCl and pH 3 buffer, initially and after storage at 25° C. and 40° C.

The results of dissolution testing of the resulting capsule in 0.1 M HCl and pH 3 buffer, initially and after storage at 25° C. and 40° C. are shown in FIG. 10.

The dissolution testing was performed according to Ph. Eur. 2.9.3 using a Distek dissolution apparatus using dissolution media of 0.1 M HCl, or pH 3 citric acid-phosphate buffer. Dissolution is run at 37° C. with paddle speed of 50 rpm. Samples (2 mL) are collected through a 4 μm cannula filter and processed through a 0.2 μm PVDF syringe filter into a UPLC vial for off line analysis. UPLC analysis is performed using 1.5 μL injection of sample on to a Waters CSH C18, 2.1×75 mm, 1.7 μm column with UV detection and an acetonitrile: water gradient over 2.5 minutes.

Example 8—TPGS Formulation of Form 1 of the Compound of Formula A (HPMC Capsule)

Form 1 of N-[(3-Fluoro-4-methoxypyridin-2-yl)methyl]-3-(methoxymethyl)-1-({4-[(2-oxopyridin-1-yl)methyl]phenyl}methyl)pyrazole-4-carboxamide as prepared in Example 3 was passed through a 1.0 mm sieve.

Tocopherol polyethylene glycol succinate (TPGS) (172 g) was heated to 78.4° C. using a water bath then Form 1 of the compound of Formula A (28 g) added to the molten TPGS (Form 1 was added over 26 minutes with 4 minutes additional mixing, Silverson mixer set to 5400 RPM). The temperature of the mixture was adjusted to 55° C., then subjected to high-shear homogenisation (174 min @ 1200 RPM then 230 min @ 2600 RPM). An aliquot of the mixture was drawn up using a Gilson pipette (set to 710 μL), dispensed into a size 0 HPMC capsule and allowed to cool to room temperature.

The drug loading of Form 1 of the compound of Formula A in the TPGS was 14.0% (w/w), and the fill weight of the mixture in the capsule was 717.8 mg. The dose for Form 1 of the compound of Formula A in the capsule was 100.5 mg.

Example 9—Tablet Formulations of the Compound of Formula A

Four granule formulations (referred to as $WG_A$, $WG_B$, $WG_C$ and $WG_D$) were prepared according to the following method using the amounts described in Table 6 and Table 7:

Primary granulation fluid was prepared by adding the components according to Table 6 into a mixing vessel (250 g for $WG_A$ and 200 g for $WG_B$, $WG_C$ and $WG_D$). The primary granulation fluid was stirred until homogeneous using either a magnetic flea, or an overhead stirrer.

For each sublot, Form 1 of the compound of Formula A, Avicel PH101 and AcDiSol were added to a Multipro high shear blender and blended at high speed for 5 minutes. While continuing to blend at high speed, the primary granulation fluid was poured into the mixture over the course of another 5 minutes. If material stuck to the side of the Multipro high shear blender, the process was interrupted and the material scraped down the vessel before recommencing the mixing & fluid addition.

At the end of the addition of the primary granulation fluid, the wet granule was mixed for another minute. Secondary granulation fluid was then slowly added with mixing over the course of another 5 minutes.

The resulting wet granule was passed through a 4.0 mm mesh. The wet granule was then placed into a stainless steel tray and dried in an oven overnight at the specified temperature. The dried granules were then passed through a 1 mm mesh and allowed to stand under ambient conditions for 2 hours to equilibrate. Granule formulations $WG_A$, $WG_B$, $WG_C$ and $WG_B$ were isolated.

TABLE 6

Granulation fluid formulation

| | Compositions (% w/w) | | | |
|---|---|---|---|---|
| Formulation Code | $WG_A$ | $WG_B$ | $WG_C$ | $WG_D$ |
| Povidone (Kollidon K25) | 6.67% | 6.06% | 6.67% | 6.06% |
| Tween 80 | — | 6.06% | — | 6.06% |
| Water | 93.33% | 87.88% | 93.33% | 87.88% |
| Total | 100.00% | 100.00% | 100.00% | 100.00% |

TABLE 7

Granule formulation

| | g per batch | | | |
|---|---|---|---|---|
| Granule Formulation | $WG_A$ | $WG_B$ | $WG_C$ | $WG_D$ |
| Solid form of the compound of Formula A | 66.66 | 50.00 | 100.00 | 50.00 |
| Microcrystalline cellulose (Avicel PH 101) | 87.34 | 65.51 | 131.00 | 65.51 |
| Croscarmellose sodium (AcDiSol) | 8.00 | 6.00 | 12.00 | 6.00 |
| Primary Granulation Fluid (Table 6) | 90.00 | 74.25 | 135.00 | 74.25 |

TABLE 7-continued

| Granule Formulation | Granule formulation | | | |
|---|---|---|---|---|
| | g per batch | | | |
| | $WG_A$ | $WG_B$ | $WG_C$ | $WG_D$ |
| Additional Secondary Granulation Fluid (Deionised Water) | Sublot 1: 80.2<br>Sublot 2: 81.5 | 60.30 | 51.20 | Nil |
| Overnight drying temperature | 40° C. | 40° C. | 60° C. | 60° C. |
| Number of Sublots | 2 | 1 | 1 | 1 |

The resulting $WG_A$ $WG_B$, $WG_C$ and $WG_B$ granules were characterised, and the results shown in Table 8. The methods used to measure each of the parameters are described below.

The LOD of the granules was determined using a 5 g sample of the granules using a Sartorius Moisture Balance at 105° C.

The density (tapped and bulk) of the granules was determined in duplicate according to USP [616] 2012 using tapped density apparatus. Carr's Index and Hausner ratio values were calculated from the tapped and bulk density figures recorded in accordance with USP [1174] 2010.

Determination of powder flow (grams/second) of the granules was performed in duplicate using 'flow through an orifice apparatus' (25 mm and 10 mm in duplicate). The measurements were first performed without agitation of the flow meter. If no flow occurred, the test was repeated with gentle and repetitive tapping of the flow meter with a steel spatula (using a consistent strength each time).

The particle size distribution of the granules was determined in duplicate by sieve analysis using a sieve shaker set at amplitude of 1 mm for 5 mins. The sieve sizes used were 1 mm, 710 μm, 500 μm, 355 μm, 250 μm, 125 μm, 63 μm and pan.

TABLE 8

| Granule characterisation data | | | | |
|---|---|---|---|---|
| Granule formulation | $WG_A$ | $WG_B$ | $WG_C$ | $WG_D$ |
| Solid form of the compound of Formula A | Form 3 | Form 1 | Form 1 | Form 1 |
| LOD (% w/w) | Sublot 1: 3.46<br>Sublot 2: 2.78 | 3.33 | 1.51 | 1.12 |
| Bulk Density (g/mL) | 0.51 | 0.50 | 0.42 | 0.59 |
| Tapped Density (g/mL) | 0.584 | 0.603 | 0.50 | 0.69 |
| Carr's Index | 12.7 | 16.9 | 14.8 | 14.8 |
| Hausner Ratio | 1.15 | 1.21 | 1.18 | 1.18 |
| Flow through 25 mm Orifice (g/s) | 60 | 75 | 49 | 69 |
| Flow through 10 mm Orifice (g/s) | 8 | 7 | 5 | 25 |
| Range of Humidity During Tests (% RH) | 35-43 | 56-57 | 40-47 | 36-40 |
| Retention on Sieves (% w/w) 1.0 mm | 0.8 | 0.8 | 3.0 | 2.3 |
| 710 μm | 8.4 | 13.6 | 13.3 | 22.6 |
| 500 μm | 19.0 | 15.5 | 7.6 | 28.0 |
| 355 μm | 37.6 | 26.1 | 6.7 | 22.5 |
| 250 μm | 23.5 | 28.4 | 10.7 | 10.4 |
| 125 μm | 10.1 | 14.4 | 47.1 | 10.8 |
| 63 μm | 0.9 | 1.0 | 11.0 | 4.0 |
| Base Pan | 0.1 | 0.4 | 1.2 | 0.3 |

The physical characterisation data shows that all the batches of granules were dry (i.e. <3.5% w/w) with good flow properties—the values for the Carr's Index and Hausner Ratio are both low, and the mass flow through the orifice was significant, even at 10 mm. Drying the granules at a temperature of 60° C. reduced the water content of the granules compared to the granules dried at 40° C. The granules were dense (bulk density >0.4 g/mL) and granular (the majority of the material retained on the 250 and 355 μm meshes during sieve analysis) and so are suitable for tabletting.

Eight tabletting formulations (referred to as T1 to T5, T1A, T2A and T5A, 95 g of each) were prepared according to the following method using the amounts described in Table 9:

The required amount of granule and each of the extra-granular excipients (except for the magnesium stearate) were dispensed into the blending vessel of an Erweka AR401 blender. The mixture was blended at 15 RPM for 15 minutes. Magnesium stearate was added to the blending vessel and the mixture blended for a further 5 minutes at 15 RPM.

TABLE 9

| | | Tablet formulation | | | | | | | |
|---|---|---|---|---|---|---|---|---|---|
| | | Composition (% w/w) | | | | | | | |
| | Tablet formulation code | T1 | T2 | T3 | T4 | T5 | T1A | T2A | T5A |
| | Granule formulation used | $WG_A$ | $WG_A$ | $WG_A$ | $WG_A$ | $WG_B$ | $WG_C$ | $WG_C$ | $WG_D$ |
| Intra-granular | Solid form of the compound of Formula A | | | 33.33 | | | 33.33 | 33.33 | 33.33 |
| | Microcrystalline cellulose (Avicel PH 101) | | | 43.67 | | | 43.67 | 43.67 | 43.67 |

TABLE 9-continued

| | | Tablet formulation | | | | | | | |
|---|---|---|---|---|---|---|---|---|---|
| | | Composition (% w/w) | | | | | | | |
| | Tablet formulation code | T1 | T2 | T3 | T4 | T5 | T1A | T2A | T5A |
| | Granule formulation used | $WG_A$ | $WG_A$ | $WG_A$ | $WG_A$ | $WG_B$ | $WG_C$ | $WG_C$ | $WG_D$ |
| | Croscarmellose sodium (AcDiSol) | | 4.00 | | | 4.00 | | 4.00 | 4.00 |
| | Povidone (Kollidon K25) | | 3.00 | | | 3.00 | | 3.00 | 3.00 |
| | Tween 80 | | | | | 3.00 | | | 3.00 |
| | Granule Total | 84.00 | 84.00 | 84.00 | 87.00 | 87.00 | 84.00 | 84.00 | 87.00 |
| Extra-granular | Microcrystalline cellulose (Avicel PH 102) | 15.00 | | | 12.00 | 12.00 | 15.00 | | 12.00 |
| | Tartaric acid | | 15.00 | | | | | 15.00 | |
| | Maleic acid | | | 15.00 | | | | | |
| | Sodium lauryl sulphate | | | | 3.00 | | | | |
| | Magnesium stearate | 1.00 | 1.00 | 1.00 | 1.00 | 1.00 | 1.00 | 1.00 | 1.00 |
| | Total | 100.00 | 100.00 | 100.00 | 100.00 | 100.00 | 100.00 | 100.00 | 100.00 |

Each resulting mixture was then pressed into tablets according to the following method: A Manesty F3 press was used to press the tablets. The press was set to 60 TPM with no tooling, then set up with round, normal concave tooling with a diameter of 8.3 mm, and an overload setting of 11 kN. The press was set up to produce tablets at a target of 300 mg weight against the overload spring. The cam setting was adjusted to the setting shown in Table 10.

250 tablets were prepared of each tablet formulation. At the start, middle and end of the tabletting process, the thickness, weight and hardness of 5 units were measured.

The physical characterisation data of the tablet formulations T1-T5, T1A, T2A and T5A are shown in Table 10.

The data in Table 10 were generated using the following standard procedures:

Hardness: Ph. Eur. 2.9.8
Friability: Ph. Eur. 2.9.7
Disintegration: Ph. Eur. 2.9.1

TABLE 10

| | | | | | | | Disintegration time in 0.1M HCl (min:sec) | | | | Disintegration time in pH 6 (min:sec) | |
|---|---|---|---|---|---|---|---|---|---|---|---|---|
| | | | | | | | Tableting Start | | Tableting End | | | |
| Batch Reference | Cam Setting | Point of measurement | Mean Weight (mg) | Mean Thickness (mm) | Mean Hardness (N) | Friability at the start, end (%)[1] | First | Last | First | Last | First | Last |
| T1 | 25 | Across entire batch | 294.4 | 4.82 | 77.0 | 0.09, 0.17 | 6:43 | 8:43 | 7:32 | 8:01 | | |
| T2 | N/R* | Across entire batch | 303.7 | 4.86 | 56.1 | 0.30, 0.12 | 6:27 | 7:16 | 7:59 | 9:14 | | |
| T3 | 26.5 | Across entire batch | 312.4 | 5.24 | 33.6 | 0.13, 0.04 | 5:46 | 6:13 | 7:09 | 8:04 | | |
| T4 | 25 | Across entire batch | 300.6 | 4.92 | 62.1 | 0.12, 0.23 | 2:53 | 3:20 | 3:13 | 4:02 | | |
| T5 | 26 | Across entire batch | 303.4 | 4.96 | 59.6 | 0.15, 0.17 | 4:24 | 5:03 | 3:52 | 5:47 | | |
| T1A | 35 | Start of run | 305.8 | 5.05 | 151.2 | 0.70 | 04:41 | 05:45 | | | | |
| | | Middle of run | 295.5 | 4.87 | 163.7 | 0.29 | | | | | | |
| | | End of run | 297.7 | 4.96 | 170.6 | 0.11 | | | 04:53 | 05:37 | | |
| T2A | 31 | Start of run | 295.3 | 5.63 | 31.1 | 0.3 | 00:10 | 00:21 | | | | |
| | | Middle of run | 293.2 | 5.66 | 30.6 | N/A | | | | | | |
| | | Final, random sample | 296.4 | 5.63 | 31.7 | 0.31 0.29 | | | 00:14 | 00:18 | 00:14 | 00:14 |
| T5A | 26 | Start of run | 300.5 | 4.93 | 75.3 | 0.01 | 08:25 | 11:14 | | | | |
| | | Middle of run | 300.8 | 5.16 | 39.1 | N/A | | | | | | |
| | | End of run | 296.9 | 5.03 | N/A | 0.04 | | | 01:44 | 02:39 | | |

*N/R = not recorded
[1]Friability of 10 tablets was measured on a sample prepared at the start and another at the end of tabletting.

The physical stability of the tablet formulations after storage at 25° C. and 40° C. for 4 weeks is compared to the initial data (Table 10) in Table 11. Formulations T1, T4 and T5 experience little or no change from initial.

TABLE 11

Comparison of physical characteristics of the tablet batches before and after 4 week storage

| Batch Reference | Timepoint | Weight (mg) | Tablet thickness (mm) | Hardness (N) | Disintegration Times in 0.1M HCl (min:sec) First* | Last* |
|---|---|---|---|---|---|---|
| T1 | Initial | 294.4 | 4.82 | 77.0 | 07:07 | 08:22 |
|  | 4 wk at 25° C. | 300.3 | 4.87 | 66.6 | 05:20 | 09:48 |
|  | 4 wk at 40° C. | 289.1 | 4.85 | 60.7 | 06:24 | 08:52 |
| T2 | Initial | 303.7 | 4.86 | 56.1 | 07:13 | 08:15 |
|  | 4 wk at 25° C. | 308.3 | 4.96 | 54.6 | 11:54 | 13:38 |
|  | 4 wk at 40° C. | 308.2 | 4.81 | 58.3 | 10:52 | 13:04 |
| T3 | Initial | 312.4 | 5.24 | 33.7 | 06:27 | 07:08 |
|  | 4 wk at 25° C. | 316.7 | 5.32 | 45.6 | 16:03 | >30 min |
|  | 4 wk at 40° C. | 309.8 | 5.43 | 125.2 | >30 min |  |

TABLE 11-continued

Comparison of physical characteristics of the tablet batches before and after 4 week storage

| Batch Reference | Timepoint | Weight (mg) | Tablet thickness (mm) | Hardness (N) | Disintegration Times in 0.1M HCl (min:sec) First* | Last* |
|---|---|---|---|---|---|---|
| T4 | Initial | 300.6 | 4.92 | 62.1 | 03:03 | 03:41 |
|  | 4 wk at 25° C. | 289.4 | 4.96 | 52.5 | 03:11 | 06:02 |
|  | 4 wk at 40° C. | 297.0 | 5.02 | 60.2 | 05:07 | 06:24 |
| T5 | Initial | 303.4 | 4.97 | 59.6 | 04:08 | 05:25 |
|  | 4 wk at 25° C. | 304.1 | 5.01 | 65.7 | 03:33 | 04:08 |
|  | 4 wk at 40° C. | 304.0 | 5.01 | 67.8 | 02:10 | 03:23 |

*Indicates the times for the first tablet and last tablet to disintegrate from the n = 3 tested for each timepoint. The disintegration times for the initial timepoints were taken as the average from the tablets at the start of tableting and those at the end of tableting.

The content uniformity of the dosage forms was determined using the following standard procedure: Eur. Ph. 2.9.40 (Uniformity of Dosage Units). Results are shown in Table 12.

TABLE 12

Content uniformity

| Sample | T1 | T1A | T2 | T2A | T3 | T4 | T5 | T5A | Example 6 (TPGS) | Example 8 (TPGS) | Example 7 (Gelucire) |
|---|---|---|---|---|---|---|---|---|---|---|---|
| Mean (%) | 105.6 | 99.1 | 101.9 | 98.9 | 101.3 | 101.5 | 105.8 | 105.6 | 95.6 | 101.0 | 99.7 |
| Standard Deviation (%) | 1.8 | 1.3 | 1.9 | 1.1 | 3.8 | 2.5 | 1.8 | 1.4 | 5.6 | 0.8 | 2.0 |
| AV | 8.5 | 3.1 | 4.9 | 2.6 | 9.2 | 6.1 | 8.5 | 6.8 | 16.3 | 1.8 | 2.9 |
| Minimum (%) | 101.5 | 97.6 | 98.8 | 97.8 | 97.7 | 97.2 | 104.2 | 101.5 | 87.3 | 100.1 | 97.7 |
| Maximum (%) | 107.4 | 102.3 | 105.2 | 101.0 | 109.1 | 104.2 | 110.3 | 106.6 | 104.1 | 102.2 | 103.0 |
| Pass/Fail | Pass | Pass | Pass | Pass | Pass | Pass | Pass | Pass | Fail | Pass | Pass |

Example 10

Tablet formulations T1A, T2A and T5A were selected for enteric coating.

The coating and physical testing of the T1A, T2A and T5A tablets was performed using an Aeromatic Strea-1 fluid bed dryer at controlled temperature range and average spray rate of 1.2 grams per minute to achieve a final weight gain of appropriately 50 mg coating.

The coating material is an aqueous suspension of Eudragit L30-D55 plasticised by Plasacryl HTP20 (at 33% of dry polymer substance containing triethyl citrate (TEC) as plasticiser and glycerol monostearate as anti-tacking agent). Components are manufactured by Evonik.

A coating formulation was prepared using the amounts described in Table 13

Table 13. The Eudragit L30-D55 was added to the deionised water with overhead stirring. The Plasacryl HTP20 was slowly added with stirring taking care not to aerate the liquid. The mixture was stirred for at least a further 10 minutes until the mixture was homogeneous. The suspension was passed through a 500 μm mesh.

The T1A, T2A and T5A tablets were sprayed with the coating formulation using an Aeromatic Strea-1 fluid bed dryer using the parameters described in Table 14 to produce coated tablets CT1A, CT2A and

CT5A.

TABLE 13

Coating formulation

| Ingredient | % (w/w) | Mass (g) | Component | Component % (w/w) | Coating solids composition after drying (% w/w) |
|---|---|---|---|---|---|
| Eudragit L30-D55 | 51.28 | 153.84 | Dry polymer | 13.85 | 69.2 |
| | | | Sodium lauryl sulfate | 0.36 | 1.8 |
| | | | Polysorbate 80 | 1.18 | 5.9 |
| | | | Water | 35.90 | — |
| Plasacryl HTP20 | 23.08 | 69.23 | TEC and glycerol monostearate | 4.62 | 23.1 |
| | | | Water | 18.46 | — |
| Deionised water | 25.64 | 76.93 | Water | 25.64 | — |

TABLE 14

| Coated tablet | Tablet | Measured Weight Gain (mg/Unit) | Overall Coating Efficiency | Spray Rate (g/min) Initial (Max) | Min | Mean | Coat Time (min) | Product Temperature range (° C.) | Atomising air range (bar) |
|---|---|---|---|---|---|---|---|---|---|
| CT1A | T1A | 48.6 | 30.4 | 2.75 | 0.6 | 1.2 | 73 | 22-35 | 1.2-1.5 |
| CT2A | T2A | 47.1 | 45.6 | 2.2 | 1.1 | 1.3 | 40 | 23.0-32.6 | 1.4-1.5 |
| CT5A | T5A | 49.0 | 37.2 | 2.2 | 0.8 | 1.1 | 63 | 21.7-32.2 | 1.3-1.6 |

The enteric coat had to meet the following criteria in the two stages of disintegration/dissolution testing (based on Ph. Eur. 2.9.1):
1. pH 3 citrate buffer: (a) no disintegration of the dose form within 2 hours and (b)<10% of API release during dissolution testing within 2 hours.
2. pH 6 phosphate buffer: the dose form should disintegrate within one hour.

The dissolution testing was performed according to Ph. Eur. 2.9.3 using a Distek dissolution apparatus using dissolution media of pH 3 citric acid-phosphate buffer. Dissolution is run at 37° C. with paddle speed of 50 rpm. Samples (2 mL) are collected through a 4 µm cannula filter and processed through a 0.2 µm PVDF syringe filter into a UPLC vial for off line analysis. UPLC analysis is performed using 1.5 µL injection of sample on to a Waters CSH C18, 2.1×75 mm, 1.7 µm column with UV detection and an acetonitrile:water gradient over 2.5 minutes.

TABLE 15

| Coated tablet | Measured Weight Gain (mg/Unit) | 2 hr Disintegration Test at pH 3: Result and Observations | Disintegration Time (min) at pH 6 |
|---|---|---|---|
| CT1A | 48.6 | 6/6 Pass | 17-19 |
| CT2A | 47.1 | 6/6 Pass | 3/6 Fail Times: 44, 46, 55, >1 hr |
| CT5A | 49.0 | 6/6 Pass | 31-40 |

CT1A

The coat weight applied (48.6 mg) was close to the target (49.5 mg), and no defects in the coat were apparent. These tablets passed the pH 3 test (no rupture within 2 hours) and the pH 6 test where disintegration was complete within 19 minutes. Six tablets were tested for dissolution in pH 3, but no dissolved API was detected within six hours. Hence these tablets passed specification of <10% dissolved within 2 hours.

CT2A

The coat weight applied (47.1 mg) was close to the target (49.5 mg), and no defects in the coat were apparent. These tablets passed the pH 3 test (no rupture within 2 hours). However three of the six tablets failed the pH 6 test (i.e. disintegration time >1 hour) with the remaining three tablets giving significantly slower disintegration than CT1A. While the functional coat had apparently fully disintegrated at 23-24 minutes in pH 6, large fragments of the core remained after 1 hour of testing. It should be noted that the disintegration of the pre-coated cores is very fast in all disintegration media, and so the coat must be causing the slow disintegration of the cores in pH 6.

The most likely explanation for the overly slow disintegration of the tablet cores is that the enteric polymer had penetrated the cores either during coating or during disintegration testing and had become neutralised by the presence of the tartaric acid. In its neutral form, the polymer is insoluble and may act as a binder preventing disintegration of the cores.

CT5A

The coat weight applied (49.0 mg) was close to the target (49.5 mg), and no defects in the coat were apparent. These tablets passed the pH 3 test (no rupture within 2 hours) and the pH 6 test where disintegration was complete within 31-40 minutes. Six tablets were tested for dissolution in pH3, but no dissolved API was detected within six hours. Hence these tablets passed specification of <10% API dissolved within 2 hours.

Example 11—Coated TPGS Capsule

The capsules of Example 6 were hand-banded using HPMC 606 ethanol/water solution, and subsequently coated with an aqueous dispersion of Eudragit L30-55 in a Caleva mini coater to achieve a 5.5 mg/cm$^2$ polymer weight gain. The capsules were coated in two batches of 14 capsules each. The coating solution composition is provided in Table 16.

First, triethyl citrate was pre-mixed with water at high sheer speed for 10 minutes, then the Eudragit suspension was added into the solution and gently mixed using a Heidolph mixer. The mixture was passed through a 0.5 mm sieve prior to use and continuously stirred during coating. The coating parameters are provided in Table 17.

TABLE 16

Composition of Eudragit L30-55 coating solution

| Function | Ingredient | Quantity based on dry polymer (%) | Quantity to be weighed (g) |
|---|---|---|---|
| Polymer | Eudragit L30-55 | — | 41.67 |
| Plasticiser | Triethyl citrate | 10.0 | 1.25 |
|  | Water | — | 50.83 |

TABLE 17

Enteric coating parameters

| Batch Size | 14 size 0 capsules |
|---|---|
| Agitator (Hz) | 12.2 |
| Fan speed (m/s) | 16.0 |
| Inlet air temperature (° C.) | 33 |
| Flow rate of coating solution (mL/min) | 0.1~0.2 |
| Atomising air pressure (bar) | 0.8~0.9 |
| Drying | 1 h at 38° C. |

Example 12

The granule formulations $WG_{A'}$ and $WG_{A''}$ were prepared according to the following method using the amounts described in Table 18 and Table 19:

Primary granulation fluid was prepared by adding the components according to Table 18 into a mixing vessel (600 g). The primary granulation fluid was stirred until homogeneous using either a magnetic flea, or an overhead stirrer.

For each sublot, Form 1 of the compound of Formula A, Avicel PH101 and AcDiSol were added to a Multipro high shear blender and blended at high speed for 5 minutes. While continuing to blend at high speed, the primary granulation fluid was poured into the mixture over the course of another 5 minutes. If material stuck to the side of the Multipro high shear blender, the process was interrupted and the material scraped down the vessel before recommencing the mixing & fluid addition.

At the end of the addition of the primary granulation fluid, the wet granule was mixed for another minute. Secondary granulation fluid was then slowly added with mixing over the course of another 5 minutes.

The resulting wet granule was passed through a 4.0 mm mesh. The wet granule was then placed into a stainless steel tray and dried in an oven overnight at 60° C. The dried granules were then passed through a 1 mm mesh and allowed to stand under ambient conditions overnight to equilibrate. Granule formulations $WG_{A'}$ and $WG_{A''}$ were isolated.

TABLE 18

Granulation fluid formulation

| | Composition (% w/w) | |
|---|---|---|
| Formulation Code | $WG_{A'}$ | $WG_{A''}$ |
| Povidone (Kollidon K25) | 6.67% | 6.67% |
| Water | 93.33% | 93.33% |
| Total | 100% | 100% |

TABLE 19

Granule formulation

| | g per batch | |
|---|---|---|
| Granule Formulation | $WG_{A'}$ | $WG_{A''}$ |
| Solid form of the compound of Formula A | 100.00 | 100.00 |
| Microcrystalline cellulose (Avicel PH 101) | 176.00 | 176.00 |
| Croscarmellose sodium (AcDiSol) | 12.00 | 6.00 |
| Primary Granulation Fluid (Table 18) | 135.00 | 135.00 |
| Additional Secondary Granulation Fluid (Deionised Water) | 55.1 | 55.1 |
| Number of Sublots | 1 | 1 |

The $WG_{A'}$ and $WG_{A''}$ granules were characterised, and the results shown in Table 20 Table 20. The methods used to measure each of the parameters are described below.

The LOD of the granules was determined using a 5 g sample of the granules using a Sartorius Moisture Balance at 105° C.

The density (tapped and bulk) of the granules was determined in duplicate according to USP [616] 2012 using tapped density apparatus. Carr's Index and Hausner ratio values were calculated from the tapped and bulk density figures recorded in accordance with USP [1174] 2010.

Determination of powder flow (grams/second) of the granules was performed in duplicate using 'flow through an orifice apparatus' (25 mm and 10 mm in duplicate). The measurements were first performed without agitation of the flow meter. If no flow occurred, the test was repeated with gentle and repetitive tapping of the flow meter with a steel spatula (using a consistent strength each time).

The particle size distribution of the granules was determined in duplicate by sieve analysis using a sieve shaker set at amplitude of 1 mm for 5 mins. The sieve sizes used were 1 mm, 710 µm, 500 µm, 355 µm, 250 µm, 125 µm, 63 µm and pan.

TABLE 20

| Granule formulation | $WG_{A'}$ | $WG_{A''}$ |
|---|---|---|
| Solid form of the compound of Formula A | Form 1 | Form 1 |
| LOD (% w/w) | 2.10 | 2.01 |
| LOD after 2 h equilibration (% w/w) | 2.87 | 2.40 |
| Bulk Density (g/mL) | 0.424 | 0.562 |
| Tapped Density (g/mL) | 0.503 | 0.654 |
| Carr's Index | 15.6 | 14.1 |
| Hausner Ratio | 1.19 | 1.17 |
| Flow through 25 mm Orifice (g/s) | 51 | 79 |
| Flow through 10 mm Orifice (g/s) | 5 | 8 |

TABLE 20-continued

| Granule formulation | | WG$_{A'}$ | WG$_{A''}$ |
|---|---|---|---|
| Range of Humidity During Tests (% RH) | | 53-62.5 | 53-62.5 |
| Retention on Sieves | 1.0 mm | 0.4 | 0.2 |
| (% w/w) | 710 μm | 6.5 | 1.7 |
| | 500 μm | 5.4 | 3.6 |
| | 355 μm | 4.3 | 7.6 |
| | 250 μm | 5.7 | 27.0 |
| | 125 μm | 41.9 | 49.0 |
| | 63 μm | 30.6 | 9.9 |
| | Base Pan | 5.3 | 1.4 |

Two tabletting formulations (referred to as T1A' and T1A", 150 g of each) were prepared according to the following method using the amounts described in Table 21:

The required amount of granule and each of the extra-granular excipients (except for the magnesium stearate) were dispensed into the blending vessel of an Erweka AR401 blender. The mixture was blended at 15 RPM for 15 minutes. Magnesium stearate was added to the blending vessel and the mixture blended for a further 5 minutes at 15 RPM.

TABLE 21

| | Tablet formulation | | |
|---|---|---|---|
| | | Composition (% w/w) | |
| | Tablet formulation code | T1A' | T1A" |
| | Granule formulation used | WG$_{A'}$ | WG$_{A''}$ |
| Intra-granular | Solid form of the compound of Formula A | 33.33 | 33.33 |
| | Microcrystalline cellulose (Avicel PH 101) | 58.67 | 58.67 |
| | Croscarmellose sodium (AcDiSol) | 4.00 | 2.00 |
| | Povidone (Kollidon K25) | 3.00 | 3.00 |
| | Granule Total | 99.00 | 97.00 |
| Extra-granular | Croscarmellose sodium (AcDiSol) | — | 2.00 |
| | Magnesium stearate | 1.00 | 1.00 |
| | Total | 100.00 | 100.00 |

Each resulting mixture was then pressed into tablets according to the following method:

A Manesty F3 press was used to press the tablets. The press was set to 40 TPM with no tooling, then set up with round, normal concave tooling with a diameter of 8.3 mm, and an overload setting as shown in Table 22. The press was set up to produce tablets at a target of 300 mg weight against the overload spring. The cam setting was adjusted to the setting shown in Table 22.

100 tablets were prepared of each tablet formulation. At the start, middle and end of the tabletting process, the thickness, weight and hardness of 5 units were measured.

The data in Table 22 were generated using the following standard procedures:

Hardness: Ph. Eur. 2.9.8

Friability: Ph. Eur. 2.9.7

Disintegration: Ph. Eur. 2.9.1

The LOD of the tablets was determined using a 5 g sample using a Sartorius Moisture Balance at 105° C.

TABLE 22

| Batch Reference | Overload setting (kN) | Cam Setting | Point of measurement | Mean Weight/ mg, (RSD %) | Mean Thickness (mm) | Mean Hardness (N) | Tensile strength (MPa) | Friability at the start, end (%)[1] | LOD (% w/w) | Disintegration time in 0.1M HCl (min:sec) First Tablet | Last Tablet | Disintegration time in deionised water (min:sec) First Tablet | Last Tablet |
|---|---|---|---|---|---|---|---|---|---|---|---|---|---|
| T1A' | 11 | 36 | Start of run | 306.7 (0.6%) | 5.00 | 175.2 | 1.78 | 0.12 | 4.10 | 22:58 | 26:20 | 08:38 | 08:42 |
| | | | end of run | 303.9 (0.5%) | 4.97 | 166.3 | 1.73 | 0.07 | | 21:41 | 22:01 | 07:58 | 08:27 |
| T1A' | 4 | 33 | Start of run | 310.4 (1.1%) | 5.56 | 79.6 | 0.73 | 0.06 | 4.78 | 0:11 | 0:14 | 01:00 | 01:10 |
| | | | end of run | 303.4 (0.8%) | 5.51 | 69.0 | 0.63 | 0.14 | | 0:15 | 1:02 | 01:05 | 01:15 |
| T1A' | 7 | 33 | Start of run | 309.7 (0.6%) | 5.23 | 130.9 | 1.28 | 0.33 | 4.25 | 01:10 | 01:20 | 00:11 | 00:15 |
| | | | end of run | 311.6 (0.5%) | 5.25 | 131.8 | 1.28 | 0.04 | | 01:40 | 01:53 | 00:13 | 00:15 |

The T1A' tablets were produced between 77±15 N (low hardness), and 162±20 N (high hardness). All set of tablets were close to target weight with good RSD, acceptable friability (<0.5%) and good disintegration times in water (<15 minutes).

During the tabletting of the T1A" batch, it was not possible to achieve tablets to meet the lower hardness target and the tablets produced were not any harder than 40 kN. The tablets appeared soft. T1A' (successfully compressed with granule having high level of fines) and T1A" (not compressed from granule with low levels of fines) only differed in terms of the point of addition of the AcDiSol.

III. Biological Methods

The ability of the compound of Formula A to inhibit plasma kallikrein may be determined using the following biological assays:

Determination of the IC$_{50}$ for plasma kallikrein

Plasma kallikrein inhibitory activity in vitro was determined using standard published methods (see e.g. Johansen et al., Int. J. Tiss. Reac. 1986, 8, 185; Shori et al., Biochem. Pharmacol., 1992, 43, 1209; Stürzebecher et al., Biol. Chem. Hoppe-Seyler, 1992, 373, 1025). Human plasma kallikrein (Protogen) was incubated at 25° C. with the fluorogenic substrate H-DPro-Phe-Arg-AFC and various concentrations of the test compound. Residual enzyme activity (initial rate of reaction) was determined by measuring the change in optical absorbance at 410 nm and the $IC_{50}$ value for the test compound was determined.

When tested in this assay, the compound of Formula A showed an $IC_{50}$ (human PKal) of 3.3 nM.

The compound of Formula A was also screened for inhibitory activity against the related enzyme KLK1 using the following biological assay:

Determination of the $IC_{50}$ for KLK1

KLK1 inhibitory activity in vitro was determined using standard published methods (see e.g. Johansen et al., Int. J. Tiss. Reac. 1986, 8, 185; Shori et al., Biochem. Pharmacol., 1992, 43, 1209; Stürzebecher et al., Biol. Chem. Hoppe-Seyler, 1992, 373, 1025). Human KLK1 (Callbiochem) was incubated at 25° C. with the fluorogenic substrate H-DVal-Leu-Arg-AFC and various concentrations of the test compound. Residual enzyme activity (initial rate of reaction) was determined by measuring the change in optical absorbance at 410 nm and the $IC_{50}$ value for the test compound was determined.

When tested in this assay, the compound of Formula A showed an $IC_{50}$ (human KLK1) of >40000 nM.

The compound of Formula A was also screened for inhibitory activity against the related enzyme FXIa using the following biological assay:

Determination of the % Inhibition for FXIa

FXIa inhibitory activity in vitro was determined using standard published methods (see e.g. Johansen et al., Int. J. Tiss. Reac. 1986, 8, 185; Shori et al., Biochem. Pharmacol., 1992, 43, 1209; Sturzebecher et al., Biol. Chem. Hoppe-Seyler, 1992, 373, 1025). Human FXIa (Enzyme Research Laboratories) was incubated at 25° C. with the fluorogenic substrate Z-Gly-Pro-Arg-AFC and 40 µM of the test compound. Residual enzyme activity (initial rate of reaction) was determined by measuring the change in optical absorbance at 410 nm.

When tested in this assay, the compound of Formula A showed a % inhibition @ 40 µM (human FXIa) of 0%.

IV. Pharmacokinetics

A pharmacokinetic study of the compound of Formula A was performed to assess the pharmacokinetics following a single oral dose in male Sprague-Dawley rats. Two rats were given a single po dose of 5 mL/kg of a nominal 2 mg/mL (10 mg/kg) composition of test compound in vehicle. Following dosing, blood samples were collected over a period of 24 hrs. Sample times were 5, 15 and 30 minutes then 1, 2, 4, 6, 8 and 12 hrs. Following collection, blood samples were centrifuged and the plasma fraction analysed for concentration of test compound by LCMS.

Oral exposure data acquired from this study for the compound of Formula A is shown in Table 23:

TABLE 23

| Oral exposure data | | | |
| --- | --- | --- | --- |
| Vehicle | Dose po (mg/kg) | Cmax (ng/mL) | Tmax (min) |
| 10% DMSO/10% cremophor/80% SWFI | 10.5 | 1534 | 180 |
| D-α-Tocopherol polyethylene glycol 1000 succinate (TPGS) solution (20% aq. w/v) | 10.1 | 1942 | 70 |

TABLE 24

In vivo pharmacokinetic data for oral solid dosage forms of the present invention

| PK screen | Formulation Description | Compound of Formula A (mg) | Cmax (ng/mL) | Tmax (min) | $T_{1/2}$ (h) | $AUC_{0-last}$ h*ng/mL |
| --- | --- | --- | --- | --- | --- | --- |
| D | API PIC (Example 5A) | 100 | 1280 | 60 | 4.12 | 2590 |
| E | Tween-80 tablet (T5) (Example 9) | 100 | 3209 | 60 | 3.00 | 5720 |
| F | TPGS Solid Dispersion (Example 6) | 100 | 3530 | 60 | 2.95 | 5500 |
| G | API Tablet (T1) (Example 9) | 100 | 1340 | 70 | 5.90 | 3410 |
| H | Tartaric acid tablet (T2) (Example 9) | 100 | 2354 | 100 | 3.16 | 4030 |
| I | API PIC (Example 5B) | 10 | 167 | 60 | | |
| J | CT1A (Tablet) (Example 10) | 100 | 292 | 480 | | |
| K | CT5A (Tween 80) (Example 10) | 100 | 89 | 360 | | |
| L | Enteric TPGS (Example 11) | 100 | 411 | 280 | | |
| M | T1 (Tablet) + CT1A Enteric (Examples 9 and 10) | 200 | 1580 | 100 | | |

In-Life Study

The test species was Cynomologous monkey. Oral solid dosage forms were administered by direct placement into the animal's stomach using a gavage tube and air displacement. Nominal 1 mL blood draws were collected into blood tubes containing 3.2% trisodium citrate as anticoagulant. Blood samples were processed by centrifugation to prepare plasma samples. Plasma samples were stored at less than −50° C. prior to analysis.

Plasma analysis was performed by the following method:

Quantification of the compound of Formula A from citrate preserved plasma was performed by protein precipitation using 4% acetic acid in acetonitrile. A Biotage ISOLUTE® PPT+ protein precipitation plate was used to filter out the precipitated proteins. Quantification of the compound of Formula A by LC-MS was performed on a Waters Quattro Micro API instrument with a calibration range of 1 to 3,160 ng/mL. Plasma concentration data analysis was performed using a non-compartmental model in WinNonlin.

The invention claimed is:

1. An oral solid dosage form comprising a solid form of the compound of Formula A Formula A wherein the solid form of the compound of Formula A exhibits at least the following characteristic X-ray powder diffraction peaks (Cu Kα radiation, expressed in degrees 2θ) at approximately 11.2, 12.5, 13.2, 14.5 and 16.3.

2. The oral solid dosage form of claim 1, wherein the amount of the solid form of the compound of Formula A in the dosage form is between 0.1 mg and 1,000 mg.

3. The oral solid dosage form of claim 1, wherein the solid form of the compound of Formula A is present in an amount of between 1 wt % and 70 wt % based on the total weight of the oral solid dosage form.

4. The oral solid dosage form of claim 1, further comprising a binder.

5. The oral solid dosage form of claim 1, further comprising a diluent.

6. The oral solid dosage form of claim 5, wherein the weight ratio of the compound of Formula A to the diluent is between 1:0.1 and 1:500.

7. The oral dosage form of claim 5, wherein the diluent comprises one or more of calcium carbonate, calcium phosphate-dibasic, calcium phosphate-tribasic, calcium sulfate, microcrystalline cellulose, powdered cellulose, a dextrate, a dextrin, a dextrose excipient, fructose, kaolin, lactitol, lactose, lactose monohydrate, mannitol, sorbitol, maltitol, starch, pregelatinized starch or sucrose.

8. The oral solid dosage form of claim 5, wherein the diluent is present in an amount of between 1 wt % and 99 wt % based on the total weight of the oral solid dosage form.

9. The oral solid dosage form of claim 1, further comprising a disintegrant, lubricant, and/or glidant.

10. The oral solid dosage form of claim 1, further comprising an acid.

11. The oral dosage form of claim 10, wherein the acid is present in an amount of between 1 wt % and 40 wt % based on the total weight of the oral solid dosage form.

12. The oral dosage form of claim 10, wherein the weight ratio of the compound of Formula A to the acid is between 1:0.1 and 1:2.

13. The oral solid dosage form of claim 10, wherein the acid is one or more of maleic acid, tartaric acid, succinic acid and citric acid.

14. The oral solid dosage form of claim 1, further comprising a surfactant.

15. The oral dosage form of claim 14, wherein the surfactant is present in an amount of between 1 wt % and 20 wt % based on the total weight of the oral solid dosage form.

16. The oral dosage form of claim 14, wherein the surfactant is present in an amount of between 1 wt % and 20 wt % based on the total weight of the oral solid dosage form, and/or wherein the weight ratio of the compound of Formula A to the surfactant is between 1:0.01 and 1:1.

17. The oral dosage form of claim 14, wherein the surfactant comprises sodium lauryl sulfate and/or Tween 80.

18. The oral solid dosage form of claim 1, further comprising a lipid excipient.

19. The oral dosage form of claim 18, wherein the excipient is present in an amount of between 10 wt % and 99% based on the total weight of the oral solid dosage form.

20. The oral dosage form of claim 18, wherein the weight ratio of the compound of Formula A to the lipid excipient is between 1:0.1 and 1:100.

21. The oral dosage form of claim 18, wherein the lipid excipient comprises one or more of a sucrose fatty acid ester, phospholipid derivative, phosphatidyl derivative, glycosylceramide derivative, fatty acid derivative, nonionic surfactant, vitamin E tocopheryl succinate polyethylene glycol (TPGS), D-α-tocopherol polyethylene glycol succinate (TPGS), glyceryl monooleate, a glyceride derivative, or mixtures thereof.

22. The oral dosage form of claim 21, wherein the sucrose fatty acid ester is sucrose stearate, sucrose palmitate, sucrose laurate, sucrose behenate, sucrose oleate, or sucrose erucate.

23. The oral solid dosage form of claim 1, wherein the oral solid dosage form is in the form of a capsule or a tablet.

24. The oral dosage form of claim 23, wherein the capsule shell is made from gelatin, hydroxypropyl methylcellulose or starch.

25. The oral dosage form of claim 23, further comprising a coating.

26. The oral solid dosage form of claim 25, wherein the coating is an enteric coating.

27. The oral solid dosage form of claim 1, comprising one or more further active ingredients.

28. The oral solid dosage form of claim 1, wherein the solid form of the compound of Formula A, wherein the solid form of the compound of Formula A exhibits at least the following characteristic X-ray powder diffraction peaks (Cu Kα radiation, expressed in degrees 2θ) at approximately 11.2, 12.5, 13.2, 14.5, 16.3, 17.4 and 17.9.

29. The oral solid dosage form of claim 1, wherein the solid form of the compound of Formula A exhibits an endothermic peak in its DSC thermograph at 151±3° C.

30. A method of treating a disease or condition mediated by plasma kallikrein, said method comprising administering to a mammal in need of such treatment an oral solid dosage form as claimed in claim 1.

31. The method of claim 30, wherein the disease or condition mediated by plasma kallikrein is selected from impaired visual acuity, diabetic retinopathy, retinal vascular permeability associated with diabetic retinopathy, diabetic macular edema, hereditary angioedema, retinal vein occlusion, diabetes, pancreatitis, cerebral haemorrhage, nephropathy, cardiomyopathy, neuropathy, inflammatory bowel disease, arthritis, inflammation, septic shock, hypotension, adult respiratory distress syndrome, disseminated intravascular coagulation, blood coagulation during cardiopulmonary bypass surgery and bleeding from post-operative surgery.

32. The method of claim 30, wherein the disease or condition mediated by plasma kallikrein is selected from retinal vascular permeability associated with diabetic retinopathy, diabetic macular edema and hereditary angioedema.

33. The method of claim 30, wherein the disease or condition mediated by plasma kallikrein is selected from retinal vascular permeability associated with diabetic retinopathy, and diabetic macular edema.

34. The method of claim 30, wherein the disease or condition mediated by plasma kallikrein is hereditary angioedema.

35. The method of claim 30, wherein the disease or condition mediated by plasma kallikrein is diabetic macular edema.

36. The oral solid dosage form of claim 1, wherein the binder is present in an amount of between 0.1 wt % and 30 wt % based on the total weight of the oral solid dosage form, and/or the weight ratio of the compound of Formula A to the binder is between 1:0.01 and 1:1.

37. The oral solid dosage form of claim 1, wherein the binder comprises one or more of methylcellulose, hydroxypropyl cellulose, hydroxypropyl methylcellulose, povidone, copovidone, gelatin, gum arabic, ethyl cellulose, polyvinyl alcohol, starch, pregelatinized starch, agar, tragacanth, or sodium alginate.

38. A method of preparing an oral solid dosage form comprising a compound of Formula A Formula A wherein the method comprises method (i), method (ii), or method (iii), method (i) comprising the steps of:
 (a) mixing a solid form of the compound of Formula A which exhibits at least the following characteristic X-ray powder diffraction peaks (Cu Kα radiation, expressed in degrees 2θ) at approximately 11.2, 12.5, 13.2, 14.5 and 16.3 with a granulation fluid comprising a binder;
 (b) granulating the dispersion of step (a) to form granules;
 (c) drying the granules;
 (d) optionally blending the granules of step (b) or (c) with a diluent, an acid, a surfactant, and/or a lubricant to form blended granules; and
 (e) compressing or filling the granules or blended granules into a solid oral dosage form; or
method (ii) comprising the steps of:
 (a) dispersing a solid form of the compound of Formula A which exhibits at least the following characteristic X-ray powder diffraction peaks (Cu Kα radiation, expressed in degrees 2θ) at approximately 11.2, 12.5, 13.2, 14.5 and 16.3 in molten lipid excipient;
 (b) loading the molten dispersion into a capsule; or
method (iii) comprising loading a capsule with a solid form of the compound of Formula A which exhibits at least the following characteristic X-ray powder diffraction peaks (Cu Kα radiation, expressed in degrees 2θ) at approximately 11.2, 12.5, 13.2, 14.5 and 16.3.

39. The method of claim 38 that is method (i) and wherein the drying in step (c) is performed at a temperature greater than 45° C. and/or in step (e), the granules or blended granules are compressed into a solid oral dosage form in the form of a tablet.

40. The method of claim 39, wherein step (c) is performed at greater than 55° C.

41. The method of claim 38 that is method (ii) and wherein the lipid excipient is D-α-tocopherol polyethylene glycol succinate (TPGS) or a glyceride derivative and/or the capsule shell is made from gelatin, hydroxypropyl methylcellulose or starch.

42. The method of claim 38, wherein the solid form of the compound of Formula A, wherein the solid form of the compound of Formula A exhibits at least the following characteristic X-ray powder diffraction peaks (Cu Kα radiation, expressed in degrees 2θ) at approximately 11.2, 12.5, 13.2, 14.5, 16.3, 17.4 and 17.9.

43. The method of claim 38, wherein the solid form of the compound of Formula A exhibits an endothermic peak in its DSC thermograph at 151±3° C.

44. The method of claim 38, wherein the granulation fluid further comprises water, a diluent, a disintegrant, and/or a surfactant.

45. The method of claim 38, further comprising:
 blending the granules of step (b) or (c) with a diluent, an acid, a surfactant, and/or a lubricant to form blended granules; and
 compressing or filling the blended granules into the solid oral dosage form.

46. The method of claim 38, wherein the lipid excipient is D-α-tocopherol polyethylene glycol succinate (TPGS).

47. A solid form of the compound of Formula A

Formula A wherein the solid form of the compound of Formula A exhibits an X-ray powder diffraction peak (Cu Kα radiation, expressed in degrees 2θ) at approximately 8.5.

48. The solid form of claim 47, wherein the solid form of the compound of Formula A further exhibits an X-ray powder diffraction peak (Cu Kα radiation, expressed in degrees 2θ) at approximately 12.8.

49. The solid form of claim 48, wherein the solid form of the compound of Formula A further exhibits an X-ray powder diffraction peak (Cu Kα radiation, expressed in degrees 2θ) at approximately 14.1.

50. The solid form of claim 49, wherein the solid form of the compound of Formula A further exhibits an X-ray powder diffraction peak (Cu Kα radiation, expressed in degrees 2θ) at approximately 9.4.

51. The solid form of claim 50, wherein the solid form of the compound of Formula A further exhibits an X-ray powder diffraction peak (Cu Kα radiation, expressed in degrees 2θ) at approximately 12.2.

52. The solid form of claim 47, wherein the solid form of the compound of Formula A has an X-ray powder diffraction pattern substantially the same as that shown in FIG. 6b.

53. A solid form of the compound of Formula A

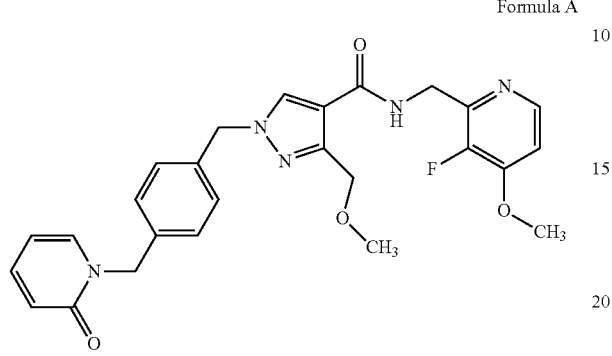

Formula A wherein the solid form of the compound of Formula A exhibits at least the following characteristic X-ray powder diffraction peaks (Cu Kα radiation, expressed in degrees 2θ) at approximately 12.8 and 14.1.

* * * * *